(12) United States Patent
Turnbull et al.

(10) Patent No.: US 7,834,063 B2
(45) Date of Patent: Nov. 16, 2010

(54) BENZONITRYL AND NITROBENZYL DERIVATIVES THAT MODULATE ANDROGEN RECEPTORS

(75) Inventors: Philip Stewart Turnbull, Durham, NC (US); Andrew Lamont Larkin, Durham, NC (US); Istvan Kaldor, Durham, NC (US); Rodolfo Cadilla, Durham, NC (US); David John Cowan, Durham, NC (US); Eugene Lee Stewart, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 185 days.

(21) Appl. No.: 11/576,965

(22) PCT Filed: Oct. 13, 2005

(86) PCT No.: PCT/US2005/037094

§ 371 (c)(1),
(2), (4) Date: Mar. 12, 2008

(87) PCT Pub. No.: WO2006/044707

PCT Pub. Date: Apr. 27, 2006

(65) Prior Publication Data

US 2008/0255124 A1    Oct. 16, 2008

Related U.S. Application Data

(60) Provisional application No. 60/618,480, filed on Oct. 13, 2004.

(51) Int. Cl.
*A61K 31/135* (2006.01)
(52) U.S. Cl. .................. 514/651; 564/353; 514/351; 514/331; 546/230; 546/300
(58) Field of Classification Search .................. 514/651, 514/331, 351
See application file for complete search history.

(56) References Cited

U.S. PATENT DOCUMENTS

| 3,629,330 | A | 12/1971 | Brody et al. | |
|---|---|---|---|---|
| 2006/0178398 | A1* | 8/2006 | Adams et al. | 514/312 |
| 2008/0058383 | A1* | 3/2008 | Jernstedt et al. | 514/336 |

FOREIGN PATENT DOCUMENTS

| EP | 1475368 A1 | 11/2004 | |
|---|---|---|---|
| JP | 2001261657 | * | 9/2001 |
| WO | WO 99/16761 | * | 4/1999 |
| WO | 03049739 A1 | 6/2003 | |
| WO | 03058753 A1 | 8/2003 | |
| WO | 03106401 A1 | 12/2003 | |

OTHER PUBLICATIONS

ZCAPLUS 1997:617954-WO9732562, Brenton et al., 1997.*
Attias et al.; "Chemical Structure of Networks Resulting from Curing of N,N-Diglycidylaniline-Type Resins with Aromatic Amines. II. Detection and Characterization of Intermolecular Etherification on Model Compounds"; Journal of Polymer Science, Part A: Polymer Chemistry; 1990; vol. 28; pp. 1661-1679.
Craig et al.; "Amine Exchange Reactions. Mannich Bases from Aromatic Amines"; Journal of Organic Chemistry; 1964; vol. 29; pp. 410-415.
Das et al.; "Transmission of Substituent Effects through -N-E-N- Systems in Unsymmetrically N,N'-Substituted Heteroimidazolidines Where E = C, Si, P(III), P(V), and B"; Journal of the American Chemical Society; 1977; vol. 99 (5); pp. 1354-1359.
Elpern et al.; "Strong Analgesics. The Preparation of Some Ethyl 1-Anilinoalkyl-4-Phenylpiperidine-4-Carboxylates"; Journal of the American Chemical Society; 1959; vol. 81; pp. 3784-3786.
Leonard et al.; "Synthesis and Pharmacological Activities of 2-(3'-substituted-2'-hydroxypropylamino)pyridines"; Biol. Pharm, Bull.; 2002; vol. 25(2); pp. 215-217.
Muruganantham et al.; "Synthesis, Anticonvulsant and Antihypertensive Activities of 8-Substituted Quinoline Derivatives"; Biol. Pharm. Bull.; 2004; vol. 27(10); pp. 1683-1687.
Narendar et al.; "Pharmacological Evaluation of Some New 2-Substituted Pyridine Derivatives"; Biol. Pharm. Bull.; 2003; vol. 26(2); pp. 182-187.
Nemoto et al.; "Polyamides for Nonlinear Optics Containing Second-Order NLO-phores with High Density"; Chem. Mater.; 1996; vol. 8(7); pp. 1527-1534.
Perillo et al.; "Synthesis of 1,2-Disubstituted-1,4,5,6-tetrahydropyrimidines"; Journal of Heterocyclic Chemistry; 1973; vol. 10; pp. 915-923.

* cited by examiner

*Primary Examiner*—Kamal A Saeed
*Assistant Examiner*—Valerie Rodriguez-Garcia
(74) *Attorney, Agent, or Firm*—Kathryn L. Coulter; Jennifer L. Fox

(57) ABSTRACT

This invention relates to benzonitryl and nitrobenzyl derivatives that are modulators of androgen, glucocorticoid, mineralocorticoid, and progesterone receptors, and also to the methods for the making and use of such compounds. These compounds are useful, for example, in the treatment or prophylaxis of conditions or disorders that respond to selective androgen receptor modulation.

17 Claims, No Drawings

BENZONITRYL AND NITROBENZYL DERIVATIVES THAT MODULATE ANDROGEN RECEPTORS

CROSS-REFERENCE TO RELATED APPLICATIONS

This application is filed pursuant to 35 U.S.C. §371 as a United States National Phase Application of International Application No. PCT/US2005/037094 filed Oct. 13, 2005, which claims priority from U.S. Provisional Application No. 60/618,480 filed Oct. 13, 2004.

FIELD OF THE INVENTION

This invention relates to non-steroidal compounds that are modulators of androgen, glucocorticoid, mineralocorticoid, and progesterone receptors, and also to the methods for the making and use of such compounds.

BACKGROUND OF THE INVENTION

Nuclear receptors are a class of structurally related gene expression modulators that act as ligand-dependent transcription factors (R. M. Evans, *Science* 240, 889 (1988)). The steroid receptors, namely the androgen receptor, the estrogen receptor, the glucocorticoid receptor, the mineralocorticoid receptor, and the progesterone receptor represent a subclass of the nuclear receptor superfamily. Nuclear receptor ligands in this subclass exert their effects by binding to an intracellular steroid hormone receptor. After the receptor-ligand complex is translocated to the nucleus of the cell, the complex binds to recognition sites on DNA, which allows for the modulation of certain genes.

Certain substances have demonstrated the ability to exhibit their activity in a tissue selective manner. In other words, tissue selectivity allows a nuclear receptor ligand to function as an agonist in some tissues, while having no effect or even an antagonist effect in other tissues. The term "selective receptor modulator" (SRM) has been given to these molecules. A synthetic compound that binds to an intracellular receptor and mimics the effects of the native hormone is referred to as an agonist. A compound that inhibits the effect of the native hormone is called an antagonist. The term "modulators" refers to compounds that have a spectrum of activities ranging from full agonism to partial agonism to full antagonism. The molecular basis for this tissue selective activity is not completely understood. Without being limited to any particular explanation, particular ligands put nuclear receptors in different conformational states. These states dictate the ability of coactivators, corepressors, and other proteins to be recruited by the nuclear receptor ("NR"). The unique cofactor-NR ensembles are the gene transcription factors that are thought to modulate tissue selective effects.

Ligand-mediated effects through the action of nuclear receptors are not limited to the classical genotropic mechanism outlined above. It is thought that some, if not all, of the separation of anabolic and general homeostatic effects from the stimulation of sexual tissues can be explained by a particular ligand's ability to potentiate non-genotropic pathways. One example of liganded nuclear receptor induction of non-genotropic pathways is found in the work of S. C. Manolagas et al., *Cell,* 104, 719-730. The action of a sex steroid NR on osteoblasts and other cell types is shown to involve the Src/Shc/ERK signaling pathway. This activity is mediated through the ligand binding domain of the sex steroid nuclear receptor alone. The NR DNA-binding domain is not required to attenuate etoposide-induced apoptosis in HeLa cells. An NR lacking the DNA binding domain cannot function in the classical mode, acting as a transcription factor.

Nuclear receptor steroid ligands are known to play important roles in the health of both men and women. In regard to men's health, testosterone (T) and dihydrotestosterone (DHT), for example, are endogenous steroidal ligands for the androgen receptor that likely play a role in every tissue type found in the mammalian body. During the development of the fetus, androgens play a role in sexual differentiation and development of male sexual organs. Further sexual development is mediated by androgens during puberty. Androgens play diverse roles in the adult including stimulation and maintenance of male sexual accessory organs and maintenance of the musculoskeletal system. Cognitive function, sexuality, aggression, and mood are some of the behavioral aspects mediated by androgens. Androgens affect the skin, bone, and skeletal muscle, as well as blood lipids and blood cells.

The study of androgen action and male reproductive dysfunction continues to expand significantly. In fact, only recently has the definition of a disease state been associated with hormonal changes that occur in aging men. This syndrome, previously referred to as Andropause, has more recently been described as Androgen Deficiency in the Aging Male, or "ADAM" (A. Morales and J. L. Tenover, *Urologic Clinics of North America* (2002 November) 29(4) 975.) The onset of ADAM is unpredictable and its manifestations are subtle and variable. Clinical manifestations of ADAM include fatigue, depression, decreased libido, erectile dysfunction as well as changes in cognition and mood.

Published information indicates that androgen replacement therapy (ART) in men may have benefits in terms of improving body composition parameters (e.g. bone mineral density, increasing muscle mass, and strength) as well as improving libido and mood in some men. Therefore, andrologists and other specialists are increasingly using ART for the treatment of the symptoms of ADAM—though there is due caution given androgens', like testosterone, potential side effects. Nonetheless, there is increasing scientific rational of and evidence for androgen deficiency and treatment in the aging male. Current testosterone-based ART therapies include injections, skin patches, gel-based formulations, and oral preparations. All of these therapies are somewhat efficacious in the treatment of ADAM, but, due to the dramatic fluctuations in plasma T-levels following treatment, success with these therapies has been variable.

Testosterone replacement products, such as AndroGel® (1% testosterone gel CIII, marketed by Solvay Pharmaceuticals) are emerging as a treatment of choice among physicians. Such products, however, fail to correctly mimic physiological testosterone levels and have potential side effects including exacerbation of pre-existing sleep apnoea, polycythemia, and/or gynaecomastia. Furthermore, the longer-term side effects on target organs such as the prostate or the cardiovascular system are yet to be fully elucidated. Importantly, the potential carcinogenic effects of testosterone on the prostate prevent many physicians from prescribing it to older men (i.e. age >60 years) who, ironically, stand to benefit most from treatment. Also, all of the existing treatment options have fundamental problems with their delivery mechanism. The need for a novel selective androgen receptor modulator (SARM) is obviated by the potential side effect profile manifested in conventional treatments. A SARM would ideally have all the beneficial effects of endogenous androgens, while sparing sexual accessory organs, specifically the prostate.

In regard to female health, progesterone, the endogenous ligand for the progesterone receptor ("PR"), plays an important role in female reproduction during the various stages of the ovarian cycle and during pregnancy. Among other things, progesterone prepares the endometrium for implantation, regulates the implantation process, and helps maintain pregnancy. The therapeutic use of synthetic versions of progesterone (progestins) stems from progesterone's ability to regulate endometrial proliferation. In fact, progestins are included as part of hormone replacement therapy ("HRT") in women to reduce the incidence of endometriosis. Unfortunately, the effectiveness of therapy is tempered by undesired side-effect profiles. Chronic progestin therapy or continuous estrogen replacement regimens are often associated with increased bleeding. Excessive stimulatory effects on the endometrial vasculature may result in proliferation and fragility.

Compounds that modulate the effects of progesterone binding to PR are believed useful in the treatment and/or prophylaxis of endometriosis and uterine fibroid processes. Progesterone receptor antagonists such as mifepristone, also known as RU-486, and other PR modulators can inhibit endometrial proliferation at high estradiol concentrations in primates. Human clinical data with mifepristone supports the efficacy of a PR antagonist in endometriosis (D. R. Grow et. al., *J. Clin. Endocrin. Metab.* 1996, 81). Despite enthusiasm for its use, RU-486 also acts as a potent ligand for the glucocorticoid receptor ("GR"). This cross-reactivity with the GR is associated with homeostatic imbalances.

Thus, modulators of nuclear steroid hormones that are highly specific for one receptor could offer greater benefit with less side effects in the treatment of both female and male related hormone responsive diseases.

SUMMARY OF INVENTION

The present invention includes compounds of formula (I):

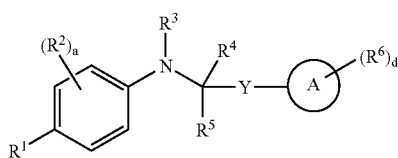

(I)

and salts, solvates, and physiologically functional derivatives thereof, wherein
$R^1$ is CN or $NO_2$;
a is 0, 1, or 2;
each $R^2$ independently is cyano, nitro, halogen, haloalkyl, alkyl, alkenyl, alkynyl, hydroxy, alkoxy, haloalkoxy, —OC(O)$R^{11}$, or aryl;
$R^3$ is —$(R^x)_f R^7$;
f is 0 or 1;
$R^x$ is a $C_1$-$C_4$ alkylene chain;
$R^7$ is H, alkyl, cycloalkyl, haloalkyl, or, when f is 1, alkoxycarbonyl;
each $R^4$ and $R^5$ independently is H, alkyl, cycloalkyl, halogen, haloalkyl, or hydroxy; or
$R^4$ and $R^5$ may combine with the carbon atom from which they are substituted to form a 3- to 7-membered ring, which ring may optionally contain one or more heteroatoms selected from O, S, and N;
Y is —$(R^y)_g$—, —$(R^y)_g O$—, —$(R^y)_g S(O)_h$—, —$(R^y)_g NR^9$—, —$(R^y)_g NR^9 C(O)$—, —$C(O)NR^9$—, —$C(O)NR^9(R^y)_g$—, —$(R^y)_g C(O)$—, and —$(R^y)_g CR^9$=$CR^9$—.

each $R^y$ is —$C(R^{13})(R^{14})$—;
each g is 1 or 2;
h is 0, 1, or 2;
each $R^{13}$ and each $R^{14}$ independently is H, alkyl, cycloalkyl, halogen, haloalkyl, or hydroxyl; or
$R^{13}$ and $R^{14}$ may combine with the carbon atom through which they are substituted to form a 3- to 7-membered ring, which ring may optionally contain one or more heteroatoms selected from O, S, or N;
A is an aryl, heteroaryl, or heterocyclyl;
d is 0, 1, 2, 3, 4, or 5;
each $R^6$ independently is alkyl, cycloalkyl, halogen, haloalkyl, hydroxy, hydroxyalkyl, hydroxyhaloalkyl, cyano, aryl, heterocyclyl, heteroaryl, —S(O)$_j R^8$, —$SO_2 NR^9 R^{10}$, —$O(R^z)_k R^{11}$, —$(R^z)_k C(O)R^8$, —$(R^z)_k C(O)OR^{12}$, —$(R^z)_k C(O)NR^9 R^{10}$, —$(R^z)_k NR^9 C(O)OR^{12}$, —$(R^z)_k NR^9 C(O)R^{12}$, —$(R^z)_k NR^9 SO_2 R^{12}$, —$NR^9 C(O)NR^9 R^{10}$, or —$NR^9 C(NR^9)NR^9 R^{10}$,
each $R^8$ is alkyl, cycloalkyl, hydroxy, or haloalkyl;
each $R^9$ and each $R^{10}$ independently is H, alkyl, cycloalkyl, or haloalkyl;
each $R^{11}$ is H, alkyl, cycloalkyl, haloalkyl, heterocyclyl, aryl, or heteroaryl;
each $R^{12}$ is H, alkyl, cycloalkyl, or haloalkyl;
each $R^z$ is a $C_1$-$C_4$ alkylene chain;
each k is 0 or 1; and
j is 0, 1, or 2.
Preferably $R^1$ is —CN.
In one embodiment a is 1 and $R^2$ is haloalkyl. Preferably $R^2$ is —$CF_3$ and is located ortho to $R^1$, where, as stated, $R^2$ preferably is —CN.
In one embodiment f is 1 and $R^x$ is $C_1$-$C_2$ alkylene. Preferably $R^x$ is methylene.
In one embodiment $R^7$ is $C_1$-$C_6$ alkyl, $C_3$-$C_6$ cycloalkyl, or $C_1$-$C_6$ haloalkyl. Preferably $R^7$ is t-butyl, cyclopropyl, or trifluoromethyl.
In one embodiment each of $R^4$ and $R^5$ are H.
In one embodiment Y is —$(R^y)_g O$—. Preferably $R^y$ is —$CH_2$— and g is 1.
In one embodiment A is aryl. Preferably aryl is phenyl.
In one embodiment A is heteroaryl. Preferably heteroaryl is indolyl, pyridyl, pyridazinyl, or pyrimidinyl.
In one embodiment d is 1 and $R^6$ is $C_1$-$C_6$ alkyl, halogen, $C_1$-$C_6$ haloalkyl, —$SO_2 R^8$, —$SO_2 NR^9 R^{10}$, —$NR^9 C(O)R^{12}$, or —$NR^9 C(O)NR^9 R^{10}$. Preferably each $R^8$ is $C_1$-$C_6$ alkyl and each occurrence of $R^9$ and $R^{10}$ are H.

The present invention includes compounds of formula IA:

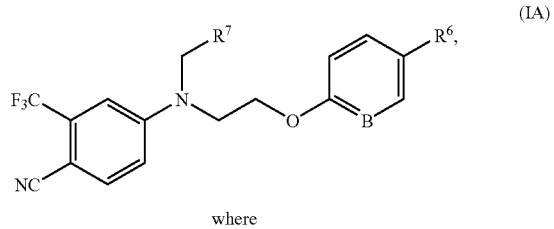

(IA)

where

| $R^7$ | B | $R^6$ |
|---|---|---|
| -Cyclopropyl | CH | —NHC(O)CH$_3$ |
| —CF$_3$ | CH | —NHC(O)CH$_3$ |
| —CF$_3$ | CH | —SO$_2$NH$_2$ |
| —CF$_3$ | CH | F |
| —CF$_3$ | CH | —NHC(O)NH$_2$ |
| —CF$_3$ | CH | —SO$_2$CH$_3$ |

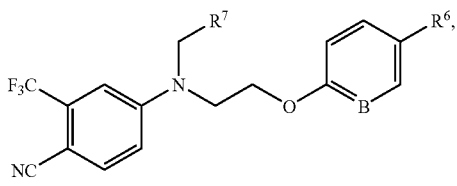

(IA)

where

| R⁷ | B | R⁶ |
|---|---|---|
| —CF₃ | CH | —CF₃ |
| t-butyl | CH | —NHC(O)CH₃ |
| t-butyl | CH | F |
| —CF₃ | N | —CF₃ |
| —CF₃ | N | —CH₃ |

The present invention also includes compounds of formula IB:

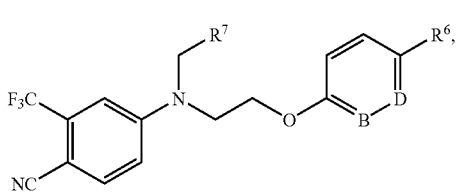

(IB)

where

| R⁷ | B | D | R⁶ |
|---|---|---|---|
| -Cyclopropyl | CH | CH | —NHC(O)CH₃ |
| —CF₃ | CH | CH | —NHC(O)CH₃ |
| —CF₃ | CH | CH | —SO₂NH₂ |
| —CF₃ | CH | CH | F |
| —CF₃ | CH | CH | —NHC(O)NH₂ |
| —CF₃ | CH | CH | —SO₂CH₃ |
| —CF₃ | CH | CH | —CF₃ |
| t-butyl | CH | CH | —NHC(O)CH₃ |
| t-butyl | CH | CH | F |
| —CF₃ | N | CH | —CF₃ |
| —CF₃ | N | CH | —CH₃ |
| t-butyl | N | CH | —CF₃ |
| t-butyl | CH | N | F |

Another aspect of the present invention includes a compound selected from:
4-[(Cyclopropylmethyl)(2-{[4-(1,1-dimethylethyl)phenyl]oxy}ethyl)amino]-2-(trifluoromethyl)benzonitrile;
N-[4-({2-[[4-Cyano-3-(trifluoromethyl)phenyl](cyclopropylmethyl)amino]ethyl}oxy)phenyl]acetamide;
4-[(Cyclopropylmethyl)(2-{[4-(methyloxy)phenyl]oxy}ethyl)amino]-2-(trifluoromethyl)benzonitrile;
4-((Cyclopropylmethyl){2-[(4-fluorophenyl)oxy]ethyl}amino)-2-(trifluoromethyl)benzonitrile;
4-[(Cyclopropylmethyl)(2-{[4-(hydroxymethyl)phenyl]oxy}ethyl)amino]-2-(trifluoromethyl)benzonitrile;
N-[4-({3-[[4-Cyano-3-(trifluoromethyl)phenyl](cyclopropylmethyl)amino]propyl}oxy)phenyl]acetamide;
4-[(Cyclopropylmethyl)(3-{[4-(1,1-dimethylethyl)phenyl]oxy}propyl)amino]-2-(trifluoromethyl)benzonitrile;
4-[(Cyclopropylmethyl)(3-{[4-(methyloxy)phenyl]oxy}propyl)amino]-2-(trifluoromethyl)benzonitrile;
4-((Cyclopropylmethyl){3-[(4-fluorophenyl)oxy]propyl}amino)-2-(trifluoromethyl)benzonitrile;
4-[(Cyclopropylmethyl)(3-{[4-(hydroxymethyl)phenyl]oxy}propyl)amino]-2-(trifluoromethyl)benzonitrile;
N-[4-({3-[[4-Cyano-3-(trifluoromethyl)phenyl](2,2,2-trifluoroethyl)amino]propyl}oxy)phenyl]acetamide;
4-[(3-{[4-(1,1-Dimethylethyl)phenyl]oxy}propyl)(2,2,2-trifluoroethyl)amino]-2-(trifluoromethyl)benzonitrile;
4-[{3-[(4-Fluorophenyl)oxy]propyl}(2,2,2-trifluoroethyl)amino]-2-(trifluoromethyl)benzonitrile;
4-[(3-{[4-(Methyloxy)phenyl]oxy}propyl)(2,2,2-trifluoroethyl)amino]-2-(trifluoromethyl)benzonitrile;
4-[{2-[(4-{[2-(1-Piperidinyl)ethyl]oxy}phenyl)oxy]ethyl}(2,2,2-trifluoroethyl)amino]-2-(trifluoromethyl)benzonitrile;
4-[(2-{[4-(Methyloxy)phenyl]oxy}ethyl)(2,2,2-trifluoroethyl)amino]-2-(trifluoromethyl)benzonitrile;
N-[4-({2-[[4-Cyano-3-(trifluoromethyl)phenyl](2,2,2-trifluoroethyl)amino]ethyl}oxy)phenyl]acetamide;
4-({2-[[4-Cyano-3-(trifluoromethyl)phenyl](2,2,2-trifluoroethyl)amino]ethyl}oxy)benzenesulfonamide;
4-[{2-[(4-Cyanophenyl)oxy]ethyl}(2,2,2-trifluoroethyl)amino]-2-(trifluoromethyl)benzonitrile;
4-[{2-[(4-Fluorophenyl)oxy]ethyl}(2,2,2-trifluoroethyl)amino]-2-(trifluoromethyl)benzonitrile;
4-[(2-{[4-(3-Oxobutyl)phenyl]oxy}ethyl)(2,2,2-trifluoroethyl)amino]-2-(trifluoromethyl)benzonitrile;
4-[[2-(1H-Indol-5-yloxy)ethyl](2,2,2-trifluoroethyl)amino]-2-(trifluoromethyl)benzonitrile;
4-[{2-[(3-Fluorophenyl)oxy]ethyl}(2,2,2-trifluoroethyl)amino]-2-(trifluoromethyl)benzonitrile;
4-[{2-[(4-Acetylphenyl)oxy]ethyl}(2,2,2-trifluoroethyl)amino]-2-(trifluoromethyl)benzonitrile;
4-[(2-{[4-(2-Oxopropyl)phenyl]oxy}ethyl)(2,2,2-trifluoroethyl)amino]-2-(trifluoromethyl)benzonitrile;
N-[3-({2-[[4-Cyano-3-(trifluoromethyl)phenyl](2,2,2-trifluoroethyl)amino]ethyl}oxy)phenyl]acetamide;
1,1-Dimethylethyl [4-({2-[[4-cyano-3-(trifluoromethyl)phenyl](2,2,2-trifluoroethyl)amino]ethyl}oxy)phenyl]carbamate;
N-[4-({2-[[4-Cyano-3-(trifluoromethyl)phenyl](2,2,2-trifluoroethyl)amino]ethyl}oxy)phenyl]methanesulfonamide;
N-[4-({2-[[4-Cyano-3-(trifluoromethyl)phenyl](2,2,2-trifluoroethyl)amino]ethyl}oxy)phenyl]urea;
4-[(2-{[4-(Methylsulfonyl)phenyl]oxy}ethyl)(2,2,2-trifluoroethyl)amino]-2-(trifluoromethyl)benzonitrile;
4-[(2,2,2-Trifluoroethyl)(2-{[4-(trifluoromethyl)phenyl]oxy}ethyl)amino]-2-(trifluoromethyl)benzonitrile;
Methyl 4-({2-[[4-cyano-3-(trifluoromethyl)phenyl](2,2,2-trifluoroethyl)amino]ethyl}oxy)benzoate;
4-({2-[[4-Cyano-3-(trifluoromethyl)phenyl](2,2,2-trifluoroethyl)amino]ethyl}oxy)benzoic acid;
4-({2-[[4-Cyano-3-(trifluoromethyl)phenyl](2,2,2-trifluoroethyl)amino]ethyl}oxy)benzamide;
1,1-Dimethylethyl {[4-({2-[[4-cyano-3-(trifluoromethyl)phenyl](2,2,2-trifluoroethyl)amino]ethyl}oxy)phenyl]methyl}carbamate;
N-[4-({2-[[4-Cyano-3-(trifluoromethyl)phenyl](2,2,2-trifluoroethyl)amino]ethyl}oxy)phenyl]guanidine trifluoroacetate;
4-[(2-{[4-(Trifluoroacetyl)phenyl]oxy}ethyl)(2,2,2-trifluoroethyl)amino]-2-(trifluoromethyl)benzonitrile;
4-{(2,2,2-Trifluoroethyl)[2-({4-[2,2,2-trifluoro-1-hydroxy-1-(trifluoromethyl)ethyl]phenyl}oxy)ethyl]amino}-2-(trifluoromethyl)benzonitrile;
4-[(2-{[4-(2-Oxo-1-pyrrolidinyl)phenyl]oxy}ethyl)(2,2,2-trifluoroethyl)amino]-2-(trifluoromethyl)benzonitrile;

4-[(2-{[4-(1,3-Thiazol-2-yl)phenyl]oxy}ethyl)(2,2,2-trifluoroethyl)amino]-2-(trifluoromethyl)benzonitrile;
4-[(2-{[4-(1,3-Oxazol-2-yl)phenyl]oxy}ethyl)(2,2,2-trifluoroethyl)amino]-2-(trifluoromethyl)benzonitrile;
4-[{2-[(2-Oxo-1,2,3,4-tetrahydro-6-quinolinyl)oxy]ethyl}(2,2,2-trifluoroethyl)amino]-2-(trifluoromethyl)benzonitrile;
4-[[2-(2-Pyridinyloxy)ethyl](2,2,2-trifluoroethyl)amino]-2-(trifluoromethyl)benzonitrile;
4-[[2-(3-Pyridinyloxy)ethyl](2,2,2-trifluoroethyl)amino]-2-(trifluoromethyl)benzonitrile;
4-[[2-(4-Pyridinyloxy)ethyl](2,2,2-trifluoroethyl)amino]-2-(trifluoromethyl)benzonitrile;
4-[(2,2,2-Trifluoroethyl)(2-{[5-(trifluoromethyl)-2-pyridinyl]oxy}ethyl)amino]-2-(trifluoromethyl)benzonitrile;
4-[{2-[(5-Methyl-2-pyridinyl)oxy]ethyl}(2,2,2-trifluoroethyl)amino]-2-(trifluoromethyl)benzonitrile;
4-[{2-[(6-Chloro-3-pyridinyl)oxy]ethyl}(2,2,2-trifluoroethyl)amino]-2-(trifluoromethyl)benzonitrile;
4-[{2-[(6-Methyl-3-pyridinyl)oxy]ethyl}(2,2,2-trifluoroethyl)amino]-2-(trifluoromethyl)benzonitrile;
4-[{2-[(5-Bromo-2-pyridinyl)oxy]ethyl}(2,2,2-trifluoroethyl)amino]-2-(trifluoromethyl)benzonitrile;
4-[{2-[(6-Fluoro-3-pyridinyl)oxy]ethyl}(2,2,2-trifluoroethyl)amino]-2-(trifluoromethyl)benzonitrile;
4-[{2-[(5-Fluoro-2-pyridinyl)oxy]ethyl}(2,2,2-trifluoroethyl)amino]-2-(trifluoromethyl)benzonitrile;
N-[6-({2-[[4-Cyano-3-(trifluoromethyl)phenyl](2,2,2-trifluoroethyl)amino]ethyl}oxy)-3-pyridinyl]acetamide;
4-[{2-[(6-Oxo-1,6-dihydro-3-pyridinyl)oxy]ethyl}(2,2,2-trifluoroethyl)amino]-2-(trifluoromethyl)benzonitrile;
4-[[2-(3-Pyridazinyloxy)ethyl](2,2,2-trifluoroethyl)amino]-2-(trifluoromethyl)benzonitrile;
4-[[2-(4-Pyrimidinyloxy)ethyl](2,2,2-trifluoroethyl)amino]-2-(trifluoromethyl)benzonitrile;
N-[4-({3-[[4-Cyano-3-(trifluoromethyl)phenyl](2,2-dimethylpropyl)amino]propyl}oxy)phenyl]acetamide;
4-[(3-{[4-(1,1-Dimethylethyl)phenyl]oxy}propyl)(2,2-dimethylpropyl)amino]-2-(trifluoromethyl)benzonitrile;
4-((2,2-Dimethylpropyl){3-[(4-fluorophenyl)oxy]propyl}amino)-2-(trifluoromethyl)benzonitrile;
4-[(2,2-Dimethylpropyl)(3-{[4-(methyloxy)phenyl]oxy}propyl)amino]-2-(trifluoromethyl)benzonitrile;
N-[4-({2-[[4-Cyano-3-(trifluoromethyl)phenyl](2,2-dimethylpropyl)amino]ethyl}oxy)phenyl]acetamide;
4-({2-[[4-Cyano-3-(trifluoromethyl)phenyl](2,2-dimethylpropyl)amino]ethyl}oxy)benzenesulfonamide;
4-((2,2-Dimethylpropyl){2-[(4-fluorophenyl)oxy]ethyl}amino)-2-(trifluoromethyl)benzonitrile;
4-[{2-[(4-Acetylphenyl)oxy]ethyl}(2,2-dimethylpropyl)amino]-2-(trifluoromethyl)benzonitrile;
4-{(2,2-Dimethylpropyl)[2-(phenyloxy)ethyl]amino}-2-(trifluoromethyl)benzonitrile;
4-[(2,2-Dimethylpropyl)(2-{[4-(methylsulfonyl)phenyl]oxy}ethyl)amino]-2-(trifluoromethyl)benzonitrile;
4-((2,2-Dimethylpropyl){2-[(5-fluoro-2-pyridinyl)oxy]ethyl}amino)-2-(trifluoromethyl)benzonitrile;
4-((2,2-Dimethylpropyl){2-[(6-fluoro-3-pyridinyl)oxy]ethyl}amino)-2-(trifluoromethyl)benzonitrile;
4-[(2,2-Dimethylpropyl)(2-{[5-(trifluoromethyl)-2-pyridinyl]oxy}ethyl)amino]-2-(trifluoromethyl)benzonitrile;
N-[4-({2-[[4-Cyano-2-(trifluoromethyl)phenyl](2,2,2-trifluoroethyl)amino]ethyl}oxy)phenyl]acetamide;
4-[{2-[(4-Fluorophenyl)oxy]ethyl}(2,2,2-trifluoroethyl)amino]-3-(trifluoromethyl)benzonitrile;
4-[{2-[(4-Acetylphenyl)oxy]ethyl}(2,2,2-trifluoroethyl)amino]-3-(trifluoromethyl)benzonitrile;
4-[[2-(Phenylthio)ethyl](2,2,2-trifluoroethyl)amino]-2-(trifluoromethyl)benzonitrile;
N-[4-({2-[[4-Cyano-3-(trifluoromethyl)phenyl](2,2,2-trifluoroethyl)amino]ethyl}thio)phenyl]acetamide;
N-[4-({2-[[4-Cyano-3-(trifluoromethyl)phenyl](2,2,2-trifluoroethyl)amino]ethyl}thio)phenyl]-N-methylacetamide;
4-[[2-(Phenylsulfinyl)ethyl](2,2,2-trifluoroethyl)amino]-2-(trifluoromethyl)benzonitrile;
N-[4-({2-[[4-Cyano-3-(trifluoromethyl)phenyl](2,2,2-trifluoroethyl)amino]ethyl}sulfinyl)phenyl]acetamide;
4-[[2-(Phenylsulfonyl)ethyl](2,2,2-trifluoroethyl)amino]-2-(trifluoromethyl)benzonitrile;
N-[4-({2-[[4-Cyano-3-(trifluoromethyl)phenyl](2,2,2-trifluoroethyl)amino]ethyl}sulfonyl)phenyl]acetamide;
N-[4-({2-[[4-Cyano-3-(trifluoromethyl)phenyl](2,2,2-trifluoroethyl)amino]ethyl}thio)phenyl]methanesulfonamide;
4-[[2-(Pyrimidin-2-ylamino)ethyl](2,2,2-trifluoroethyl)amino]-2-(trifluoromethyl)benzonitrile;
4-[{2-[Methyl(pyrimidin-2-yl)amino]ethyl}(2,2,2-trifluoroethyl)amino]-2-(trifluoromethyl)benzonitrile;
N-{2-[[4-Cyano-3-(trifluoromethyl)phenyl](2,2,2-trifluoroethyl)amino]ethyl}benzamide;
4-[[3-(4-Fluorophenyl)propyl](2,2,2-trifluoroethyl)amino]-2-(trifluoromethyl)benzonitrile;
N-(4-{3-[[4-Cyano-3-(trifluoromethyl)phenyl](2,2,2-trifluoroethyl)amino]propyl}phenyl)acetamide;
4-[(3-Phenylpropyl)(2,2,2-trifluoroethyl)amino]-2-(trifluoromethyl)benzonitrile;
4-[[3-(3-Pyridinyl)propyl](2,2,2-trifluoroethyl)amino]-2-(trifluoromethyl)benzonitrile trifluoroacetate;
N-(4-{3-[[4-Cyano-3-(trifluoromethyl)phenyl](2,2-dimethylpropyl)amino]propyl}phenyl)acetamide;
1,1-Dimethylethyl N-{3-[4-(acetylamino)phenyl]propyl}-N-[4-cyano-3-(trifluoromethyl)phenyl]glycinate;
1,1-Dimethylethyl N-[4-cyano-3-(trifluoromethyl)phenyl]-N-(2-{[4-(methyloxy)phenyl]oxy}ethyl)glycinate;
$N^2$-[4-Cyano-3-(trifluoromethyl)phenyl]-$N^2$-ethyl-$N^1$-(4-fluorophenyl)glycinamide;
$N^2$-[4-Cyano-3-(trifluoromethyl)phenyl]-$N^2$-ethyl-$N^1$-(phenylmethyl)glycinamide;
$N^2$-[4-Cyano-3-(trifluoromethyl)phenyl]-$N^2$-ethyl-$N^1$-[(4-fluorophenyl)methyl]glycinamide;
$N^2$-[4-Cyano-3-(trifluoromethyl)phenyl]-$N^2$-ethyl-$N^1$-[(1S)-1-phenylethyl]glycinamide;
$N^2$-[4-Cyano-3-(trifluoromethyl)phenyl]-$N^2$-ethyl-$N^1$-[(1R)-1-phenylethyl]glycinamide;
$N^2$-[4-Cyano-3-(trifluoromethyl)phenyl]-$N^1$-phenyl-NA-propylglycinamide;
$N^2$-[4-Cyano-3-(trifluoromethyl)phenyl]-$N^1$-(4-fluorophenyl)-$N^2$-propylglycinamide;
$N^2$-[4-Cyano-3-(trifluoromethyl)phenyl]-$N^1$-(phenylmethyl)-$N^2$-propylglycinamide;
$N^2$-[4-Cyano-3-(trifluoromethyl)phenyl]-$N^1$-[(4-fluorophenyl)methyl]-$N^2$-propylglycinamide;
$N^2$-[4-Cyano-3-(trifluoromethyl)phenyl]-$N^1$-[(1R)-1-phenylethyl]-$N^2$-propylglycinamide;
$N^2$-[4-Cyano-3-(trifluoromethyl)phenyl]-$N^1$-[(1S)-1-phenylethyl]-$N^2$-propylglycinamide;
$N^2$-[4-Cyano-3-(trifluoromethyl)phenyl]-$N^1$-[2-(4-fluorophenyl)ethyl]-$N^2$-propylglycinamide;
$N^2$-[4-Cyano-3-(trifluoromethyl)phenyl]-$N^2$-(cyclopropylmethyl)-$N^1$-phenylglycinamide;
$N^2$-[4-Cyano-3-(trifluoromethyl)phenyl]-$N^2$-(cyclopropylmethyl)-$N^1$-(4-fluorophenyl)glycinamide;

N²-[4-Cyano-3-(trifluoromethyl)phenyl]-N²-(cyclopropylmethyl)-N¹-(phenylmethyl)glycinamide;
N²-[4-Cyano-3-(trifluoromethyl)phenyl]-N²-(cyclopropylmethyl)-N¹-[(4-fluorophenyl)methyl]glycinamide;
N²-[4-Cyano-3-(trifluoromethyl)phenyl]-N²-(cyclopropylmethyl)-N¹-[(1S)-1-phenylethyl]glycinamide;
N²-[4-Cyano-3-(trifluoromethyl)phenyl]-N²-(cyclopropylmethyl)-N¹-[(1R)-1-phenylethyl]glycinamide;
N²-[4-Cyano-3-(trifluoromethyl)phenyl]-N²-(cyclopropylmethyl)-N¹-(2-phenylethyl)glycinamide;
N²-[4-Cyano-3-(trifluoromethyl)phenyl]-N²-(cyclopropylmethyl)-N¹-[2-(4-fluorophenyl)ethyl]glycinamide;
N²-[4-Cyano-3-(trifluoromethyl)phenyl]-N²-(cyclopropylmethyl)-N¹-phenylalaninamide;
N²-[4-Cyano-3-(trifluoromethyl)phenyl]-N²-(cyclopropylmethyl)-N¹-(4-fluorophenyl)alaninamide;
N²-[4-Cyano-3-(trifluoromethyl)phenyl]-N²-(2-methylpropyl)-N¹-phenylglycinamide;
N²-[4-Cyano-3-(trifluoromethyl)phenyl]-N¹-(4-fluorophenyl)-N²-(2-methylpropyl)glycinamide;
N²-[4-Cyano-3-(trifluoromethyl)phenyl]-N¹-phenyl-N²-(2,2,2-trifluoroethyl)glycinamide;
N²-[4-Cyano-3-(trifluoromethyl)phenyl]-N¹-(4-fluorophenyl)-N²-(2,2,2-trifluoroethyl)glycinamide;
N¹-[4-(Acetylamino)phenyl]-N²-[4-cyano-3-(trifluoromethyl)phenyl]-N²-(2,2,2-trifluoroethyl)glycinamide;
N²-[4-Cyano-3-(trifluoromethyl)phenyl]-N¹-(2-phenylethyl)-N²-(2,2,2-trifluoroethyl)glycinamide;
2-[[4-Cyano-3-(trifluoromethyl)phenyl](2,2,2-trifluoroethyl)amino]-N-phenylbutanamide;
2-[[4-Cyano-3-(trifluoromethyl)phenyl](2,2,2-trifluoroethyl)amino]-N-(4-fluorophenyl)butanamide;
4-[[2-(1H-1,2,4-Triazol-1-yl)ethyl](2,2,2-trifluoroethyl)amino]-2-(trifluoromethyl)benzonitrile;
4-[(2-Phenylethyl)(propyl)amino]-2-(trifluoromethyl)benzonitrile;
N-(Cyclopropylmethyl)-N-[2-(4-morpholinyl)ethyl]-4-nitro-3-(trifluoromethyl)aniline trifluoroacetate;
4-{(Cyclopropylmethyl)[2-(4-morpholinyl)ethyl]amino}-2-(trifluoromethyl)benzonitrile trifluoroacetate;
4-{(Cyclopropylmethyl)[2-(1-piperidinyl)ethyl]amino}-3-(trifluoromethyl)benzonitrile trifluoroacetate;
4-[[2-(1-Pyrrolidinyl)ethyl](2,2,2-trifluoroethyl)amino]-2-(trifluoromethyl)benzonitrile trifluoroacetate;

and salts, solvates, and pharmaceutically functional derivatives thereof.

Another aspect of the present invention includes a compound substantially as hereinbefore defined with reference to any one of the Examples.

Another aspect of the present invention includes a pharmaceutical composition comprising a compound of the present invention and a pharmaceutically acceptable carrier.

Another aspect of the present invention includes a compound of the present invention for use as an active therapeutic substance.

Another aspect of the present invention includes a compound of the present invention for use in the treatment or prophylaxis of conditions or disorders that respond to selective androgen receptor modulation.

Another aspect of the present invention includes a compound of the present invention for use in the treatment or prophylaxis of osteoporosis, muscle wasting, frailty, cardiovascular disease, breast cancer, uterine cancer, prostate hyperplasia, prostate cancer, dyslipidemia, menopausal vasomotor conditions, urinary incontinence, artherosclerosis, libido enhancement, depression, uterine fibroid disease, aortic smooth muscle cell proliferation, endometriosis, or ADAM.

Another aspect of the present invention includes the use of a compound of the present invention in the manufacture of a medicament for use in the treatment or prophylaxis of conditions or disorders that respond to selective androgen receptor modulation.

Another aspect of the present invention includes using a compound according to the present invention in the manufacture of a medicament for use in the treatment or prophylaxis of osteoporosis, muscle wasting, frailty, cardiovascular disease, breast cancer, uterine cancer, prostatic hyperplasia, prostate cancer, dyslipidemia, menopausal vasomotor conditions, urinary incontinence, artherosclerosis, libido enhancement, depression, uterine fibroid disease, aortic smooth muscle cell proliferation, endometriosis, or ADAM.

Another aspect of the present invention includes a method for the treatment or prophylaxis of conditions or disorders that respond to selective androgen receptor modulation comprising the administration of a compound according to the present invention.

Another aspect of the present invention includes a method for the treatment or prophylaxis of osteoporosis, muscle wasting, frailty, cardiovascular disease, breast cancer, uterine cancer, prostatic hyperplasia, prostate cancer, dyslipidemia, menopausal vasomotor conditions, urinary incontinence, artherosclerosis, libido enhancement, depression, uterine fibroid disease, aortic smooth muscle cell proliferation, endometriosis, or ADAM comprising the administration of a compound according to the present invention.

The compounds of the present invention are believed to modulate the function of one or more nuclear hormone receptor(s). Particularly, the compounds of the present invention modulate the androgen receptor ("AR"). The present invention includes compounds that are selective agonists, partial agonists, antagonists, or partial antagonists of the AR. Compounds of the present invention are useful in the treatment of AR-associated diseases and conditions, for example, a disease or condition that is prevented, alleviated, or cured through the modulation of the function or activity of AR. Such modulation may be isolated within certain tissues or widespread throughout the body of the subject being treated.

An aspect of the present invention is the use of the compounds of the present invention for the treatment or prophylaxis of a variety of disorders including, but not limited to, osteoporosis and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), dry eye, sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, menopausal vasomotor conditions, urinary incontinence, artherosclerosis, libido enhancement, sexual dysfunction, depression, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, aortic smooth muscle cell proliferation, male hormone replacement, or ADAM.

DETAILED DESCRIPTION OF THE PREFERRED EMBODIMENT

Terms are used within their accepted meanings. The following definitions are meant to clarify, but not limit, the terms defined.

As used herein the term "alkyl" refers to a straight or branched chain hydrocarbon, preferably having from one to twelve carbon atoms. Examples of "alkyl" as used herein include, but are not limited to, methyl, ethyl, propyl, isopropyl, isobutyl, n-butyl, tert-butyl, isopentyl, and n-pentyl.

As used throughout this specification, the preferred number of atoms, such as carbon atoms, will be represented by, for example, the phrase "$C_x$-$C_y$ alkyl," which refers to an alkyl group, as herein defined, containing the specified number of carbon atoms. Similar terminology will apply for other preferred terms and ranges as well.

As used herein the term "alkenyl" refers to a straight or branched chain aliphatic hydrocarbon containing one or more carbon-to-carbon double bonds. Examples include, but are not limited to, vinyl and the like.

As used herein the term "alkynyl" refers to a straight or branched chain aliphatic hydrocarbon containing one or more carbon-to-carbon triple bonds. Examples include, but are not limited to, ethynyl and the like.

As used herein, the term "alkylene" refers to a straight or branched chain divalent hydrocarbon radical, preferably having from one to ten carbon atoms. Alkylene groups as defined herein optionally may be substituted with, for example, an alkyl group. Examples of "alkylene" as used herein include, but are not limited to, methylene ($-CH_2-$), ethylene ($-CH_2-CH_2-$), and substituted versions thereof such as ($-CH(CH_3)-$) and the like.

As used herein, the term "cycloalkyl" refers to an optionally substituted non-aromatic cyclic hydrocarbon ring. Exemplary "cycloalkyl" groups include, but are not limited to, cyclopropyl, cyclobutyl, cyclopentyl, cyclohexyl, cycloheptyl, and the like.

As used herein, the term "heterocycle" or "heterocyclyl" refers to a mono- or poly-cyclic ring system containing one or more heteroatoms and optionally containing one or more degrees of unsaturation. Preferred heteroatoms include N, O, and/or S, including N-oxides, sulfur oxides, and dioxides. Preferably the ring is three to ten-membered and is saturated. Such rings may be optionally fused to one or more of another "heterocyclic" ring(s), heteroaryl ring(s), aryl ring(s), or cycloalkyl ring(s). Examples of "heterocyclic" groups include, but are not limited to, tetrahydrofuran, pyran, piperidine, pyrrolidine, pyrrolidinone, morpholine, tetrahydrothiopyran, tetrahydrothiophene, and 3,4-dihydro-2(1H)-quinolinone.

As used herein, the term "aryl" refers to a benzene ring or to a fused benzene ring system, for example anthracene, phenanthrene, or naphthalene ring systems. Examples of "aryl" groups include, but are not limited to, phenyl, 2-naphthyl, 1-naphthyl, biphenyl, and substituted derivatives thereof. One preferred aryl group is phenyl.

As used herein, the term "heteroaryl" refers to a monocyclic five to seven membered aromatic ring, or to a fused bicyclic aromatic ring system comprising two of such aromatic rings, which contain one or more nitrogen, sulfur, and/or oxygen atoms, where N-oxides, sulfur oxides, and dioxides are permissible heteroatom substitutions. Examples of "heteroaryl" groups used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof. Preferred heteroaryl groups include indolyl, pyridyl, pyrimidinyl, and pyridazinyl.

As used herein the term "halogen" refers to fluorine, chlorine, bromine, or iodine.

As used herein the term "haloalkyl" refers to an alkyl group, as defined herein that is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, e.g., fluoro, chloro, bromo, and iodo. The term "haloalkyl" should be interpreted to include such substituents such as $-CF_3$, $-CH_2-CH_2-F$, $-CH_2-CF_3$, and the like.

As used herein the term "hydroxy" or "hydroxyl" refers to the group $-OH$.

As used herein the term "hydroxyalkyl" refers to an alkyl group, as defined herein, which is substituted with a hydroxyl group. Examples include $-CH_2-OH$, $-C(CH_3)_2-OH$, and the like.

As used herein the term "hydroxyhaloalkyl" refers to a haloalkyl group, as defined herein, which is substituted with a hydroxyl group. Examples include $-C(CF_3)_2-OH$ and the like.

As used herein the term "mercapto" refers to the group $-SH$.

As used herein the term "alkoxy" refers to the group $-OR_a$, where $R_a$ is alkyl as defined above.

As used herein the term "aryloxy" refers to the group $-OR_b$, where $R_b$ is aryl as defined above.

As used herein the term "nitro" refers to the group $-NO_2$.

As used herein the term "cyano" refers to the group $-CN$.

As used herein the term "amino" refers to the group $-NH_2$, and "substituted amino" refers to a group $-N(R_a)(R_b)$, where one of $R_a$ and $R_b$ are other than H. For example, "substituted amino" includes the groups $-N(CH_3)(CH_3)$, $-N(CH_3)(CH_2-CH_3)$, and the like.

As used herein throughout the present specification, the phrase "optionally substituted" or variations thereof denote an optional substitution, including multiple degrees of substitution, with one or more substituent group. The phrase should not be interpreted so as to be imprecise or duplicative of substitution patterns herein described or depicted specifically. Rather, those of ordinary skill in the art will appreciate that the phrase is included to provide for obvious modifications, which are encompassed within the scope of the appended claims.

The compounds of the present invention may crystallize in more than one form, a characteristic known as polymorphism, and such polymorphic forms ("polymorphs") are within the scope of the present invention. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by formula (I), as well as any wholly or partially equilibrated mixtures thereof. The present invention also includes the individual isomers of the compounds represented by the formulas above as mixtures with isomers thereof in which one or more chiral centers are inverted.

Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. Representative salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teociate, tosylate, triethiodide, trimethylammonium, and valerate salts. Other salts, which are not pharmaceutically acceptable, may be useful in the preparation of compounds of this invention and these should be considered to form a further aspect of the invention.

As used herein, the term "solvate" refers to a complex of variable stoichiometry formed by a solute (in this invention, a compound of Formula I, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry And Drug Discovery*, 5$^{th}$ Edition, Vol 1: Principles and Practice, which is incorporated herein by reference to the extent that it teaches physiologically functional derivatives.

As used herein, the term "effective amount" means that amount of a drug or pharmaceutical agent that will elicit the biological or medical response of a tissue, system, animal, or human that is being sought, for instance, by a researcher or clinician. The biological or medical response may be considered a prophylactic response or a treatment response. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of the present invention, as well as salts, solvates, and physiological functional derivatives thereof, may be administered as the raw chemical. Additionally, the active ingredient may be presented as a pharmaceutical composition.

Accordingly, the invention further provides pharmaceutical compositions that include effective amounts of compounds of the present invention and salts, solvates, and physiological functional derivatives thereof, and one or more pharmaceutically acceptable carriers, diluents, or excipients. The compounds of the present invention and salts, solvates, and physiologically functional derivatives thereof, are as herein described. The carrier(s), diluent(s) or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a compound of the present invention or salts, solvates, and physiological functional derivatives thereof, with one or more pharmaceutically acceptable carriers, diluents or excipients.

A therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. Regardless, an effective amount of a compound of the present invention for the treatment of humans suffering from frailty, generally, should be in the range of 0.1 to 100 mg/kg body weight of recipient (mammal) per day. More usually the effective amount should be in the range of 0.1 to 10 mg/kg body weight per day. Thus, for a 70 kg adult mammal the actual amount per day would usually be from 7 to 700 mg. This amount may be given in a single dose per day or in a number (such as two, three, four, five, or more) of sub-doses per day such that the total daily dose is the same. An effective amount of a salt, solvate, or physiologically functional derivative thereof, may be determined as a proportion of the effective amount of the compound of the present invention per se. Similar dosages should be appropriate for treatment or prophylaxis of the other conditions referred to herein.

Pharmaceutical formulations may be presented in unit dose forms containing a predetermined amount of active ingredient per unit dose. Such a unit may contain, as a non-limiting example, 0.5 mg to 1 g of a compound of the present invention, depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules may be made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets may be formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention and salts, solvates, and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of the present invention and salts, solvates, and physiologically functional derivatives thereof may also be delivered by the use of monoclonal antibodies as individual carriers to which the compound molecules are coupled.

The compounds may also be coupled with soluble polymers as targetable drug carriers. Such polymers can include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

The compounds of the present invention and their salts, solvates, and physiologically functional derivatives thereof, may be employed alone or in combination with other therapeutic agents for the treatment of the above-mentioned conditions. For example, in frailty therapy, combination may be had with other anabolic or osteoporosis therapeutic agents. As one example, osteoporosis combination therapies according to the present invention would thus comprise the administration of at least one compound of the present invention or a salt, solvate, or physiologically functional derivative thereof, and the use of at least one other osteoporosis therapy. As a further example, combination therapies according to the present invention include the administration of at least one compound of the present invention or a salt, solvate, or physiologically functional derivative thereof, and at least one other osteoporosis treatment agent, for example, an anti-bone resorption agent. The compound(s) of the present invention and the other pharmaceutically active agent(s) may be administered together or separately and, when administered separately, administration may occur simultaneously or sequentially, in any order. The amounts of the compound(s) of the present invention and the other pharmaceutically active agent(s) and the relative timings of administration will be selected in order to achieve the desired combined therapeutic effect. The administration in combination of a compound of the present invention salts, solvates, or physiologically functional derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

Another potential osteoporosis treatment agent is a bone building (anabolic) agent. Bone building agents can lead to increases in parameters such as bone mineral density that are greater than those than can be achieved with anti-resorptive agents. In some cases, such anabolic agents can increase trabecular connectivity leading to greater structural integrity of the bone.

Other potential therapeutic combinations include the compounds of the present invention combined with other compounds of the present invention, growth promoting agents, growth hormone secretagogues, growth hormone releasing factor and its analogs, growth hormone and its analogs, somatomedins, alpha-adrenergic agonists, serotonin 5-HT$_D$ agonists, agents that inhibit somatostatin or its release, 5-α-reductase inhibitors, aromatase inhibitors, GnRH agonists or antagonists, parathyroid hormone, bisphosphonates, estrogen, testosterone, SERMs, progesterone receptor agonists or antagonists, and/or with other modulators of nuclear hormone receptors.

One skilled in the art will acknowledge that although the compounds embodied herein will be used as selective agonists, partial agonists, and antagonists, compounds with mixed steroid activities may also be employed.

The compounds of the present invention may be used in the treatment of a variety of disorders and conditions and, as such, the compounds of the present invention may be used in combination with a variety of other suitable therapeutic agents useful in the treatment or prophylaxis of those disorders or conditions. Non-limiting examples include combinations of the present invention with anti-diabetic agents, anti-osteoporosis agents, anti-obesity agents, anti-inflammatory agents, anti-anxiety agents, anti-depressants, anti-hypertensive agents, anti-platelet agents, anti-thrombotic and thrombolytic agents, cardiac glycosides, cholesterol or lipid lowering agents, mineralocorticoid receptor antagonists, phosphodiesterase inhibitors, kinase inhibitors, thyroid mimetics, anabolic agents, viral therapies, cognitive disorder therapies, sleeping disorder therapies, sexual dysfunction therapies, contraceptives, cytotoxic agents, radiation therapy, anti-proliferative agents, and anti-tumor agents. Additionally, the compounds of the present invention may be combined with nutritional supplements such as amino acids, triglycerides, vitamins, minerals, creatine, piloic acid, carnitine, or coenzyme Q10.

An aspect of the present invention is the use of the compounds of the present invention for the treatment or prophylaxis of a variety of disorders including, but not limited to, osteoporosis and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), dry eye, sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, menopausal vasomotor conditions, urinary incontinence, artherosclerosis, libido enhancement, sexual dysfunction, depression, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, aortic smooth muscle cell proliferation, male hormone replacement, or ADAM.

In particular, the compounds of the present invention are believed useful, either alone or in combination with other agents, in the treatment of and use as male and female hormone replacement therapy, hypogonadism, osteoporosis, muscle wasting, wasting diseases, cancer cachexia, frailty, prostatic hyperplasia, prostate cancer, breast cancer, menopausal and andropausal vasomotor conditions, urinary incontinence, sexual dysfunction, erectile dysfunction, depression, uterine fibroid disease, and/or endometriosis, treatment of acne, hirsutism, stimulation of hematopoiesis, male contraception, impotence, and as anabolic agents.

Another aspect of the present invention thus also provides compounds of the present invention and salts, solvates, or physiologically functional derivatives thereof, for use in medical therapy. Particularly, the present invention provides for the treatment or prophylaxis of disorders mediated by androgenic activity. More particularly, the present invention provides through the treatment or prophylaxis of disorders responsive to tissue-selective anabolic and or androgenic activity. A further aspect of the invention provides a method of treatment or prophylaxis of a mammal suffering from a disorder mediated by androgenic activity, which includes administering to said subject an effective amount of a compound of the present invention or a salt, solvate, or physiologically functional derivative thereof.

A further aspect of the invention provides a method of treatment or prophylaxis of a mammal requiring the treatment or prophylaxis of a variety of disorders including, but not limited to, osteoporosis and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), dry eye, sarcopenia, chronic fatigue syndrome, chronic myaligia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, menopausal vasomotor conditions, urinary incontinence, artherosclerosis, libido enhancement, sexual dysfunction, depression, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, aortic smooth muscle cell proliferation, male hormone replacement, or ADAM. Preferably the compounds of the present invention are used as male and female hormone replacement therapy or for the treatment or prevention of hypogonadism, osteoporosis, muscle wasting, wasting diseases, cancer cachexia, frailty, prostatic hyperplasia, prostate cancer, breast cancer, menopausal and andropausal vasomotor conditions, urinary incontinence, sexual dysfunction, erectile dysfunction, depression, uterine fibroid disease, and/or endometriosis, treatment of acne, hirsutism, stimulation of hematopoiesis, male contraception, impotence, and as anabolic agents, which use includes administering to a subject an effective amount of a compound of the present invention or a salt, solvate, or physiologically functional derivative thereof. The mammal requiring treatment with a compound of the present invention is typically a human being.

The compounds of this invention may be made by a variety of methods, including well-known standard synthetic methods. Illustrative general synthetic methods are set out below and then specific compounds of the invention are prepared in the working Examples.

In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention.

Those skilled in the art will recognize if a stereocenter exists in compounds of the present invention. Accordingly, the present invention includes all possible stereoisomers and includes not only racemic compounds but the individual enantiomers as well. When a compound is desired as a single enantiomer, such may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994), incorporated by reference with regard to stereochemistry.

Representative AR modulator compounds, agonists, partial agonists, and antagonists according to the current invention include:

Another aspect of the present invention includes a compound selected from:

4-[(Cyclopropylmethyl)(2-{[4-(1,1-dimethylethyl)phenyl]oxy}ethyl)amino]-2-(trifluoromethyl)benzonitrile;

N-[4-({2-[[4-Cyano-3-(trifluoromethyl)phenyl](cyclopropylmethyl)amino]ethyl}oxy)phenyl]acetamide;

4-[(Cyclopropylmethyl)(2-{[4-(methyloxy)phenyl]oxy}ethyl)amino]-2-(trifluoromethyl)benzonitrile;

4-((Cyclopropylmethyl){2-[(4-fluorophenyl)oxy]
ethyl}amino)-2-(trifluoromethyl)benzonitrile;

4-[(Cyclopropylmethyl)(2-{[4-(hydroxymethyl)phenyl]
oxy}ethyl)amino]-2-(trifluoromethyl)benzonitrile;

N-[4-({3-[[4-Cyano-3-(trifluoromethyl)phenyl](cyclopropylmethyl)amino]propyl}oxy)phenyl]acetamide;

4-[(Cyclopropylmethyl)(3-{[4-(1,1-dimethylethyl)phenyl]
oxy}propyl)amino]-2-(trifluoromethyl)benzonitrile;

4-[(Cyclopropylmethyl)(3-{[4-(methyloxy)phenyl]
oxy}propyl)amino]-2-(trifluoromethyl)benzonitrile;

4-((Cyclopropylmethyl){3-[(4-fluorophenyl)oxy]
propyl}amino)-2-(trifluoromethyl)benzonitrile;

4-[(Cyclopropylmethyl)(3-{[4-(hydroxymethyl)phenyl]
oxy}propyl)amino]-2-(trifluoromethyl)benzonitrile;

N-[4-({3-[[4-Cyano-3-(trifluoromethyl)phenyl](2,2,2-trifluoroethyl)amino]propyl}oxy)phenyl]acetamide;

4-[(3-{[4-(1,1-Dimethylethyl)phenyl]oxy}propyl)(2,2,2-trifluoroethyl)amino]-2-(trifluoromethyl)benzonitrile;

4-[{3-[(4-Fluorophenyl)oxy]propyl}(2,2,2-trifluoroethyl)
amino]-2-(trifluoromethyl)benzonitrile;

4-[(3-{[4-(Methyloxy)phenyl]oxy}propyl)(2,2,2-trifluoroethyl)amino]-2-(trifluoromethyl)benzonitrile;

4-[{2-[(4-{[2-(1-Piperidinyl)ethyl]oxy}phenyl)oxy]ethyl}
(2,2,2-trifluoroethyl)amino]-2-(trifluoromethyl)benzonitrile;

4-[(2-{[4-(Methyloxy)phenyl]oxy}ethyl)(2,2,2-trifluoroethyl)amino]-2-(trifluoromethyl)benzonitrile;

N-[4-({2-[[4-Cyano-3-(trifluoromethyl)phenyl](2,2,2-trifluoroethyl)amino]ethyl}oxy)phenyl]acetamide;

4-({2-[[4-Cyano-3-(trifluoromethyl)phenyl](2,2,2-trifluoroethyl)amino]ethyl}oxy)benzenesulfonamide;

4-[{2-[(4-Cyanophenyl)oxy]ethyl}(2,2,2-trifluoroethyl)
amino]-2-(trifluoromethyl)benzonitrile;

4-[{2-[(4-Fluorophenyl)oxy]ethyl}(2,2,2-trifluoroethyl)
amino]-2-(trifluoromethyl)benzonitrile;

4-[(2-{[4-(3-Oxobutyl)phenyl]oxy}ethyl)(2,2,2-trifluoroethyl)amino]-2-(trifluoromethyl)benzonitrile;

4-[[2-(1H-Indol-5-yloxy)ethyl](2,2,2-trifluoroethyl)amino]-2-(trifluoromethyl)benzonitrile;

4-[{2-[(3-Fluorophenyl)oxy]ethyl}(2,2,2-trifluoroethyl)
amino]-2-(trifluoromethyl)benzonitrile;

4-[{2-[(4-Acetylphenyl)oxy]ethyl}(2,2,2-trifluoroethyl)
amino]-2-(trifluoromethyl)benzonitrile;

4-[(2-{[4-(2-Oxopropyl)phenyl]oxy}ethyl)(2,2,2-trifluoroethyl)amino]-2-(trifluoromethyl)benzonitrile;

N-[3-({2-[[4-Cyano-3-(trifluoromethyl)phenyl](2,2,2-trifluoroethyl)amino]ethyl}oxy)phenyl]acetamide;

1,1-Dimethylethyl [4-({2-[[4-cyano-3-(trifluoromethyl)phenyl](2,2,2-trifluoroethyl)amino]ethyl}oxy)phenyl]carbamate;

N-[4-({2-[[4-Cyano-3-(trifluoromethyl)phenyl](2,2,2-trifluoroethyl)amino]ethyl}oxy)phenyl]methanesulfonamide;

N-[4-({2-[[4-Cyano-3-(trifluoromethyl)phenyl](2,2,2-trifluoroethyl)amino]ethyl}oxy)phenyl]urea;

4-[(2-{[4-(Methylsulfonyl)phenyl]oxy}ethyl)(2,2,2-trifluoroethyl)amino]-2-(trifluoromethyl)benzonitrile;

4-[(2,2,2-Trifluoroethyl)(2-{[4-(trifluoromethyl)phenyl]
oxy}ethyl)amino]-2-(trifluoromethyl)benzonitrile;

Methyl 4-({2-[[4-cyano-3-(trifluoromethyl)phenyl](2,2,2-trifluoroethyl)amino]ethyl}oxy)benzoate;

4-({2-[[4-Cyano-3-(trifluoromethyl)phenyl](2,2,2-trifluoroethyl)amino]ethyl}oxy)benzoic acid;

4-({2-[[4-Cyano-3-(trifluoromethyl)phenyl](2,2,2-trifluoroethyl)amino]ethyl}oxy)benzamide;

1,1-Dimethylethyl {[4-({2-[[4-cyano-3-(trifluoromethyl)
phenyl](2,2,2-trifluoroethyl)amino]ethyl}oxy)phenyl]
methyl}carbamate;

N-[4-({2-[[4-Cyano-3-(trifluoromethyl)phenyl](2,2,2-trifluoroethyl)amino]ethyl}oxy)phenyl]guanidine trifluoroacetate;

4-[(2-{[4-(Trifluoroacetyl)phenyl]oxy}ethyl)(2,2,2-trifluoroethyl)amino]-2-(trifluoromethyl)benzonitrile;

4-{(2,2,2-Trifluoroethyl)[2-({4-[2,2,2-trifluoro-1-hydroxy-1-(trifluoromethyl)ethyl]phenyl}oxy)ethyl]amino}-2-(trifluoromethyl)benzonitrile;

4-[(2-{[4-(2-Oxo-1-pyrrolidinyl)phenyl]oxy}ethyl)(2,2,2-trifluoroethyl)amino]-2-(trifluoromethyl)benzonitrile;

4-[(2-{[4-(1,3-Thiazol-2-yl)phenyl]oxy}ethyl)(2,2,2-trifluoroethyl)amino]-2-(trifluoromethyl)benzonitrile;

4-[(2-{[4-(1,3-Oxazol-2-yl)phenyl]oxy}ethyl)(2,2,2-trifluoroethyl)amino]-2-(trifluoromethyl)benzonitrile;

4-[{2-[(2-Oxo-1,2,3,4-tetrahydro-6-quinolinyl)oxy]ethyl}
(2,2,2-trifluoroethyl)amino]-2-(trifluoromethyl)benzonitrile;

4-[[2-(2-Pyridinyloxy)ethyl](2,2,2-trifluoroethyl)amino]-2-(trifluoromethyl)benzonitrile;

4-[[2-(3-Pyridinyloxy)ethyl](2,2,2-trifluoroethyl)amino]-2-(trifluoromethyl)benzonitrile;

4-[[2-(4-Pyridinyloxy)ethyl](2,2,2-trifluoroethyl)amino]-2-(trifluoromethyl)benzonitrile;

4-[(2,2,2-Trifluoroethyl)(2-{[5-(trifluoromethyl)-2-pyridinyl]oxy}ethyl)amino]-2-(trifluoromethyl)benzonitrile;

4-[{2-[(5-Methyl-2-pyridinyl)oxy]ethyl}(2,2,2-trifluoroethyl)amino]-2-(trifluoromethyl)benzonitrile;

4-[{2-[(6-Chloro-3-pyridinyl)oxy]ethyl}(2,2,2-trifluoroethyl)amino]-2-(trifluoromethyl)benzonitrile;

4-[{2-[(6-Methyl-3-pyridinyl)oxy]ethyl}(2,2,2-trifluoroethyl)amino]-2-(trifluoromethyl)benzonitrile;

4-[{2-[(5-Bromo-2-pyridinyl)oxy]ethyl}(2,2,2-trifluoroethyl)amino]-2-(trifluoromethyl)benzonitrile;

4-[{2-[(6-Fluoro-3-pyridinyl)oxy]ethyl}(2,2,2-trifluoroethyl)amino]-2-(trifluoromethyl)benzonitrile;

4-[{2-[(5-Fluoro-2-pyridinyl)oxy]ethyl}(2,2,2-trifluoroethyl)amino]-2-(trifluoromethyl)benzonitrile;

N-[6-({2-[[4-Cyano-3-(trifluoromethyl)phenyl](2,2,2-trifluoroethyl)amino]ethyl}oxy)-3-pyridinyl]acetamide;

4-[{2-[(6-Oxo-1,6-dihydro-3-pyridinyl)oxy]ethyl}(2,2,2-trifluoroethyl)amino]-2-(trifluoromethyl)benzonitrile;

4-[[2-(3-Pyridazinyloxy)ethyl](2,2,2-trifluoroethyl)amino]-2-(trifluoromethyl)benzonitrile;

4-[[2-(4-Pyrimidinyloxy)ethyl](2,2,2-trifluoroethyl)amino]-2-(trifluoromethyl)benzonitrile;

N-[4-({3-[[4-Cyano-3-(trifluoromethyl)phenyl](2,2-dimethylpropyl)amino]propyl}oxy)phenyl]acetamide;

4-[(3-{[4-(1,1-Dimethylethyl)phenyl]oxy}propyl)(2,2-dimethylpropyl)amino]-2-(trifluoromethyl)benzonitrile;

4-((2,2-Dimethylpropyl){3-[(4-fluorophenyl)oxy]
propyl}amino)-2-(trifluoromethyl)benzonitrile;

4-[(2,2-Dimethylpropyl)(3-{[4-(methyloxy)phenyl]
oxy}propyl)amino]-2-(trifluoromethyl)benzonitrile;

N-[4-({2-[[4-Cyano-3-(trifluoromethyl)phenyl](2,2-dimethylpropyl)amino]ethyl}oxy)phenyl]acetamide;

4-({2-[[4-Cyano-3-(trifluoromethyl)phenyl](2,2-dimethylpropyl)amino]ethyl}oxy)benzenesulfonamide;

4-((2,2-Dimethylpropyl){2-[(4-fluorophenyl)oxy]
ethyl}amino)-2-(trifluoromethyl)benzonitrile;

4-[{2-[(4-Acetylphenyl)oxy]ethyl}(2,2-dimethylpropyl)
amino]-2-(trifluoromethyl)benzonitrile;

4-{(2,2-Dimethylpropyl)[2-(phenyloxy)ethyl]amino}-2-(trifluoromethyl)benzonitrile;

4-[(2,2-Dimethylpropyl)(2-{[4-(methylsulfonyl)phenyl]oxy}ethyl)amino]-2-(trifluoromethyl)benzonitrile;
4-((2,2-Dimethylpropyl){2-[(5-fluoro-2-pyridinyl)oxy]ethyl}amino)-2-(trifluoromethyl)benzonitrile;
4-((2,2-Dimethylpropyl){2-[(6-fluoro-3-pyridinyl)oxy]ethyl}amino)-2-(trifluoromethyl)benzonitrile;
4-[(2,2-Dimethylpropyl)(2-{[5-(trifluoromethyl)-2-pyridinyl]oxy}ethyl)amino]-2-(trifluoromethyl)benzonitrile;
N-[4-({2-[[4-Cyano-2-(trifluoromethyl)phenyl](2,2,2-trifluoroethyl)amino]ethyl}oxy)phenyl]acetamide;
4-[{2-[(4-Fluorophenyl)oxy]ethyl}(2,2,2-trifluoroethyl)amino]-3-(trifluoromethyl)benzonitrile;
4-[{2-[(4-Acetylphenyl)oxy]ethyl}(2,2,2-trifluoroethyl)amino]-3-(trifluoromethyl)benzonitrile;
4-[[2-(Phenylthio)ethyl](2,2,2-trifluoroethyl)amino]-2-(trifluoromethyl)benzonitrile;
N-[4-({2-[[4-Cyano-3-(trifluoromethyl)phenyl](2,2,2-trifluoroethyl)amino]ethyl}thio)phenyl]acetamide;
N-[4-({2-[[4-Cyano-3-(trifluoromethyl)phenyl](2,2,2-trifluoroethyl)amino]ethyl}thio)phenyl]-N-methylacetamide;
4-[[2-(Phenylsulfinyl)ethyl](2,2,2-trifluoroethyl)amino]-2-(trifluoromethyl)benzonitrile;
N-[4-({2-[[4-Cyano-3-(trifluoromethyl)phenyl](2,2,2-trifluoroethyl)amino]ethyl}sulfinyl)phenyl]acetamide;
4-[[2-(Phenylsulfonyl)ethyl](2,2,2-trifluoroethyl)amino]-2-(trifluoromethyl)benzonitrile;
N-[4-({2-[[4-Cyano-3-(trifluoromethyl)phenyl](2,2,2-trifluoroethyl)amino]ethyl}sulfonyl)phenyl]acetamide;
N-[4-({2-[[4-Cyano-3-(trifluoromethyl)phenyl](2,2,2-trifluoroethyl)amino]ethyl}thio)phenyl]methanesulfonamide;
4-[[2-(Pyrimidin-2-ylamino)ethyl](2,2,2-trifluoroethyl)amino]-2-(trifluoromethyl)benzonitrile;
4-[{2-[Methyl(pyrimidin-2-yl)amino]ethyl}(2,2,2-trifluoroethyl)amino]-2-(trifluoromethyl)benzonitrile;
N-{2-[[4-Cyano-3-(trifluoromethyl)phenyl](2,2,2-trifluoroethyl)amino]ethyl}benzamide;
4-[[3-(4-Fluorophenyl)propyl](2,2,2-trifluoroethyl)amino]-2-(trifluoromethyl)benzonitrile;
N-(4-{3-[[4-Cyano-3-(trifluoromethyl)phenyl](2,2,2-trifluoroethyl)amino]propyl}phenyl)acetamide;
4-[(3-Phenylpropyl)(2,2,2-trifluoroethyl)amino]-2-(trifluoromethyl)benzonitrile;
4-[[3-(3-Pyridinyl)propyl](2,2,2-trifluoroethyl)amino]-2-(trifluoromethyl)benzonitrile trifluoroacetate;
N-(4-{3-[[4-Cyano-3-(trifluoromethyl)phenyl](2,2-dimethylpropyl)amino]propyl}phenyl)acetamide;
1,1-Dimethylethyl N-{3-[4-(acetylamino)phenyl]propyl}-N-[4-cyano-3-(trifluoromethyl)phenyl]glycinate;
1,1-Dimethylethyl N-[4-cyano-3-(trifluoromethyl)phenyl]-N-(2-{[4-(methyloxy)phenyl]oxy}ethyl)glycinate;
$N^2$-[4-Cyano-3-(trifluoromethyl)phenyl]-$N^2$-ethyl-$N^1$-(4-fluorophenyl)glycinamide;
$N^2$-[4-Cyano-3-(trifluoromethyl)phenyl]-$N^2$-ethyl-$N^1$-(phenylmethyl)glycinamide;
$N^2$-[4-Cyano-3-(trifluoromethyl)phenyl]-$N^2$-ethyl-$N^1$-[(4-fluorophenyl)methyl]glycinamide;
$N^2$-[4-Cyano-3-(trifluoromethyl)phenyl]-$N^2$-ethyl-$N^1$-[(1S)-1-phenylethyl]glycinamide;
$N^2$-[4-Cyano-3-(trifluoromethyl)phenyl]-$N^2$-ethyl-$N^1$-[(1R)-1-phenylethyl]glycinamide;
$N^2$-[4-Cyano-3-(trifluoromethyl)phenyl]-$N^1$-phenyl-$N^2$-propylglycinamide;
$N^2$-[4-Cyano-3-(trifluoromethyl)phenyl]-$N^1$-(4-fluorophenyl)-$N^2$-propylglycinamide;
$N^2$-[4-Cyano-3-(trifluoromethyl)phenyl]-$N^1$-(phenylmethyl)-$N^2$-propylglycinamide;
$N^2$-[4-Cyano-3-(trifluoromethyl)phenyl]-$N^1$-[(4-fluorophenyl)methyl]-$N^2$-propylglycinamide;
$N^2$-[4-Cyano-3-(trifluoromethyl)phenyl]-$N^1$-[(1R)-1-phenylethyl]-$N^2$-propylglycinamide;
$N^2$-[4-Cyano-3-(trifluoromethyl)phenyl]-$N^1$-[(1S)-1-phenylethyl]-$N^2$-propylglycinamide;
$N^2$-[4-Cyano-3-(trifluoromethyl)phenyl]-$N^1$-[(2-(4-fluorophenyl)ethyl]-$N^2$-propylglycinamide;
$N^2$-[4-Cyano-3-(trifluoromethyl)phenyl]-$N^2$-(cyclopropylmethyl)-$N^1$-phenylglycinamide;
$N^2$-[4-Cyano-3-(trifluoromethyl)phenyl]-$N^2$-(cyclopropylmethyl)-$N^1$-(4-fluorophenyl)glycinamide;
$N^2$-[4-Cyano-3-(trifluoromethyl)phenyl]-$N^2$-(cyclopropylmethyl)-$N^1$-(phenylmethyl)glycinamide;
$N^2$-[4-Cyano-3-(trifluoromethyl)phenyl]-$N^2$-(cyclopropylmethyl)-$N^1$-[(4-fluorophenyl)methyl]glycinamide;
$N^2$-[4-Cyano-3-(trifluoromethyl)phenyl]-$N^2$-(cyclopropylmethyl)-$N^1$-[(1S)-1-phenylethyl]glycinamide;
$N^2$-[4-Cyano-3-(trifluoromethyl)phenyl]-$N^2$-(cyclopropylmethyl)-$N^1$-[(1R)-1-phenylethyl]glycinamide;
$N^2$-[4-Cyano-3-(trifluoromethyl)phenyl]-$N^2$-(cyclopropylmethyl)-$N^1$-(2-phenylethyl)glycinamide;
$N^2$-[4-Cyano-3-(trifluoromethyl)phenyl]-$N^2$-(cyclopropylmethyl)-$N^1$-[2-(4-fluorophenyl)ethyl]glycinamide;
$N^2$-[4-Cyano-3-(trifluoromethyl)phenyl]-$N^2$-(cyclopropylmethyl)-$N^1$-phenylalaninamide;
$N^2$-[4-Cyano-3-(trifluoromethyl)phenyl]-$N^2$-(cyclopropylmethyl)-$N^1$-(4-fluorophenyl)alaninamide;
$N^2$-[4-Cyano-3-(trifluoromethyl)phenyl]-$N^2$-(2-methylpropyl)-$N^1$-phenylglycinamide;
$N^2$-[4-Cyano-3-(trifluoromethyl)phenyl]-$N^2$-(4-fluorophenyl)-$N^1$-(2-methylpropyl)glycinamide;
$N^2$-[4-Cyano-3-(trifluoromethyl)phenyl]-$N^1$-phenyl-$N^2$-(2,2,2-trifluoroethyl)glycinamide;
$N^2$-[4-Cyano-3-(trifluoromethyl)phenyl]-$N^1$-(4-fluorophenyl)-$N^2$-(2,2,2-trifluoroethyl)glycinamide;
$N^1$-[4-(Acetylamino)phenyl]-$N^2$-[4-cyano-3-(trifluoromethyl)phenyl]-$N^2$-(2,2,2-trifluoroethyl)glycinamide;
$N^2$-[4-Cyano-3-(trifluoromethyl)phenyl]-$N^1$-(2-phenylethyl)-$N^2$-(2,2,2-trifluoroethyl)glycinamide;
2-[[4-Cyano-3-(trifluoromethyl)phenyl](2,2,2-trifluoroethyl)amino]-N-phenylbutanamide;
2-[[4-Cyano-3-(trifluoromethyl)phenyl](2,2,2-trifluoroethyl)amino]-N-(4-fluorophenyl)butanamide;
4-[[2-(1H-1,2,4-Triazol-1-yl)ethyl](2,2,2-trifluoroethyl)amino]-2-(trifluoromethyl)benzonitrile;
4-[(2-Phenylethyl)(propyl)amino]-2-(trifluoromethyl)benzonitrile;
N-(Cyclopropylmethyl)-N-[2-(4-morpholinyl)ethyl]-4-nitro-3-(trifluoromethyl)aniline trifluoroacetate;
4-{(Cyclopropylmethyl)[2-(4-morpholinyl)ethyl]amino}-2-(trifluoromethyl)benzonitrile trifluoroacetate;
4-{(Cyclopropylmethyl)[2-(1-piperidinyl)ethyl]amino}-3-(trifluoromethyl)benzonitrile trifluoroacetate;
4-[[2-(1-Pyrrolidinyl)ethyl](2,2,2-trifluoroethyl)amino]-2-(trifluoromethyl)benzonitrile trifluoroacetate;
and salts, solvates, and pharmaceutically functional derivatives thereof.

ABBREVIATIONS

As used herein the symbols and conventions used in these processes, schemes and examples are consistent with those used in the contemporary scientific literature, for example, the *Journal of the American Chemical Society* or the *Journal* of Biological Chemistry. Specifically, the following abbreviations may be used in the examples and throughout the specification:

| | |
|---|---|
| g (grams); | mg (milligrams); |
| L (liters); | mL (milliliters); |
| μL (microliters); | psi (pounds per square inch); |
| M (molar); | mM (millimolar); |
| Hz (Hertz); | MHz (megahertz); |
| mol (moles); | mmol (millimoles); |
| rt (room temperature); | min (min); |
| h (h); | mp (melting point); |
| TLC (thin layer chromatography); | $CH_2Cl_2$ (methylene chloride); |
| $t_R$ (retention time); | RP (reverse phase); |
| TEA (triethylamine); | TFA (trifluoroacetic acid); |
| TFAA (trifluoroacetic anhydride); | THF (tetrahydrofuran); |
| $CDCl_3$ (deuterated chloroform); | $CD_3OD$ (deuterated methanol); |
| $SiO_2$ (silica); | DMSO (dimethylsulfoxide); |
| EtOAc (ethyl acetate); | atm (atmosphere); |
| HCl (hydrochloric acid); | $CHCl_3$ (chloroform); |
| DMF (N,N-dimethylformamide); | Ac (acetyl); |
| $Cs_2CO_3$ (cesium carbonate); | Me (methyl); |
| Et (ethyl); | EtOH (ethanol); |
| MeOH (methanol); | t-Bu (tert-butyl); |
| PPTS (pyridinium p-toluenesulfonate); | $N_2$ (nitrogen); |
| DME (1,2-dimethoxyethane); | DBAD (dibenzyl azodicarboxylate); |
| ADDP (1,1'-(azodicarbonyl)dipiperidine); | CsF (cesium fluoride); |
| NMO (4-methylmorpholine N-oxide); | sat'd (saturated); |
| 9-BBN (9-borabicyclo[3.3.1]nonyl); | DCC (1,3-dicyclohexylcarbodiimide); |
| MsCl (methanesulphonyl chloride); | Ac (acetyl group); |
| KOAc (potassium carbonate); | CBz (benzyloxy carbonyl). |
| BOC (tert-butoxycarbonyl group); | |
| Ps (polymer supported); | |

Unless otherwise indicated, all temperatures are expressed in ° C. (degrees Centigrade). All reactions conducted under an inert atmosphere at room temperature unless otherwise noted.

$^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or b (broad).

Scheme 1

Method 1A

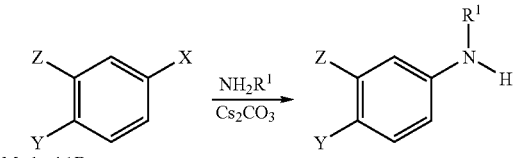

Method 1B

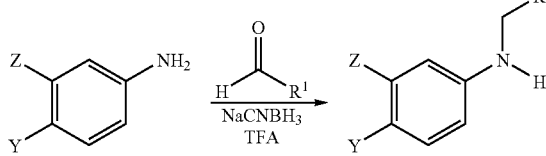

X = F, Cl, Br, OTf, etc.
Y = CN, $NO_2$
Z = $CF_3$, halogen, etc.

Secondary anilines used for the synthesis of compounds of formula (I) can be prepared by two different methods (illustrated in Scheme 1). As exemplified by Method 1A, electron deficient arenes are treated with primary amines, a non-limiting example is 1-cyclopropylmethanamine, in the presence of a base, a non-limiting example of which is cesium carbonate, to afford the corresponding aniline. Method 1B illustrates a second method of synthesizing secondary anilines by reductive alkylation of primary anilines using aldehydes or hydrates, a non-limiting example of which is trifluoroacetaldehyde hydrate, and reducing agents, a non-limiting example of which is sodium cyanoborohydride, in the presence of acid, such as TFA.

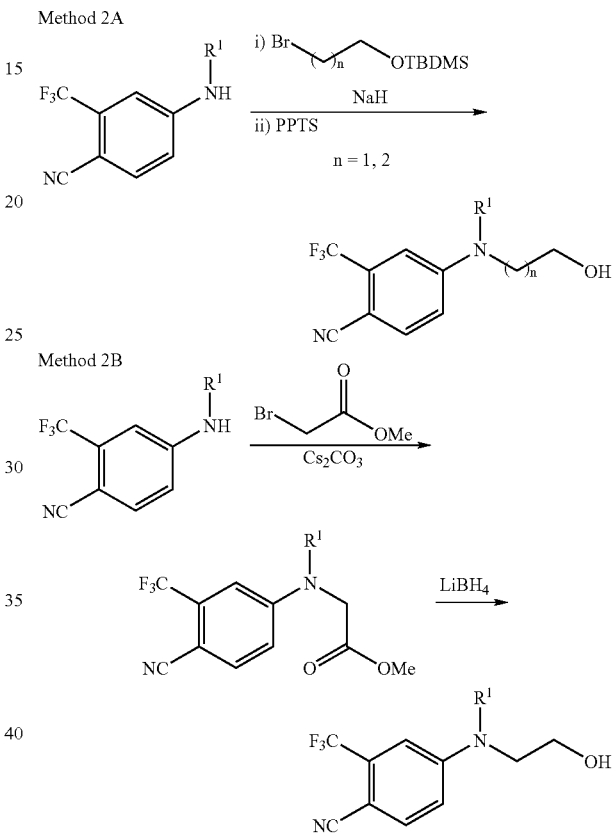

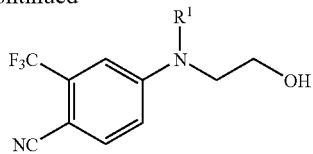

The secondary anilines of Scheme 1 can be further elaborated by alkylation with reagents that afford alcohol intermediates (Scheme 2). The corresponding alkylated products were converted to the desired alcohol intermediates by three different methods. Method 2A utilizes protected halo alcohols for example [(2-bromoethyl)oxy](1,1-dimethylethyl)dimethylsilane with subsequent cleavage of the silylether to afford the corresponding alcohol. Alkylation with α-halo esters followed by reduction with lithium borohydride also affords alcohols (Method 2B). In the case where $R^1$ is a bulky substituent such as neopentyl, alkylation with allyl bromide and subsequent oxidative cleavage affords good conversion to two carbon-linked alcohols (Method 2C).

Scheme 3

Method 3A

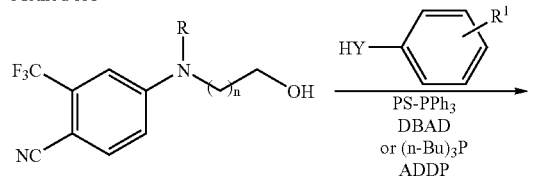

Method 3B

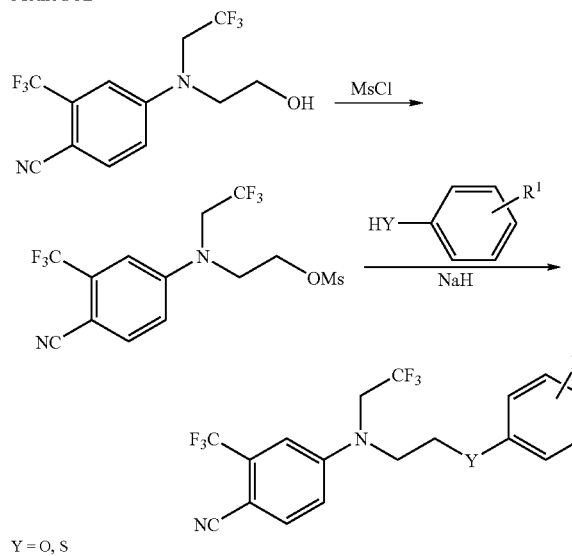

Y = O, S

The alcohols of Scheme 2 were converted to compounds of Formula (I) by two general methods: Mitsunobu coupling and displacement of a mesylate (Scheme 3). As exemplified in Method 3A, alcohol precursors can be treated with reagents such as polymer supported triphenyl phosphine in the presence of DBAD and a phenol or thiophenol to afford aryl ethers. Another method (Method 3B) to form aryl ethers is through conversion of the alcohol precursors to the corresponding mesylate and subsequent displacement with a phenol or thiophenol.

Scheme 4

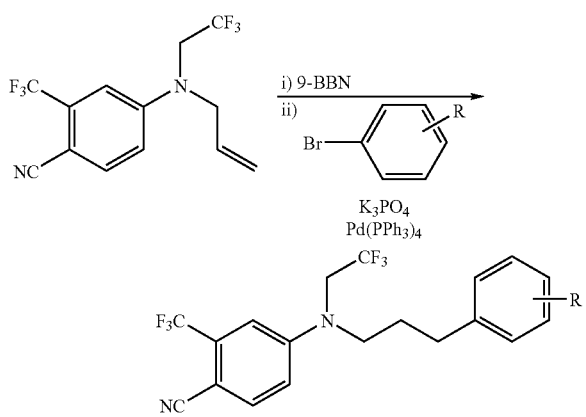

All carbon linked compounds of Formula (I) start from allyl anilines. Hydroboration affords alkyl boranes that are then subjected to Suzuki coupling with aryl halides (Scheme 4).

Scheme 5

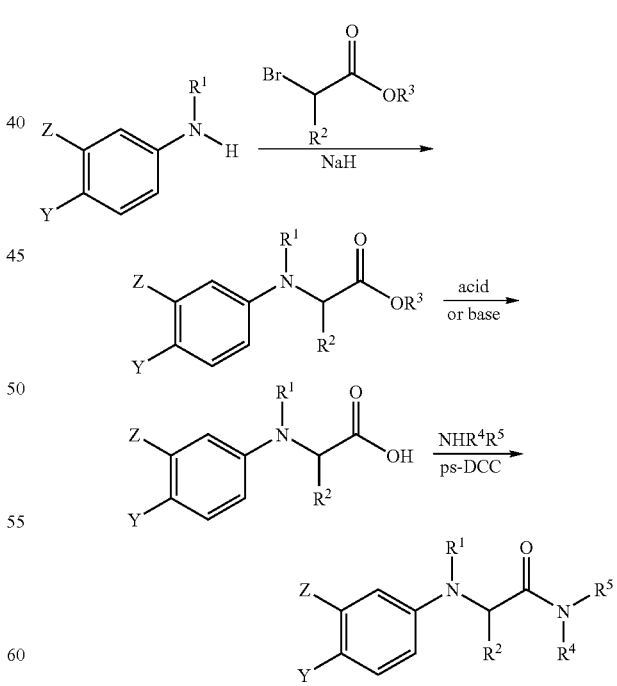

Y = CN, $NO_2$
Z = $CF_3$, halogen, etc.

Synthesis of amide containing compounds of Formula (I) was accomplished by alkylation of secondary anilines with α-haloesters, a non-limiting example of which is t-butylbromo acetate (Scheme 5). Deprotection with acid or saponification with base affords the corresponding carboxylic acid, which is then coupled with amines in the presence of polymer-supported DCC.

EXAMPLES

Example 1

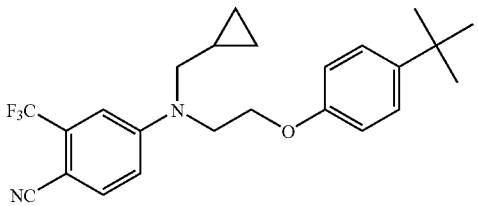

4-[(Cyclopropylmethyl)(2-{[4-(1,1-dimethylethyl)phenyl]oxy}ethyl)amino]-2-(trifluoromethyl)benzonitrile

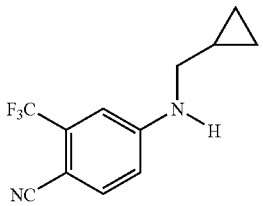

A. 4-[(Cyclopropylmethyl)amino]-2-(trifluoromethyl)benzonitrile

A mixture of 4-fluoro-2-(trifluoromethyl)benzonitrile (9.45 g, 50 mmol), 1-cyclopropylmethanamine (5.0 g, 70 mmol), and potassium carbonate (10 g) was stirred for 12 h in acetonitrile (50 mL) at 55° C. The mixture was cooled to 20° C., filtered, and the filter-cake was washed with acetonitrile (3×25 mL). The filtrate was concentrated under vacuum to obtain 11.9 g (99%) of the title compound as a white solid: $^1$H NMR (400 MHz, CDCl$_3$) δ 7.53 (d, J=8.6 Hz, 1H), 6.83 (d, J=2.4 Hz, 1H), 6.65 (dd, J=8.6, 2.4 Hz, 1H), 4.62 (bs, 1H), 3.02 (d, J=7.1 Hz, 2H), 1.09 (m, 1H), 0.61 (m, 2H), 0.27 (m, 2H).

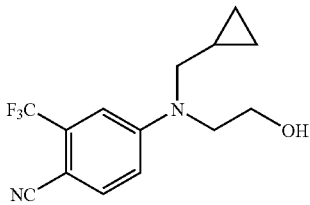

B. 4-[(Cyclopropylmethyl)(2-hydroxyethyl)amino]-2-(trifluoromethyl) benzonitrile To a slurry of hexanes-washed NaH (0.560 g of a 60% w/w suspension in mineral oil, 14 mmol) in DMF (10 mL) at 0° C. was added a solution of 4-[(cyclopropylmethyl) amino]-2-(trifluoromethyl)benzonitrile (1.68 g, 7.00 mmol) in DMF (4 mL), dropwise over 5 min. The resulting mixture was stirred 30 min at 0° C., [(2-bromoethyl)oxy](1,1-dimethylethyl)dimethylsilane (1.79 mL, 8.40 mmol) was added dropwise over 3 min, and the cooling bath was removed. After 15 h, an additional portion of NaH (0.280 g, 7.0 mmol) was added, followed by [(2-bromoethyl)oxy](1,1-dimethylethyl)dimethylsilane (1.49 mL, 7.00 mmol). After 4 h, the mixture was poured into water and extracted with Et$_2$O (×3). Combined organics were washed (water, brine), dried over Na$_2$SO$_4$, filtered, and concentrated in vacuo. The residue was purified by flash chromatography (hexanes/EtOAc), affording 1.49 g of an orange syrup. The product obtained was dissolved in EtOH (20 mL) and PPTS (1.81 g) was added. The resulting mixture was held at reflux for 4 h, cooled, and concentrated in vacuo. The residue was partitioned between EtOAc/sat'd NaHCO$_3$, the organic layer was washed (10% v/v HCl, water, brine), dried over Na$_2$SO$_4$, filtered, and concentrated in vacuo. The residue was purified by flash chromatography (EtOAc/hexanes), affording 1.16 g of the title compound as a colorless oil which slowly crystallized: $^1$H NMR (300 MHz, CDCl$_3$) δ 7.55 (d, J=8.8 Hz, 1H), 7.05 (d, J=2.3 Hz, 1H), 6.89 (dd, J=8.8, 2.6 Hz, 1H), 3.87 (bt, J=5.7 Hz, 2H), 3.67 (t, J=5.8 Hz, 2H), 3.36 (d, J=6.0 Hz, 2H), 1.78 (bs, 1H), 1.12-0.97 (m, 1H), 0.69-0.56 (m, 2H), 0.35-0.25 (m, 2H); MS (APCI) m/z 285 (M+1).

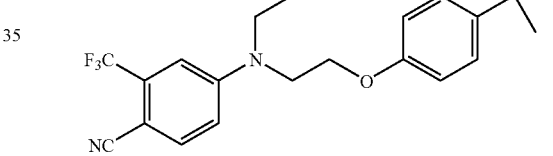

C. 4-[(Cyclopropylmethyl)(2-{[4-(1,1-dimethylethyl)phenyl]oxy}ethyl)amino]-2-(trifluoromethyl)benzonitrile To a slurry of polymer-supported triphenylphosphine (0.23 g, ca. 3 mmol/g, ca. 0.70 mmol) in CH$_2$Cl$_2$ was added 4-[(cyclopropylmethyl)(2-hydroxyethyl)amino]-2-(trifluoromethyl)benzonitrile (0.100 g, 0.35 mmol) and 4-tert-butylphenol (0.105 g, 0.70 mmol). The mixture was shaken for 10 min, a solution of DBAD (0.121 g, 0.525 mmol) in CH$_2$Cl$_2$ (0.5 mL) was added, and shaking was continued overnight. Solids were removed by filtration and the filtrate was shaken with polymer-supported carbonate (0.50 g, ca. 2.9 mmol/g, ca. 1.5 mmol CO$_3^{2-}$) for 4 h. Solids were removed by filtration, the filtrate was treated with TFA (1 mL) for 1 h and concentrated in vacuo. The residue was purified by flash chromatography (EtOAc/hexanes), affording 0.0847 g of the title compound as a colorless gum: $^1$H NMR (300 MHz, CDCl$_3$) δ 7.58 (d, J=8.8 Hz, 1H), 7.29 (app. d, J=8.8 Hz, 2H), 7.11 (d, J=2.4 Hz, 1H), 6.90 (dd, J=8.8, 2.5 Hz, 1H), 6.78 (app. d, J=8.7 Hz, 2H), 4.14 (t, J=5.8 Hz, 2H), 3.89 (t, J=5.6 Hz, 2H), 3.39 (d, J=6.2 Hz, 2H), 1.29 (s, 9H), 1.14-0.99 (m, 1H), 0.69-0.59 (m, 2H), 0.36-0.27 (m, 2H); MS (APCI) m/z 417 (M+1).

Example 2

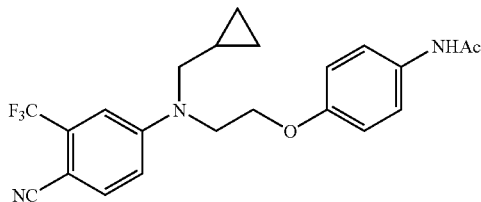

N-[4-({2-[[4-Cyano-3-(trifluoromethyl)phenyl](cyclopropylmethyl)amino]ethyl}oxy)phenyl]acetamide Synthesized as described in Example 1C from 4-[(cyclopropylmethyl)(2-hydroxyethyl)amino]-2-(trifluoromethyl)benzonitrile and 4-acetamidophenol: MS (APCI) m/z 418 (M+1).

Example 3

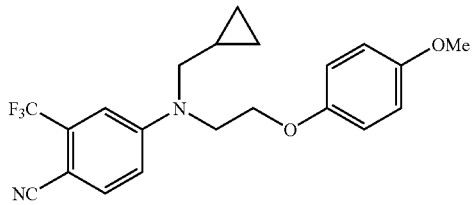

4-[(Cyclopropylmethyl)(2-{[4-(methyloxy)phenyl]oxy}ethyl)amino]-2-(trifluoromethyl)benzonitrile Synthesized as described in Example 1C from 4-[(cyclopropylmethyl)(2-hydroxyethyl)amino]-2-(trifluoromethyl)benzonitrile and 4-methoxyphenol: MS (APCI) m/z 391 (M+1).

Example 4

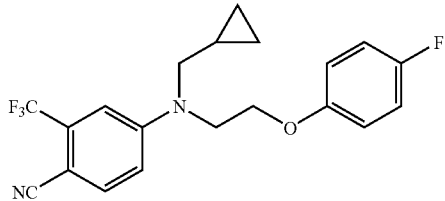

4-((Cyclopropylmethyl){2-[(4-fluorophenyl)oxy]ethyl}amino)-2-(trifluoromethyl)benzonitrile Synthesized as described in Example 1C from 4-[(cyclopropylmethyl)(2-hydroxyethyl)amino]-2-(trifluoromethyl)benzonitrile and 4-fluorophenol: MS (APCI) m/z 379 (M+1).

Example 5

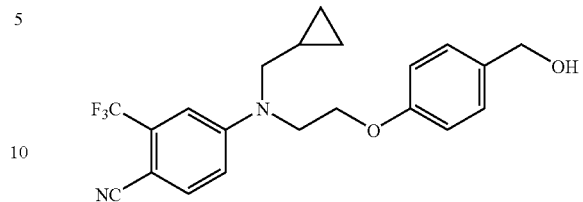

4-[(Cyclopropylmethyl)(2-{[4-(hydroxymethyl)phenyl]oxy}ethyl)amino]-2-(trifluoromethyl)benzonitrile

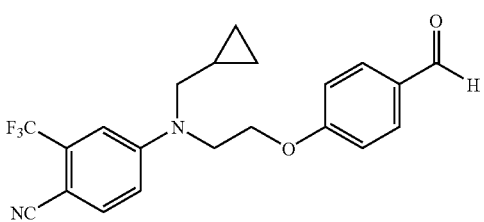

A. 4-((Cyclopropylmethyl){2-[(4-formylphenyl)oxy]ethyl}amino)-2-(trifluoromethyl)benzonitrile Synthesized as described in Example 1C from 4-[(cyclopropylmethyl)(2-hydroxyethyl)amino]-2-(trifluoromethyl)benzonitrile and 4-hydroxybenzaldehyde, then used directly for the step below, step B.

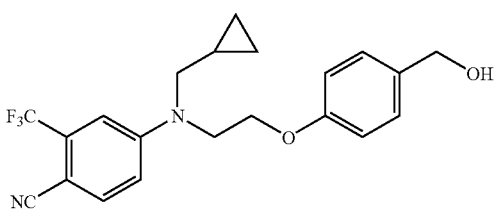

B. 4-[(Cyclopropylmethyl)(2-{[4-(hydroxymethyl)phenyl]oxy}ethyl)amino]-2-(trifluoromethyl)benzonitrile To a solution of 4-((cyclopropylmethyl){2-[(4-formylphenyl)oxy]ethyl}amino)-2-(trifluoromethyl)benzonitrile (0.0701 g, 0.181 mmol) in MeOH (1 mL) at 0° C. was added NaBH$_4$ (0.0034 g, 0.090 mmol) in one portion. The mixture was stirred 15 min, quenched by dropwise addition of NH$_4$Cl (sat'd) and poured into water. The whole was extracted with CH$_2$Cl$_2$ (×3), combined organic portions were washed with brine, dried over Na$_2$SO$_4$, filtered, and concentrated in vacuo. The residue was purified by flash chromatography (EtOAc/hexanes), affording 0.0556 g of the title compound as a colorless film: $^1$H NMR (300 MHz, CDCl$_3$) δ 7.58 (d, J=8.9 Hz, 1H), 7.28 (app. d, J=8.4 Hz, 2H), 7.12 (d, J=2.4 Hz, 1H), 6.91 (dd, J=8.9, 2.5 Hz, 1H), 6.83 (app. d, J=8.5 Hz, 2H), 4.61 (s, 2H), 4.16 (t, J=5.6 Hz, 2H), 3.91 (t, J=5.6 Hz, 2H), 3.40 (d, J=6.3 Hz, 2H), 1.69 (bs, 1H), 1.14-0.99 (m, 1H), 0.69-0.59 (m, 2H), 0.36-0.28 (m, 2H).

Example 6

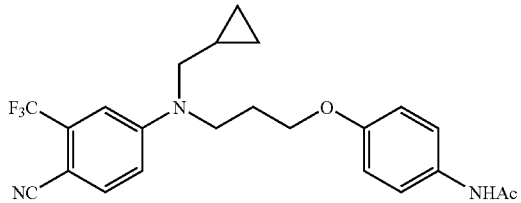

N-[4-({3-[[4-Cyano-3-(trifluoromethyl)phenyl](cyclopropylmethyl)amino]propyl}oxy)phenyl]acetamide

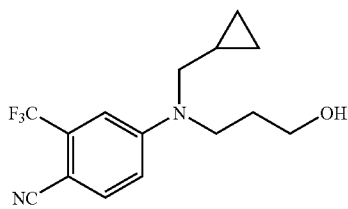

A. 4-[(Cyclopropylmethyl)(3-hydroxypropyl)amino]-2-(trifluoromethyl)benzonitrile Synthesized as described in Example 1B from 4-[(cyclopropylmethyl) amino]-2-(trifluoromethyl)benzonitrile and [(3-bromopropyl)oxy](1,1-dimethylethyl)dimethylsilane: $^1$H NMR (300 MHz, CD$_3$OD) δ 7.63 (d, J=8.7 Hz, 1H), 7.11 (d, J=2.6 Hz, 1H), 7.02 (dd, J=9.0, 2.7 Hz, 1H), 3.66-3.56 (m, 4H), 3.37 (d, J=6.4 Hz, 2H), 1.83 (tt, J=7.2, 6.2 Hz, 2H), 1.13-0.98 (m, 1H), 0.64-0.53 (m, 2H), 0.37-0.28 (m, 2H); MS (APCI) m/z 299 (M+1).

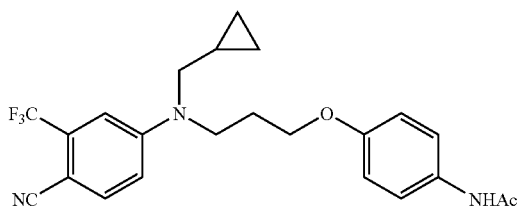

B. N-[4-({3-[[4-Cyano-3-(trifluoromethyl)phenyl](cyclopropylmethyl)amino]propyl}oxy)phenyl]acetamide Synthesized as described in Example 1C from 4-[(cyclopropylmethyl)(3-hydroxypropyl)amino]-2-(trifluoromethyl)benzonitrile and 4-acetamidophenol: MS (APCI) m/z 432 (M+1).

Example 7

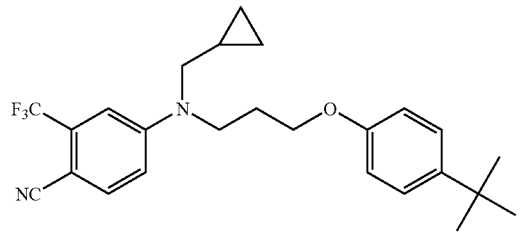

4-[(Cyclopropylmethyl)(3-{[4-(1,1-dimethylethyl)phenyl]oxy}propyl)amino]-2-(trifluoromethyl)benzonitrile Synthesized as described in Example 1C from 4-[(cyclopropylmethyl)(3-hydroxypropyl)amino]-2-(trifluoromethyl)benzonitrile and 4-tert-butylphenol: MS (APCI) m/z 431 (M+1).

Example 8

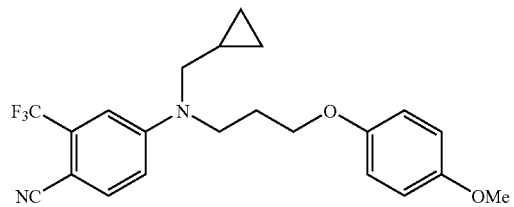

4-[(Cyclopropylmethyl)(3-{[4-(methyloxy)phenyl]oxy}propyl)amino]-2-(trifluoromethyl)benzonitrile Synthesized as described in Example 1C from 4-[(cyclopropylmethyl)(3-hydroxypropyl)amino]-2-(trifluoromethyl)benzonitrile and 4-methoxyphenol: MS (APCI) m/z 405 (M+1).

Example 9

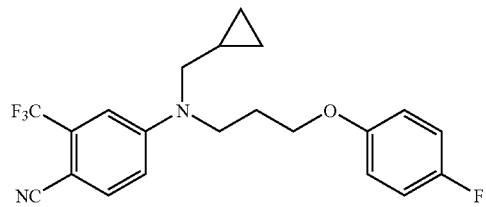

4-((Cyclopropylmethyl){3-[(4-fluorophenyl)oxy]propyl}amino)-2-(trifluoromethyl)benzonitrile Synthesized as described in Example 1C from 4-[(cyclopropylmethyl)(3-hydroxypropyl)amino]-2-(trifluoromethyl)benzonitrile and 4-fluorophenol: MS (APCI) m/z 393 (M+1).

Example 10

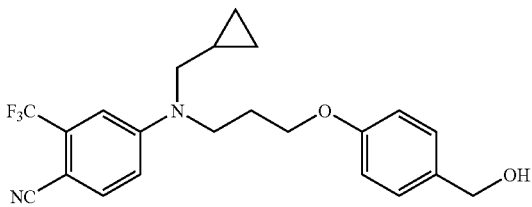

4-[(Cyclopropylmethyl)(3-{[4-(hydroxymethyl)phenyl]oxy}propyl)amino]-2-(trifluoromethyl)benzonitrile Synthesized as described in Example 5B from 4-[(cyclopropylmethyl)(3-hydroxypropyl)amino]-2-(trifluoromethyl)benzonitrile and 4-hydroxybenzaldehyde: MS (APCI) m/z 405 (M+1).

Example 11

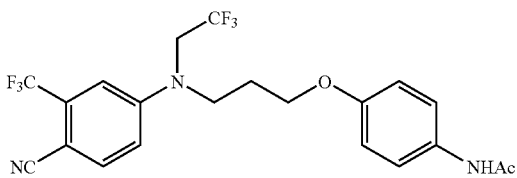

N-[4-({3-[[4-Cyano-3-(trifluoromethyl)phenyl](2,2,2-trifluoroethyl)amino]propyl}oxy)phenyl]acetamide

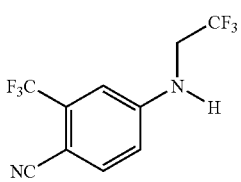

A. 4-(2,2,2-Trifluoro-ethylamino)-2-trifluoromethyl-benzonitrile

To a slurry of 4-amino-2-(trifluoromethyl)benzonitrile (30.09 g, 162 mmol) and NaBH$_3$CN (21.35 g, 340 mmol) in CH$_2$Cl$_2$ (160 mL) at ice bath temperature neat TFA (160 mL, 2.08 mol) was added dropwise at a rate such that the internal temperature remained below 5° C. (CAUTION: exothermic reaction with hydrogen gas evolution). Trifluoroacetaldehyde hydrate (52.2 g, 405 mmol) was then added over 5 min (CAUTION: slightly exothermic reaction, with gas evolution). After 41 h, the mixture was slowly poured into sat'd NaHCO$_3$ (1 L) at 0° C. The mixture was then completely neutralized by portionwise addition of solid NaHCO$_3$. The mixture was stirred 30 min and precipitated solids were collected by filtration. Organic and aqueous phases of the filtrate were separated, and the aqueous layer extracted with CH$_2$Cl$_2$ (3×150 mL). Combined organic extracts were concentrated to dryness, combined with the solids collected previously, dissolved in EtOAc, washed (H$_2$O, brine), dried over Na$_2$SO$_4$, filtered through a short pad of Celite and concentrated to dryness. Recrystallization from EtOAc/hexanes yielded 32.61 g of the title compound as slightly tan crystalline plates, mp 132.5-134° C.: $^1$H NMR (300 MHz, CD$_3$OD) δ 7.59 (d, J=8.8 Hz, 1H), 7.05 (d, J=2.2 Hz, 1H), 6.92 (dd, J=8.7, 2.4 Hz, 1H), 3.92 (q, J=9.2 Hz, 2H).

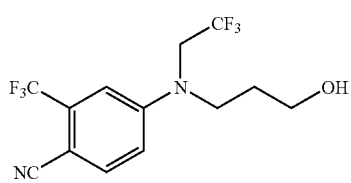

B. 4-[(3-Hydroxypropyl)(2,2,2-trifluoroethyl)amino]-2-(trifluoromethyl)benzonitrile Synthesized as described in Example 1B from 4-(2,2,2-trifluoro-ethylamino)-2-trifluoromethyl-benzonitrile and [(3-bromopropyl)oxy](1,1-dimethylethyl)dimethylsilane: MS (APCI) m/z 327 (M+1).

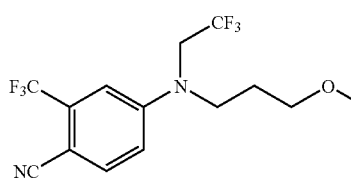

C. N-[4-({3-[[4-Cyano-3-(trifluoromethyl)phenyl](2,2,2-trifluoroethyl)amino]propyl}oxy)phenyl]acetamide Synthesized as described in Example 1C from 4-[(3-hydroxypropyl)(2,2,2-trifluoroethyl)amino]-2-(trifluoromethyl)benzonitrile and 4-acetamidophenol: MS (APCI) m/z 460 (M+1).

Example 12

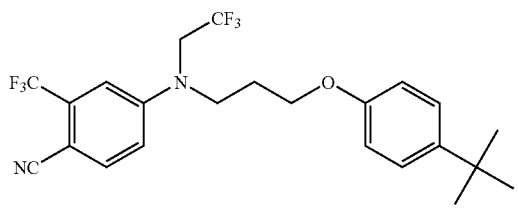

4-[(3-{[4-(1,1-Dimethylethyl)phenyl]oxy}propyl)(2,2,2-trifluoroethyl)amino]-2-(trifluoromethyl)benzonitrile Synthesized as described in Example 1C from 4-[(3-hydroxypropyl)(2,2,2-trifluoroethyl)amino]-2-(trifluoromethyl)benzonitrile and 4-tert-butylphenol: MS (ES) m/z 459 (M+1).

Example 13

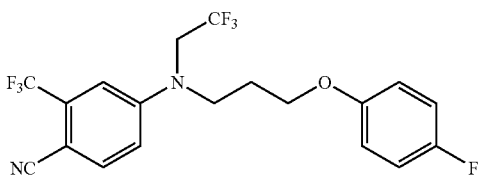

4-[{3-[(4-Fluorophenyl)oxy]propyl}(2,2,2-trifluoro-ethyl)amino]-2-(trifluoromethyl)benzonitrile Synthesized as described in Example 1C from 4-[(3-hydroxypropyl)(2,2,2-trifluoroethyl)amino]-2-(trifluoromethyl)benzonitrile and 4-fluorophenol: MS (ES) m/z 421 (M+1)

Example 14

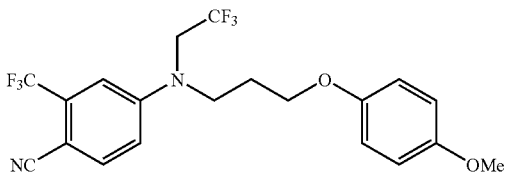

4-[(3-{[4-(Methyloxy)phenyl]oxy}propyl)(2,2,2-trifluoroethyl)amino]-2-(trifluoromethyl)benzonitrile Synthesized as described in Example 1C from 4-[(3-hydroxypropyl)(2,2,2-trifluoroethyl)amino]-2-(trifluoromethyl)benzonitrile and 4-methoxyphenol: MS (ESI) m/z 433 (M+1).

Example 15

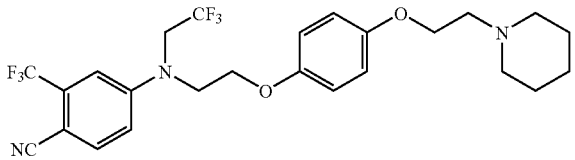

4-[{2-[(4-{[2-(1-Piperidinyl)ethyl]oxy}phenyl)oxy]ethyl}(2,2,2-trifluoroethyl)amino]-2-(trifluoromethyl)benzonitrile

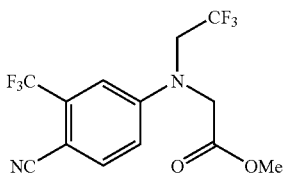

A. Methyl N-[4-cyano-3-(trifluoromethyl)phenyl]-N-(2,2,2-trifluoroethyl)glycinate A mixture of 4-(2,2,2-trifluoro-ethylamino)-2-trifluoromethyl-benzonitrile (5.00 g, 18.7 mmol), methyl bromoacetate (3.25 mL, 37.5 mmol), and $Cs_2CO_3$ (12.2 g, 37.3 mmol) in acetonitrile (50 mL) was held at reflux, under $N_2$, for 2 h and cooled to rt, and solids were removed by filtration. The filtrate was adsorbed onto a minimal amount of silica gel, filtered through a short pad of silica gel (EtOAc/hexanes) and concentrated to dryness. Recrystallization from EtOAc/hexanes afforded 4.72 g of the title compound as fine needles, mp 144-145° C.: $^1$H NMR (400 MHz, $CDCl_3$) δ 7.69 (d, J=8.9 Hz, 1H), 7.01 (d, J=2.3 Hz, 1H), 6.88 (dd, J=2.6 Hz, 1H), 4.24 (s, 2H), 4.06 (q, J=8.5 Hz, 2H), 3.81 (s, 3H).

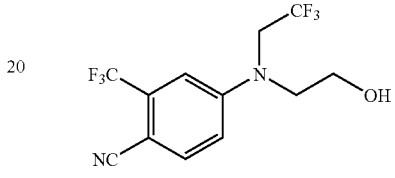

B. 4-[(2-Hydroxyethyl)(2,2,2-trifluoroethyl)amino]-2-(trifluoromethyl)benzonitrile To a solution of methyl N-[4-cyano-3-(trifluoromethyl)phenyl]-N-(2,2,2-trifluoroethyl)glycinate (1.67 g, 4.91 mmol) in THF (17 mL) at 0° C. was added a solution of $LiBH_4$ in THF (4.91 mL of a 2 M solution, 9.82 mmol), dropwise over 5 min. The cooling bath was removed, and the mixture was stirred 19 h at rt. The mixture was cooled to 0° C., quenched by dropwise addition of sat'd $NH_4Cl$ and poured into water. The whole was extracted with EtOAc (×3). Combined organic portions were washed (water, brine), dried over $Na_2SO_4$, filtered and concentrated in vacuo. The residue was purified by flash chromatography (EtOAc/hexanes), affording 1.22 g of the title compound as a white solid: $^1$H NMR (400 MHz, $CDCl_3$) δ 7.64 (d, J=9.1 Hz, 1H), 7.10 (d, J=2.7 Hz, 1H), 6.96 (dd, J=8.8, 2.5 Hz, 1H), 4.16 (q, J=8.5 Hz, 2H), 3.95 (app. q, J=5.1 Hz, 2H), 3.76 (t, J=5.4 Hz, 2H), 1.68 (t, J=4.6 Hz, 1H); MS (APCI) m/z 313 (M+1).

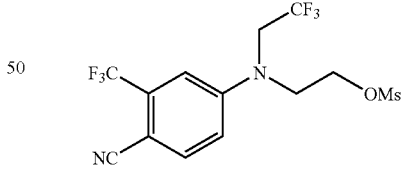

C. 2-[[4-Cyano-3-(trifluoromethyl)phenyl](2,2,2-trifluoroethyl)amino]ethyl methanesulfonate To a solution of 4-[(2-hydroxyethyl)(2,2,2-trifluoroethyl)amino]-2-(trifluoromethyl)benzonitrile (0.104 g, 0.333 mmol) in $CH_2Cl_2$ (3 mL) at 0° C. was added $Et_3N$ (0.07 mL, 0.5 mmol), followed by MsCl (0.03 mL, 0.37 mmol). The resulting mixture was stirred 12 h, gradually warming to rt. The mixture was poured into 10% v/v HCl and the layers were separated. The organic layer was washed (sat'd $NaHCO_3$, water, brine), dried over $Na_2SO_4$, filtered and concentrated to a colorless film (0.122 g), which was used without further purification: $^1$H NMR (300 MHz, CDCl$_3$) δ 7.71 (d, J=8.8 Hz, 1H), 7.12 (d, J=2.4 Hz, 1H), 6.99 (dd, J=8.7, 2.7 Hz, 1H), 4.43 (t, J=5.7 Hz, 2H), 4.10 (q, J=8.5 Hz, 2H), 3.95 (t, J=5.7 Hz, 2H), 3.02 (s, 3H).

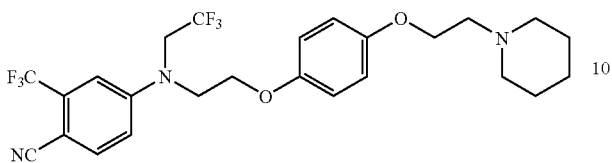

D. 4-[{2-[(4-{[2-(1-Piperidinyl)ethyl]oxy}phenyl) oxy]ethyl}(2,2,2-trifluoroethyl)amino]-2-(trifluoromethyl)benzonitrile To a slurry of hexanes-washed NaH (0.018 g of a 60% w/w suspension in mineral oil, 0.44 mmol) in DMF (1 mL) at 0° C. was added a solution of 4-{[2-(1-piperidinyl)ethyl] oxy}phenol (0.0714 g, 0.323 mmol, prepared according to Palkowitz, et al., *J. Med. Chem.* 1997, 40(10), 1407, herein incorporated by reference with regard to such synthesis) in DMF (2 mL), dropwise over 3 min. The resulting mixture was stirred 30 min and a solution of 2-[[4-cyano-3-(trifluoromethyl) phenyl](2,2,2-trifluoroethyl)amino]ethyl methanesulfonate (0.115 g, 0.294 mmol) in DMF (1 mL) was added. The cooling bath was removed and the mixture stirred at rt. After 90 min, the mixture was poured into water and the whole was extracted with EtOAc (×3). The combined organic portions were washed (1N NaOH, water, brine), dried over Na$_2$SO$_4$, filtered and concentrated in vacuo. The residue was purified by radial chromatography (silica gel, CH$_2$Cl$_2$/MeOH/NH$_3$ eluent), affording 0.0711 g of the title compound as a yellow gum: $^1$H NMR (300 MHz, CDCl$_3$) δ 7.66 (d, J=8.9 Hz, 1H), 7.16 (d, J=2.3 Hz, 1H), 6.98 (dd, J=8.9, 2.5 Hz, 1H), 6.87-6.79 (m, 2H), 6.79-6.72 (m, 2H), 4.25-4.12 (m, 4H), 4.04 (t, J=6.0 Hz, 2H), 3.97 (t, J=5.1 Hz, 2H), 2.74 (t, J=6.2 Hz, 2H), 2.55-2.43 (m, 4H), 1.66-1.54 (m, 4H), 1.49-1.39 (m, 2H); MS (ESI) m/z 517 ([M+2H]$^+$).

Example 16

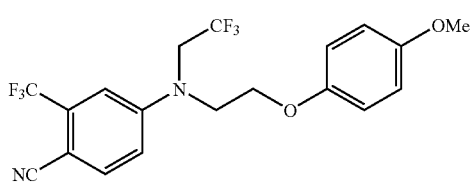

4-[(2-{[4-(Methyloxy)phenyl]oxy}ethyl)(2,2,2-trifluoroethyl)amino]-2-(trifluoromethyl)benzonitrile Synthesized as described in Example 1C using 4-[(2-hydroxyethyl)(2,2,2-trifluoroethyl)amino]-2-(trifluoromethyl) benzonitrile and 4-methoxyphenol: $^1$H NMR (300 MHz, CD$_3$OD) δ 7.73 (d, J=9.0 Hz, 1H), 7.36 (d, J=2.3 Hz, 1H), 7.25 (dd, J=9.0 Hz, 2.5 Hz, 1H), 6.80 (app. s, 4H), 4.42 (q, J=8.9 Hz, 2H), 4.17 (t, J=5.1 Hz, 2H), 4.00 (t, J=5.1 Hz, 2H), 3.51 (s, 3H); MS (APCI) m/z 419 (M+1).

Example 17

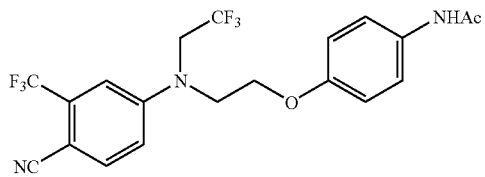

N-[4-({2-[[4-Cyano-3-(trifluoromethyl)phenyl](2,2, 2-trifluoroethyl)amino]ethyl}oxy)phenyl]acetamide Synthesized as described in Example 1C using 4-[(2-hydroxyethyl)(2,2,2-trifluoroethyl)amino]-2-(trifluoromethyl) benzonitrile and 4-acetamidophenol: MS (ES) m/z 446 (M+1).

Example 18

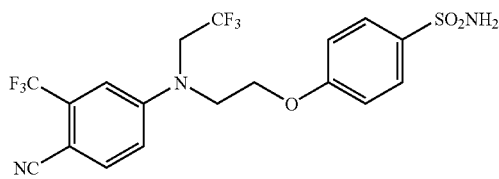

4-({2-[[4-Cyano-3-(trifluoromethyl)phenyl](2,2,2-trifluoroethyl)amino]ethyl}oxy)benzenesulfonamide Synthesized as described in Example 1C using 4-[(2-hydroxyethyl)(2,2,2-trifluoroethyl)amino]-2-(trifluoromethyl) benzonitrile and 4-hydroxybenzenesulfonamide: MS (APCI) m/z 468 (M+1).

Example 19

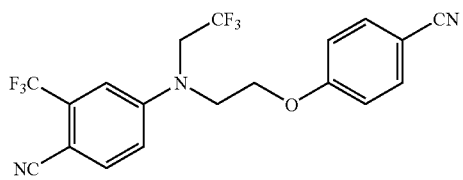

4-[{2-[(4-Cyanophenyl)oxy]ethyl}(2,2,2-trifluoroethyl)amino]-2-(trifluoromethyl)benzonitrile Synthesized as described in Example 1C using 4-[(2-hydroxyethyl)(2,2,2-trifluoroethyl)amino]-2-(trifluoromethyl) benzonitrile and 4-cyanophenol: $^1$H NMR (300 MHz, CD$_3$OD) δ 7.74 (d, J=8.8 Hz, 1H), 7.61 (app. d, J=8.8 Hz, 2H), 7.37 (d, J=2.1 Hz, 1H), 7.27 (dd, J=8.9, 2.4 Hz, 1H), 7.02 (app. d, J=8.8 Hz, 2H), 4.43 (q, J=8.9 Hz, 2H), 4.31 (t, J=5.2 Hz, 2H), 4.08 (t, J=5.1 Hz, 2H).

Example 20

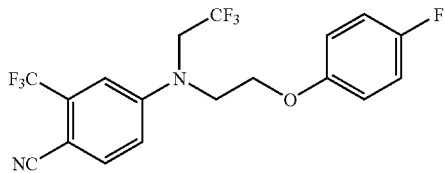

4-[{2-[(4-Fluorophenyl)oxy]ethyl}(2,2,2-trifluoroethyl)amino]-2-(trifluoromethyl)benzonitrile Synthesized as described in Example 1C using 4-[(2-hydroxyethyl)(2,2,2-trifluoroethyl)amino]-2-(trifluoromethyl)benzonitrile and 4-fluorophenol: MS (El) m/z 406 (M$^+$, 54%), 295 ([M-C$_6$H$_4$FO]$^+$, 82%), 281 (100%).

Example 21

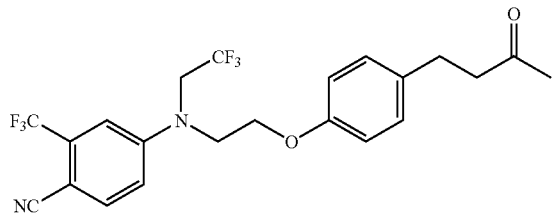

4-[(2-{[4-(3-Oxobutyl)phenyl]oxy}ethyl)(2,2,2-trifluoroethyl)amino]-2-(trifluoromethyl)benzonitrile Synthesized as described in Example 1C using 4-[(2-hydroxyethyl)(2,2,2-trifluoroethyl)amino]-2-(trifluoromethyl)benzonitrile and 4-(4-hydroxyphenyl)-2-butanone: MS (APCI) m/z 459 (M+1).

Example 22

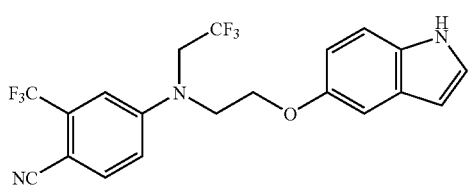

4-[[2-(1H-Indol-5-yloxy)ethyl](2,2,2-trifluoroethyl)amino]-2-(trifluoromethyl)benzonitrile Synthesized as described in Example 1C using 4-[(2-hydroxyethyl)(2,2,2-trifluoroethyl)amino]-2-(trifluoromethyl)benzonitrile and 5-hydroxyindole: MS (APCI) m/z 426 (M−1).

Example 23

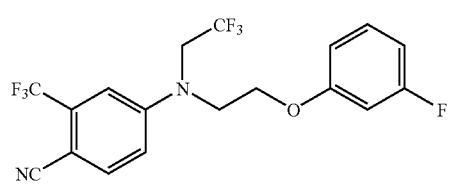

4-[{2-[(3-Fluorophenyl)oxy]ethyl}(2,2,2-trifluoroethyl)amino]-2-(trifluoromethyl)benzonitrile Synthesized as described in Example 1C using 4-[(2-hydroxyethyl)(2,2,2-trifluoroethyl)amino]-2-(trifluoromethyl)benzonitrile and 3-fluorophenol: MS (APCI) m/z 407 (M+1).

Example 24

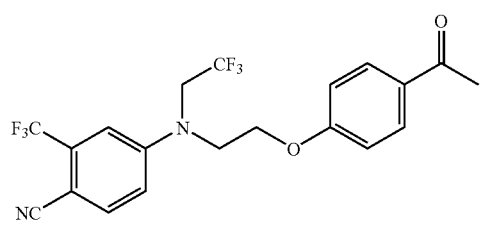

4-[{2-[(4-Acetylphenyl)oxy]ethyl}(2,2,2-trifluoroethyl)amino]-2-(trifluoromethyl)benzonitrile Synthesized as described in Example 1C using 4-[(2-hydroxyethyl)(2,2,2-trifluoroethyl)amino]-2-(trifluoromethyl)benzonitrile and 4-hydroxyacetophenone: MS (APCI) m/z 431 (M+1).

Example 25

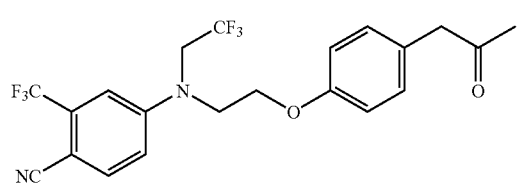

4-[(2-{[4-(2-Oxopropyl)phenyl]oxy}ethyl)(2,2,2-trifluoroethyl)amino]-2-(trifluoromethyl)benzonitrile Synthesized as described in Example 1C using 4-[(2-hydroxyethyl)(2,2,2-trifluoroethyl)amino]-2-(trifluoromethyl)benzonitrile and 1-(4-hydroxyphenyl)-2-propanone: MS (APCI) m/z 445 (M+1).

Example 26

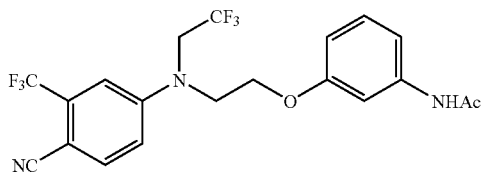

N-[3-({2-[[4-Cyano-3-(trifluoromethyl)phenyl](2,2,2-trifluoroethyl)amino]ethyl}oxy)phenyl]acetamide Synthesized as described in Example 1C using 4-[(2-hydroxyethyl)(2,2,2-trifluoroethyl)amino]-2-(trifluoromethyl)benzonitrile and 3-acetamidophenol: MS (APCI) m/z 446 (M+1).

Example 27

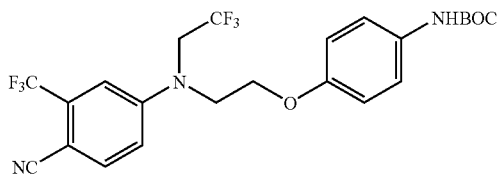

1,1-Dimethylethyl [4-({2-[[4-cyano-3-(trifluoromethyl)phenyl](2,2,2-trifluoroethyl)amino]ethyl}oxy)phenyl]carbamate

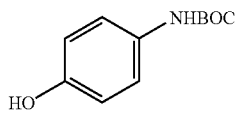

A. 1,1-Dimethylethyl (4-hydroxyphenyl)carbamate

To a solution of 4-aminophenol (1.00 g, 9.17 mmol) and Et₃N (1.27 mL, 9.17 mmol) in DMF (7.5 mL) at 0° C. was added a solution of di-tert-butyl dicarbonate (2.00 g, 9.17 mmol) in DMF (2.5 mL). The resulting mixture was stirred overnight, and allowed to gradually warm to rt. The mixture was poured into water and precipitated solids were collected by filtration. The collected solids were dissolved in EtOAc, washed (water, brine), dried over Na₂SO₄, filtered and concentrated to dryness. The title compound was obtained as a colorless solid (1.33 g) and used (see below) without further purification: ¹H NMR (300 MHz, CD₃OD) δ 7.15 (app. d, J=8.6 Hz, 2H), 6.69 (app. d, J=8.7 Hz, 2H), 1.49 (s, 9H).

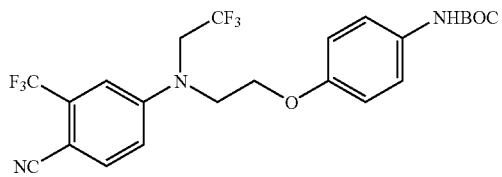

B. 1,1-Dimethylethyl [4-({2-[[4-cyano-3-(trifluoromethyl)phenyl](2,2,2-trifluoroethyl)amino]ethyl}oxy)phenyl]carbamate To a solution of 4-[(2-hydroxyethyl)(2,2,2-trifluoroethyl)amino]-2-(trifluoromethyl)benzonitrile (0.100 g, 0.32 mmol), 1,1-dimethylethyl (4-hydroxyphenyl)carbamate (0.0737 g, 0.35 mmol) and ADDP (0.121 g, 0.48 mmol) in THF (3.5 mL) at rt was added tri-n-butylphosphine (0.12 mL, 0.48 mmol). The resulting mixture was stirred 1 hour at rt and diluted with EtOAc until homogeneous. The resulting solution was extracted with 1 N NaOH (×2), washed (water, brine), dried over Na₂SO₄ and filtered. The filtrate was adsorbed onto a minimal amount of silica gel and purified by flash chromatography (EtOAc/hexanes), affording 0.133 g of the title compound as a colorless gum: ¹H NMR (400 MHz, CDCl₃) δ 7.66 (d, J=9.0 Hz, 1H), 7.26 (app. d, J=8.3 Hz, 2H), 7.16 (d, J=2.3 Hz, 1H), 6.98 (dd, J=9.0, 2.5 Hz, 1H), 6.80-6.75 (m, 2H), 6.38 (bs, 1H), 4.24-4.14 (m, 4H), 3.97 (t, J=5.1 Hz, 2H), 1.50 (s, 9H); MS (ESI) m/z 502 (M−1).

Example 28

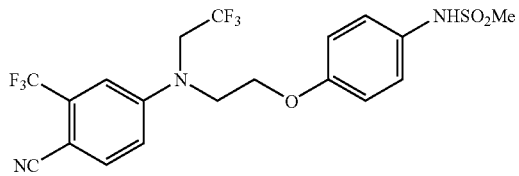

N-[4-({2-[[4-Cyano-3-(trifluoromethyl)phenyl](2,2,2-trifluoroethyl)amino]ethyl}oxy)phenyl]methanesulfonamide

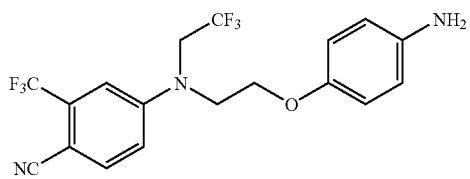

A. 4-[{2-[(4-Aminophenyl)oxy]ethyl}(2,2,2-trifluoroethyl)amino]-2-(trifluoromethyl)benzonitrile To a solution of 1,1-dimethylethyl [4-({2-[[4-cyano-3-(trifluoromethyl)phenyl](2,2,2-trifluoroethyl)amino]ethyl}oxy)phenyl]carbamate (0.132 g, 0.262 mmol; Example 27B) in CH₂Cl₂ (5 mL) at rt was added Et₃SiH (0.10 mL, 0.66 mmol), followed by TFA (2 mL). The mixture was stirred 40 min and slowly poured into satd NaHCO₃. The whole was extracted with EtOAc (×3). Combined organics were washed (water, brine), dried over Na₂SO₄, filtered and concentrated in vacuo, yielding 0.098 g of the title compound as a colorless gum which was used without further purification: MS (APCI) m/z 404 (M+1).

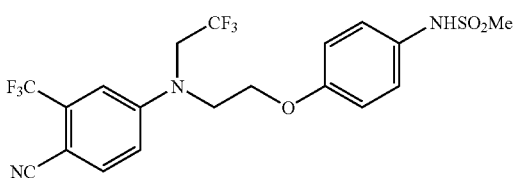

B. N-[4-({2-[[4-Cyano-3-(trifluoromethyl)phenyl](2, 2,2-trifluoroethyl)amino]ethyl}oxy)phenyl]methane-sulfonamide To a solution of 4-[{2-[(4-aminophenyl)oxy]ethyl}(2,2,2-trifluoroethyl)amino]-2-(trifluoromethyl)benzonitrile (0.0423 g, 0.105 mmol) in dry pyridine (1 mL) at rt, under nitrogen, was added MsCl (0.010 mL, 0.12 mmol) in one portion. The mixture was stirred 22 h and concentrated in vacuo. The residue was partitioned between EtOAc and 10% v/v HCl and the layers were separated. The organic layer was washed (water, brine), dried over Na₂SO₄, filtered and concentrated in vacuo. The residue was purified by flash chromatography (EtOAc/hexanes), affording 0.0372 g of the title compound as a colorless film: ¹H NMR (300 MHz, CD₃OD) δ 7.74 (d, J=8.8 Hz, 1H), 7.37 (d, J=2.4 Hz, 1H), 7.26 (dd, J=8.8, 2.5 Hz, 1H), 7.19-7.12 (m, 2H), 6.90-6.83 (m, 2H), 4.43 (q, J=8.9 Hz, 2H), 4.22 (t, J=5.1 Hz, 2H), 4.04 (t, J=5.1 Hz, 2H), 2.85 (s, 3H); MS (APCI) m/z 480 (M−1).

Example 29

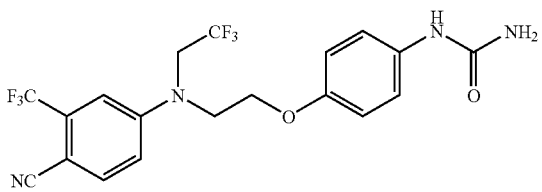

N-[4-({2-[[4-Cyano-3-(trifluoromethyl)phenyl](2,2, 2-trifluoroethyl)amino]ethyl}oxy)phenyl]urea To a solution of 4-[{2-[(4-aminophenyl)oxy]ethyl}(2,2,2-trifluoroethyl)amino]-2-(trifluoromethyl)benzonitrile (0.105 g, 0.25 mmol; Example 28A) in dry CH₂Cl₂ (5 mL) at room temp, under N₂, was added TMS-isocyanate (0.05 mL, 0.29 mmol) and the mixture was stirred overnight. After 12 h, an additional portion of TMS-isocyanate (0.09 mL, 0.58 mmol) and DMAP (0.003 g, 0.025 mmol) was added and stirring continued. After 2 h, the mixture was quenched with 10% v/v HCl and the whole extracted with EtOAc (×3). Combined organics were washed (water, brine), dried over Na₂SO₄, filtered and concentrated in vacuo. The residue was purified by flash chromatography (EtOAc/hexanes), followed by preparative RP-HPLC (C₁₈ column, MeCN/water), affording 0.0448 g of the title compound as a colorless gum: MS (ES) m/z 447 (M+1).

Example 30

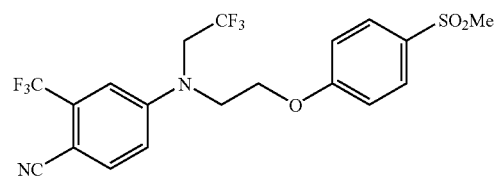

4-[(2-{[4-(Methylsulfonyl)phenyl]oxy}ethyl)(2,2,2-trifluoroethyl)amino]-2-(trifluoromethyl)benzonitrile Synthesized as described in Example 1C from 4-[(2-hydroxyethyl)(2,2,2-trifluoroethyl)amino]-2-(trifluoromethyl)benzonitrile and 4-methanesulfonylphenol: ¹H NMR (300 MHz, CDCl₃) δ 7.67 (app. d, J=8.8 Hz, 2H), 7.67 (d, J=8.6 Hz, 1H), 7.19 (d, J=2.5 Hz, 1H), 7.05-6.95 (m, 3H), 4.29 (t, J=5.3 Hz, 2H), 4.20 (q, J=8.6 Hz, 2H), 4.05 (t, J=5.1 Hz, 2H), 3.01 (s, 3H).

Example 31

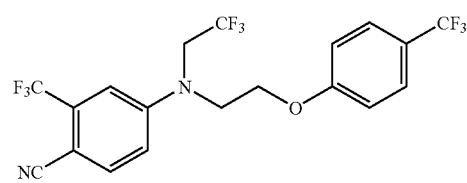

4-[(2,2,2-Trifluoroethyl)(2-{[4-(trifluoromethyl) phenyl]oxy}ethyl)amino]-2-(trifluoromethyl)benzonitrile Synthesized as described in Example 1C from 4-[(2-hydroxyethyl)(2,2,2-trifluoroethyl)amino]-2-(trifluoromethyl)benzonitrile and 4-(trifluoromethyl)phenol: MS (EI) m/z 456 (M+, 4%), 295 ([M-C₇H₄F₃O]⁺, 9%), 281 (100%).

Example 32

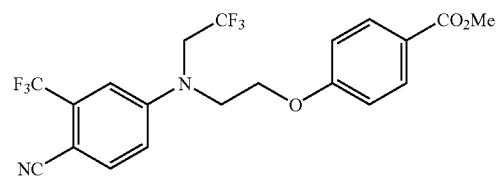

Methyl 4-({2-[[4-cyano-3-(trifluoromethyl)phenyl] (2,2,2-trifluoroethyl)amino]ethyl}oxy)benzoate Synthesized as described in Example 1C from 4-[(2-hydroxyethyl)(2,2,2-trifluoroethyl)amino]-2-(trifluoromethyl)benzonitrile and methyl 4-hydroxybenzoate: MS (APCI) m/z 446 (M+).

Example 33

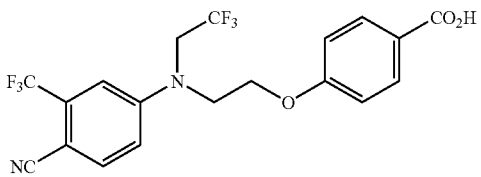

4-({2-[[4-Cyano-3-(trifluoromethyl)phenyl](2,2,2-trifluoroethyl)amino]ethyl}oxy)benzoic acid To a solution of methyl 4-({2-[[4-cyano-3-(trifluoromethyl)phenyl](2,2,2-trifluoroethyl)amino]ethyl}oxy)benzoate (0.0863 g, 0.193 mmol, Example 32) in THF (3 mL) at rt was added LiOH.H$_2$O (0.041 g, 0.97 mmol) and water (0.30 mL). The mixture was stirred 19 h at rt, then 8 h at reflux, cooled and partitioned between 1 N NaOH/Et$_2$O. Layers were separated, and the aqueous layer extracted with Et$_2$O (×1). The aqueous layer was then acidified to approximately pH 1 by addition of 2N HCl and extracted with EtOAc (×3). Combined EtOAc extracts were washed with brine, dried over Na$_2$SO$_4$ and concentrated in vacuo yielding 0.0816 g of the title compound as a colorless film which crystallized when triturated with CDCl$_3$: $^1$H NMR (400 MHz, CD$_3$OD) δ 7.97-7.90 (m, 2H), 7.75 (d, J=8.9 Hz, 1H), 7.38 (d, J=2.3 Hz, 1H), 7.28 (dd, J=8.9, 2.5 Hz, 1H), 6.97-6.92 (m, 2H), 4.45 (q, J=8.8 Hz, 2H), 4.31 (t, J=5.2 Hz, 2H), 4.08 (t, J=5.2 Hz, 2H); MS (ESI) m/z 431 (M−1).

Example 34

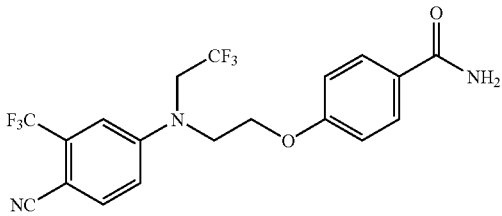

4-({2-[[4-Cyano-3-(trifluoromethyl)phenyl](2,2,2-trifluoroethyl)amino]ethyl}oxy)benzamide To a solution of 4-({2-[[4-cyano-3-(trifluoromethyl)phenyl](2,2,2-trifluoroethyl)amino]ethyl}oxy)benzoic acid (0.0498 g, 0.115 mmol) and di-tert-butyl-dicarbonate (0.0377 g, 0.173 mmol) in dry MeCN (1.5 mL) at rt, under nitrogen, was added pyridine (0.010 mL, 0.12 mmol). The mixture was stirred 30 min and NH$_4$HCO$_3$ (0.0137 g, 0.173 mmol) was added in one portion. The mixture was stirred 15 h and concentrated in vacuo. The residue was partitioned between EtOAc/10% v/v HCl and the layers were separated. The organic layer was washed (1 N NaOH, water, brine), dried over Na$_2$SO$_4$, filtered and concentrated in vacuo. The residue was purified by flash chromatography (EtOAc/hexanes), affording 0.039 g of the title compound as a colorless film that slowly solidified: $^1$H NMR (400 MHz, CD$_3$OD) δ 7.78 (m, 2H), 7.75 (d, J=9.0 Hz, 1H), 7.39 (d, J=2.4 Hz, 1H), 7.27 (dd, J=8.8, 2.4 Hz, 1H), 6.97-6.92 (m, 2H), 4.44 (q, J=8.8 Hz, 2H), 4.30 (t, J=5.2 Hz, 2H), 4.07 (t, J=5.1 Hz, 2H); MS (ESI) m/z 432 (M+1).

Example 35

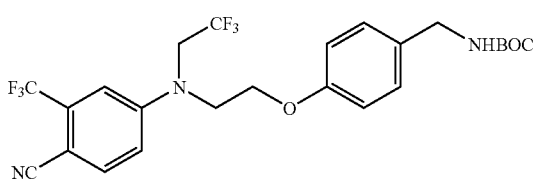

1,1-Dimethylethyl {[4-({2-[[4-cyano-3-(trifluoromethyl)phenyl](2,2,2-trifluoroethyl)amino]ethyl}oxy)phenyl]methyl}carbamate

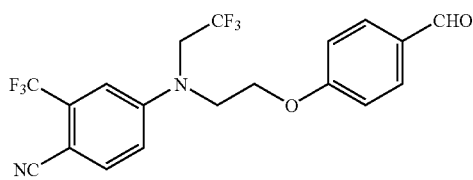

A. 4-[{2-[(4-Formylphenyl)oxy]ethyl}(2,2,2-trifluoroethyl)amino]-2-(trifluoromethyl)benzonitrile Synthesized as described in Example 1C from 4-[(2-hydroxyethyl)(2,2,2-trifluoroethyl)amino]-2-(trifluoromethyl)benzonitrile and methyl 4-hydroxybenzaldehyde: $^1$H NMR (300 MHz, CDC$_3$) δ 9.89 (s, 1H), 7.88-7.80 (m, 2H), 7.68 (d, J=8.9 Hz, 1H), 7.20 (d, J=2.4 Hz, 1H), 7.02 (dd, J=8.8, 2.7 Hz, 1H, partially overlapped with 6.99-6.93), 6.99-6.93 (m, 2H), 4.31 (t, J=5.2 Hz, 2H), 4.20 (q, J=8.5 Hz, 2H), 4.05 (t, J=5.2 Hz, 2H).

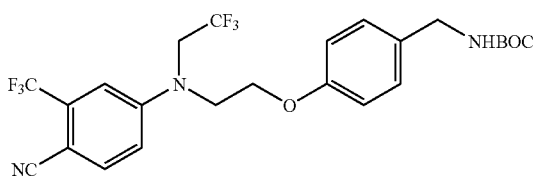

B. 1,1-Dimethylethyl {[4-({2-[[4-cyano-3-(trifluoromethyl)phenyl](2,2,2-trifluoroethyl)amino]ethyl}oxy)phenyl]methyl}carbamate A solution of 4-[{2-[(4-formylphenyl)oxy]ethyl}(2,2,2-trifluoroethyl)amino]-2-(trifluoromethyl)benzonitrile (0.0723 g, 0.174 mmol), hydroxylamine hydrochloride (0.0265 g, 0.382 mmol) and KOAc (0.0427 g, 0.435 mmol) in EtOH (1 mL) was heated at 80° C. (sealed vial) for 18 h, cooled, filtered through Celite and concentrated in vacuo. The residue was partitioned between EtOAc/water and the layers were separated. The organic layer was washed with brine, dried over Na$_2$SO$_4$, filtered and concentrated in vacuo. The residue was dissolved in EtOH/HOAc (1:1, 2 mL) and 10% w/w Pd on carbon (0.015 g) was added. The mixture was stirred under an atmosphere of hydrogen at rt for 4 h, filtered through Celite and concentrated in vacuo. The residue was partitioned between 1N NaOH/Et$_2$O and the layers were separated. The organic layer was concentrated in vacuo, yielding 0.071 g of a colorless gum that was dissolved in dioxane/water (4:1, 1.25 mL). To this solution was added 1N NaOH (0.19 mL), and di-tert-butyl-dicarbonate (0.041 g, 0.19 mmol). The mixture was stirred 24 h at rt, poured into water and the whole was extracted with EtOAc (×3). Combined organics were washed (water, brine), dried over Na$_2$SO$_4$, filtered and concentrated in vacuo. The residue was purified by flash chromatography (EtOAc/hexanes), affording 0.0283 g of the title compound as a colorless film: $^1$H NMR (400 MHz, CDCl$_3$) δ 7.67 (d, J=8.9 Hz, 1H), 7.24-7.14 (m, 3H), 6.99 (dd, J=8.8, 2.6 Hz, 1H), 6.83-6.77 (m, 2H), 4.79 (bs, 1H), 4.28-4.13 (m, 6H), 3.99 (t, J=5.1 Hz, 2H), 1.45 (s, 9H).

Example 36

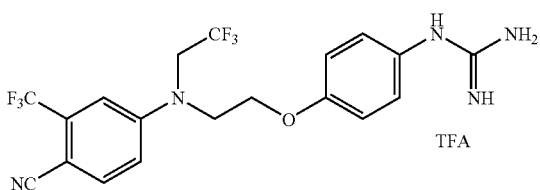

N-[4-({2-[[4-Cyano-3-(trifluoromethyl)phenyl](2,2,2-trifluoroethyl)amino]ethyl}oxy)phenyl]guanidine trifluoroacetate

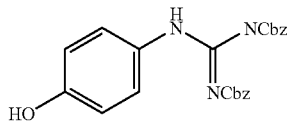

A. N,N'-Di-(benzyloxycarbonyl)-4-(hydroxyphenyl)guanidine

To a solution of 4-aminophenol (0.273 g, 2.50 mmol), di-(benzyloxycarbonyl)-S-methylisothiourea (0.941 g, 2.63 mmol) and Et$_3$N (1.04 mL, 7.5 mmol) in dry DMF (10 mL) was added HgCl$_2$ (0.745 g, 2.75 mmol) in one portion. The mixture was stirred 60 h at rt, under N$_2$, diluted with EtOAc and filtered through Celite. The filtrate was washed (sat'd Na$_2$CO$_3$, water, brine), dried over Na$_2$SO$_4$, filtered and concentrated in vacuo. The residue was purified by flash chromatography (EtOAc/hexanes), affording 0.944 g of the title compound as a colorless gum that solidified to a waxy solid on standing: $^1$H NMR (300 MHz, CDCl$_3$) δ 11.90 (bs, 1H), 9.99 (s, 1H), 7.48-7.21 (m, 10H), 7.19-7.10 (m, 2H), 6.68-6.59 (m, 2H), 6.23 (bs, 1H), 5.23 (s, 2H), 5.13 (s, 2H).

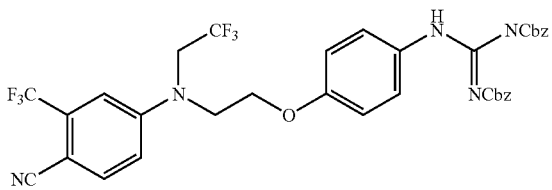

B. N-[4-({2-[[4-Cyano-3-(trifluoromethyl)phenyl](2,2,2-trifluoroethyl)amino]ethyl}oxy)phenyl]-N,N'-di-(benzyloxycarbonyl)-guanidine Synthesized as described in Example 1C from 4-[(2-hydroxyethyl)(2,2,2-trifluoroethyl)amino]-2-(trifluoromethyl)benzonitrile and N,N'-di-(benzyloxycarbonyl)-4-(hydroxyphenyl)guanidine: MS (ESI) m/z 714 (M+1).

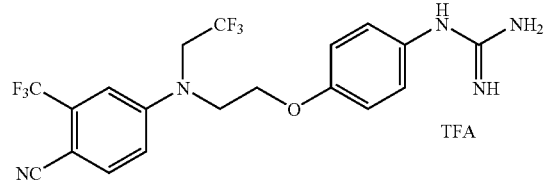

C. N-[4-({2-[[4-Cyano-3-(trifluoromethyl)phenyl](2,2,2-trifluoroethyl)amino]ethyl}oxy)phenyl]guanidine trifluoroacetate A mixture of N-[4-({2-[[4-cyano-3-(trifluoromethyl)phenyl](2,2,2-trifluoroethyl)amino]ethyl}oxy)phenyl]-N,N'-di-(benzyloxycarbonyl)-guanidine (0.087 g, 0.12 mmol) and 10% w/w Pd on carbon (0.050 g) in EtOH/EtOAc (1:1, 10 mL) was stirred under an atmosphere of hydrogen at rt for 4 h, filtered through Celite and concentrated in vacuo. The residue was purified by preparative HPLC (C18 column, MeCN/water mobile phase with 0.1% v/v TFA), affording 0.0337 g of the title compound as a pale yellow gum: $^1$H NMR (400 MHz, CD$_3$OD) δ 7.75 (d, J=8.9 Hz, 1H), 7.39 (d, J=2.4 Hz, 1H), 7.28 (dd, J=8.9, 2.5 Hz, 1H), 7.21-7.15 (m, 2H), 7.01-6.95 (m, 2H), 4.44 (q, J=8.9 Hz, 2H), 4.26 (t, J=5.1 Hz, 2H), 4.07 (t, J=5.1 Hz, 2H).

Example 37

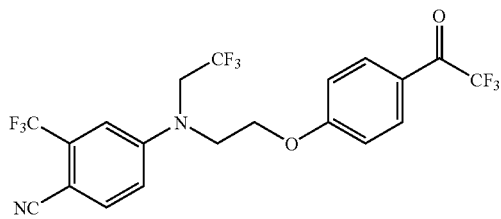

4-[(2-{[4-(Trifluoroacetyl)phenyl]oxy}ethyl)(2,2,2-trifluoroethyl)amino]-2-(trifluoromethyl)benzonitrile Synthesized as described in Example 1C from 4-[(2-hydroxyethyl)(2,2,2-trifluoroethyl)amino]-2-(trifluoromethyl)benzonitrile and 4-hydroxytrifluoroacetophenone (prepared according to Bittman et al., J. Org., Chem. 2003, 68(18), 7046, herein incorporated by reference with regard to such synthesis): MS (APCI) m/z 485 (M+1).

Example 38

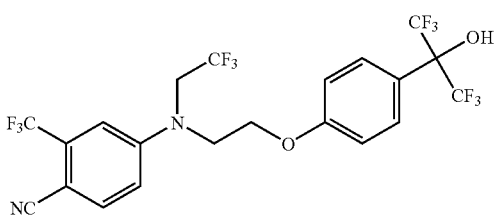

4-{(2,2,2-Trifluoroethyl)[2-({4-[2,2,2-trifluoro-1-hydroxy-1-(trifluoromethyl)ethyl]phenyl}oxy)ethyl]amino}-2-(trifluoromethyl)benzonitrile To a solution of 4-[(2-{[4-(trifluoroacetyl)phenyl]oxy}ethyl)(2,2,2-trifluoroethyl)amino]-2-(trifluoromethyl)benzonitrile (0.106 g, 0.22 mmol, example 37) and (trifluoromethyl)trimethylsilane (0.040 mL, 0.26 mmol) in dry DME at rt, under $N_2$, was added anhydrous CsF (0.0020 g, 0.011 mmol). The mixture was stirred 3 h at rt and an additional portion of (trifluoromethyl)trimethylsilane (0.040 mL, 0.26 mmol) was added, and the mixture stirred another 2 h. 2N HCl (5 mL) was added, and the mixture was stirred for 60 h at rt. The mixture was diluted with water and the whole extracted with EtOAc (×2). Combined organics were washed (water, brine, dried over $Na_2SO_4$ and concentrated in vacuo, affording 0.051 g of the title compound as a pale yellow solid: MS (ESI) m/z 553 (M−1).

Example 39

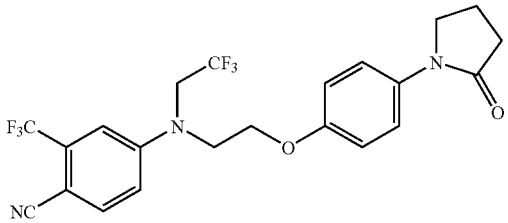

4-[(2-{[4-(2-Oxo-1-pyrrolidinyl)phenyl]oxy}ethyl)(2,2,2-trifluoroethyl)amino]-2-(trifluoromethyl)benzonitrile

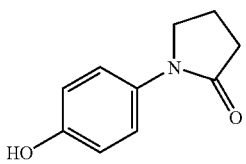

A. 1-(4-Hydroxyphenyl)-2-pyrrolidinone

To a solution of p-aminophenol (0.545 g, 5.00 mmol) in dry MeCN (5 mL) at 0° C. was added $K_2CO_3$ (1.38 g, 10.0 mmol), followed by dropwise addition of 4-chlorobutanoyl chloride (0.56 mL, 5.0 mmol). The mixture was stirred at rt for 40 min and then brought to reflux. Dry DMF (5 mL) was added after 90 min and heating was continued for an additional 2 h. The mixture was cooled, poured into water, and extracted with EtOAc (×8). Combined organics were washed with brine, dried over $Na_2SO_4$, filtered, and concentrated in vacuo. The residue was purified by flash chromatography (EtOAc/hexanes), affording 0.171 g of the title compound as a colorless solid: MS (APCI) m/z 177 ($M^+$).

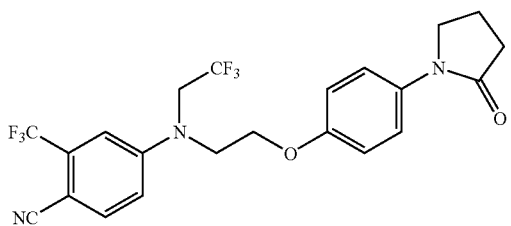

B. 4-[(2-{[4-(2-Oxo-1-pyrrolidinyl)phenyl]oxy}ethyl)(2,2,2-trifluoroethyl)amino]-2-(trifluoromethyl)benzonitrile Synthesized as described in Example 27B from 4-[(2-hydroxyethyl)(2,2,2-trifluoroethyl)amino]-2-(trifluoromethyl)benzonitrile (Example 15B) and 1-(4-hydroxyphenyl)-2-pyrrolidinone (step A above): MS (APCI) m/z 472 (M+1).

Example 40

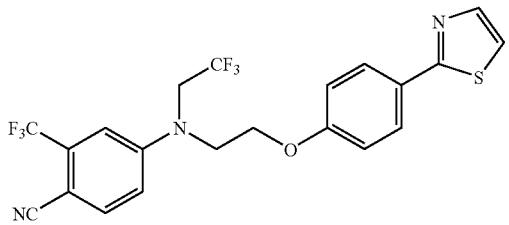

4-[(2-{[4-(1,3-Thiazol-2-yl)phenyl]oxy}ethyl)(2,2,2-trifluoroethyl)amino]-2-(trifluoromethyl)benzonitrile

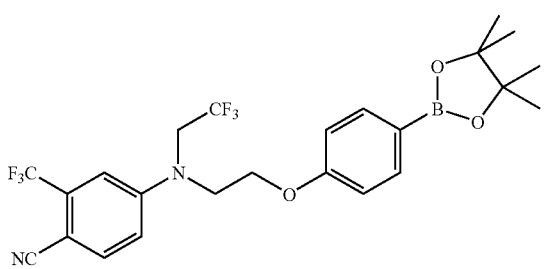

A. 4-[(2-{[4-(4,4,5,5-Tetramethyl-1,3,2-dioxaborolan-2-yl)phenyl]oxy}ethyl)(2,2,2-trifluoroethyl)amino]-2-(trifluoromethyl)benzonitrile Synthesized as described in Example 27B from 4-[(2-hydroxyethyl)(2,2,2-trifluoroethyl)amino]-2-(trifluoromethyl)benzonitrile (Example 15B) and 4-(4,4,5,5-tetramethyl-1,3, 2-dioxaborolan-2-yl)phenol, using dry DME as the reaction solvent: $^1$H NMR (400 MHz, CDCl$_3$) δ 7.74 (m, 2H; AA' XX'), 7.67 (d, J=8.9 Hz, 1H), 7.16 (d, J=2.7 Hz, 1H), 6.99 (dd, J=8.9, 2.7 Hz, 1H), 6.84 (m, 2H; AA'XX'), 4.24 (t, J=5.2 Hz, 2H; partially overlapping 4.20), 4.20 (q, J=8.5 Hz, 2H; partially overlapping 4.24), 4.00 (t, J=5.1 Hz, 2H), 1.33 (s, 12H).

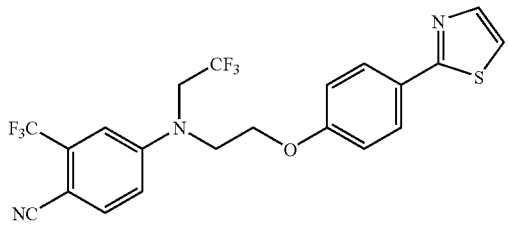

B. 4-[(2-{[4-(1,3-Thiazol-2-yl)phenyl]oxy}ethyl)(2,2,2-trifluoroethyl)amino]-2-(trifluoromethyl)benzonitrile A mixture of 4-[(2-{[4-(4,4,5,5-tetramethyl-1,3,2-dioxaborolan-2-yl)phenyl]oxy}ethyl)(2,2,2-trifluoroethyl)amino]-2-(trifluoromethyl)benzonitrile (0.100 g, 0.19 mmol; step A above), 2-bromothiazole (0.020 mL, 0.21 mmol), Pd(PPh$_3$)$_4$ (0.011 g, 0.010 mmol), Na$_2$CO$_3$ (0.106 g, 1.00 mmol), toluene (1 mL), EtOH (0.50 mL) and H$_2$O (0.5 mL) was sparged with N$_2$ for 10 min and then heated at 80° C. in a sealed vial for 72 h. The mixture was cooled, poured into water, and extracted with EtOAc (×3). Combined organics were washed (H$_2$O, brine), dried over Na$_2$SO$_4$, filtered, and concentrated in vacuo. The residue was purified by flash chromatography (EtOAc/hexanes), affording 0.0059 g of the title compound as a yellow film: MS (ESI) m/z 472 (M+1).

Example 41

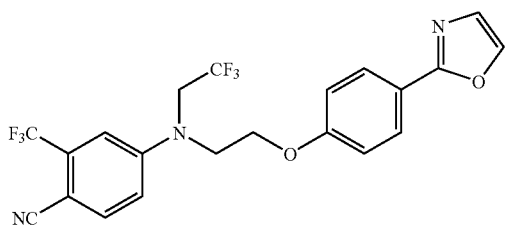

4-[(2-{[4-(1,3-Oxazol-2-yl)phenyl]oxy}ethyl)(2,2,2-trifluoroethyl)amino]-2-(trifluoromethyl)benzonitrile

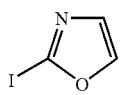

A. 2-Iodo-1,3-oxazole

To a solution of oxazole (0.33 mL, 5.0 mmol) in dry THF (10 mL) at −78° C. was added n-BuLi (2.20 mL of a 2.5M solution in hexanes, 5.50 mmol), dropwise over 3 min. The mixture was stirred 30 min and a solution of anhydrous ZnBr$_2$ (5.3 mL of a 1.13M solution in THF, 6.0 mmol) was added, dropwise over 3 min. The mixture was warmed to rt and I$_2$ (1.40 g, 5.5 mmol) was added in one portion. The mixture was stirred for 20 min, quenched with satd. Na$_2$S$_2$O$_3$, diluted with Et$_2$O and poured into 10 wt % citric acid solution. The biphasic mixture was stirred vigorously until clean phase separation occurred, and the layers were separated. The organic layer was washed with brine, dried over Na$_2$SO$_4$, filtered, and carefully concentrated in vacuo (45° C. water bath temp., 100 mbar vacuum). The residue was filtered through a short pad of silica gel (CH$_2$Cl$_2$ eluent), affording 0.674 g of the title compound as a pale yellow solid: $^1$H NMR (400 MHz, CDCl$_3$) δ 7.77 (d, J=0.7 Hz, 1H), 7.11 (d, J=0.7 Hz, 1H).

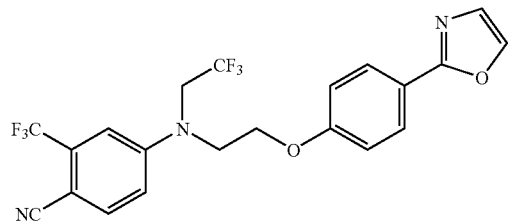

B. 4-[(2-{[4-(1,3-Oxazol-2-yl)phenyl]oxy}ethyl)(2,2,2-trifluoroethyl)amino]-2-(trifluoromethyl)benzonitrile Synthesized as described in Example 40B from 4-[(2-{[4-(4,4,5,5-tetramethyl-1,3,2-dioxaborolan-2-yl)phenyl]oxy}ethyl)(2,2,2-trifluoroethyl)amino]-2-(trifluoromethyl)benzonitrile (Example 40A) and 2-iodo-1,3-oxazole (step A above), with the following exceptions: additional 2-iodo-1,3-oxazole (0.3 equiv) was added after 2 h of heating, additional Pd(PPh$_3$)$_4$ (0.005 g) was added after 4 h of heating, and heating was maintained for only 6 h: MS (ESI) m/z 456 (M+1).

Example 42

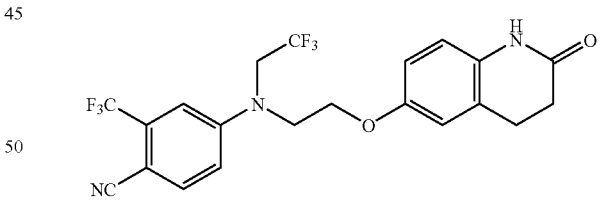

4-[{2-[(2-Oxo-1,2,3,4-tetrahydro-6-quinolinyl)oxy]ethyl}(2,2,2-trifluoroethyl)amino]-2-(trifluoromethyl)benzonitrile Synthesized as described in Example 27B from 4-[(2-hydroxyethyl)(2,2,2-trifluoroethyl)amino]-2-(trifluoromethyl)benzonitrile (Example 15B) and 6-hydroxy-3,4-dihydro-2(1H)-quinolinone with the following exceptions: PPh$_3$ was used instead of PBu$_3$ and purification of the title compound consisted of flash chromatography (EtOAc/hexanes) followed by RP-HPLC (MeCN/H$_2$O with 0.1% TFA): $^1$H NMR (400 MHz, acetone-D$_6$) δ 8.96 (bs, 1H), 7.83 (d, J=8.9 Hz, 1H), 7.49 (d, J=2.7 Hz, 1H), 7.41 (dd, J=8.9, 2.7 Hz, 1H), 6.84

(d, J=8.6 Hz, 1H), 6.79 (d, J=2.6 Hz, 1H), 6.74 (dd, J=8.6 Hz, 1H), 4.62 (q, J=9.0 Hz, 2H), 4.31 (t, J=5.3 Hz, 2H), 4.16 (t, J=5.3-Hz, 2H), 2.88 (partially resolved dd, J≈7.5, 7.0 Hz, 2H), 2.44 (dd, J=8.6, 6.4 Hz, 2H).

Example 43

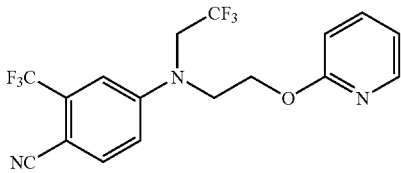

4-[[2-(2-Pyridinyloxy)ethyl](2,2,2-trifluoroethyl)amino]-2-(trifluoromethyl)benzonitrile Synthesized as described in Example 1C from 4-[(2-hydroxyethyl)(2,2,2-trifluoroethyl)amino]-2-(trifluoromethyl)benzonitrile and 2-pyridone, using dry DME as reaction solvent: MS (APCI) m/z 390 (M+1).

Example 44

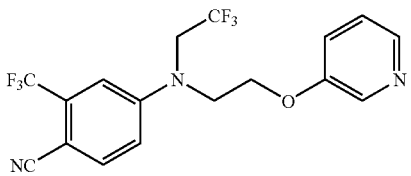

4-[[2-(3-Pyridinyloxy)ethyl](2,2,2-trifluoroethyl)amino]-2-(trifluoromethyl)benzonitrile Synthesized as described in Example 1C from 4-[(2-hydroxyethyl)(2,2,2-trifluoroethyl)amino]-2-(trifluoromethyl)benzonitrile and 3-hydroxypyridine, using dry DME as reaction solvent: $^1$H NMR (300 MHz, CDCl$_3$) δ 8.14 (dd, J=5.1, 1.6 Hz, 1H), 7.65 (d, J=8.9 Hz, 1H), 7.59 (ddd, J=8.5, 6.8, 1.7 Hz, 1H), 7.35 (d, J=2.5 Hz, 1H), 7.04 (dd, J=8.8, 2.5 Hz, 1H), 6.91 (dd, J=6.8, 5.4 Hz, 1H), 6.70 (d, J=8.3 Hz, 1H), 4.56 (t, J=6.1 Hz, 2H), 4.11 (q, J=8.5 Hz, 2H), 3.96 (t, J=6.1 Hz, 2H).

Example 45

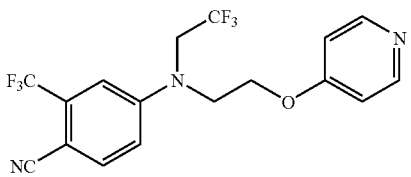

4-[[2-(4-Pyridinyloxy)ethyl](2,2,2-trifluoroethyl)amino]-2-(trifluoromethyl)benzonitrile Synthesized as described in Example 1C from 4-[(2-hydroxyethyl)(2,2,2-trifluoroethyl)amino]-2-(trifluoromethyl)benzonitrile and 4-pyridone, using dry DME as reaction solvent: $^1$H NMR (400 MHz, CDCl$_3$) δ 8.45 (dd, J=5.0, 1.3 Hz, 2H), 7.68 (d, J=8.8 Hz, 1H), 7.18 (d, J=2.5 Hz, 1H), 7.01 (dd, J=8.7, 2.6 Hz, 1H), 6.77 (dd, J=4.9, 1.3 Hz, 2H), 4.27 (t, J=5.2 Hz, 2H), 4.19 (q, J=8.5 Hz, 2H), 4.04 (t, J=5.3 Hz, 2H).

Example 46

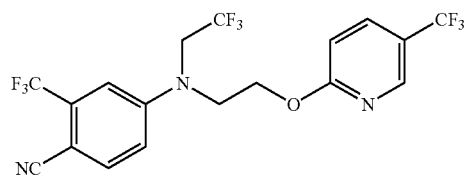

4-[(2,2,2-Trifluoroethyl)(2-{[5-(trifluoromethyl)-2-pyridinyl]oxy}ethyl)amino]-2-(trifluoromethyl)benzonitrile Synthesized as described in Example 1C from 4-[(2-hydroxyethyl)(2,2,2-trifluoroethyl)amino]-2-(trifluoromethyl)benzonitrile and 5-trifluoromethyl-2-pyridinol, using dry DME as reaction solvent: MS (ESI) m/z 458 (M+1).

Example 47

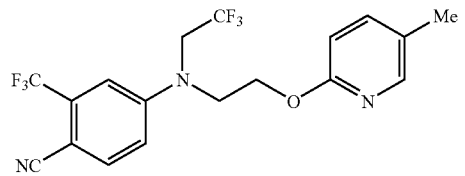

4-[{2-[(5-Methyl-2-pyridinyl)oxy]ethyl}(2,2,2-trifluoroethyl)amino]-2-(trifluoromethyl)benzonitrile Synthesized as described in Example 1C from 4-[(2-hydroxyethyl)(2,2,2-trifluoroethyl)amino]-2-(trifluoromethyl)benzonitrile and 5-methyl-2-pyridinol, using dry DME as reaction solvent: MS (APCI) m/z 404 (M+1).

Example 48

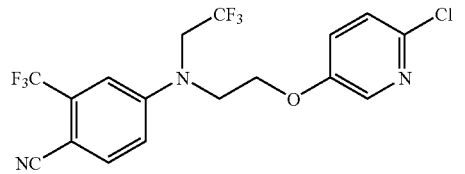

4-[{2-[(6-Chloro-3-pyridinyl)oxy]ethyl}(2,2,2-trifluoroethyl)amino]-2-(trifluoromethyl)benzonitrile Synthesized as described in Example 1C from 4-[(2-hydroxyethyl)(2,2,2-trifluoroethyl)amino]-2-(trifluoromethyl)benzonitrile and 6-chloro-3-pyridinol, using dry DME as reaction solvent: MS (APCI) m/z 424 (M+1).

Example 49

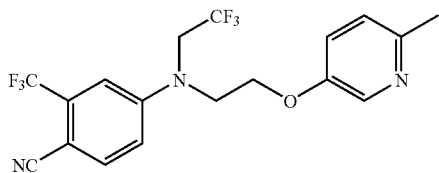

4-[{2-[(6-Methyl-3-pyridinyl)oxy]ethyl}(2,2,2-trifluoroethyl)amino]-2-(trifluoromethyl)benzonitrile Synthesized as described in Example 27B from 4-[(2-hydroxyethyl)(2,2,2-trifluoroethyl)amino]-2-(trifluoromethyl)benzonitrile (Example 15B) and 5-hydroxy-2-methylpyridine using dry DME as the reaction solvent: MS (ESI) m/z 404 (M+1).

Example 50

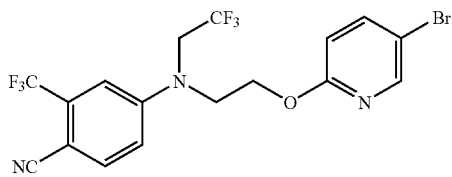

4-[{2-[(5-Bromo-2-pyridinyl)oxy]ethyl}(2,2,2-trifluoroethyl)amino]-2-(trifluoromethyl)benzonitrile Synthesized as described in Example 27B from 4-[(2-hydroxyethyl)(2,2,2-trifluoroethyl)amino]-2-(trifluoromethyl)benzonitrile (Example 15B) and 5-bromo-2(1H)-pyridinone using dry DME as the reaction solvent: MS (ESI) m/z 468 (M+1, $^{79}$Br), 470 (M+1, $^{81}$Br).

Example 51

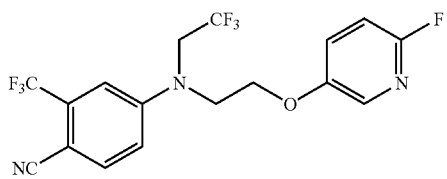

4-[{2-[(6-Fluoro-3-pyridinyl)oxy]ethyl}(2,2,2-trifluoroethyl)amino]-2-(trifluoromethyl)benzonitrile

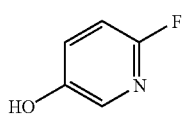

A. 6-Fluoro-3-pyridinol

To a solution of 5-bromo-2-fluoropyridine (0.26 mL, 2.5 mmol) in dry Et$_2$O (10 mL) at −78° C. was added n-BuLi (1.06 mL of a 2.5 M solution in hexanes, 2.7 mmol), dropwise over 3 min. The mixture was stirred 15 min and B(Oi-Pr)$_3$ (0.64 mL, 2.8 mmol) was added dropwise. The mixture was gradually warmed to rt over 30 min, 1M NaOH (2 mL) was added, followed by H$_2$O$_2$ (0.5 mL of a 30 wt % solution) and the mixture was stirred 30 min. Excess H$_2$O$_2$ was quenched by dropwise addition of a 10% solution of Na$_2$S$_2$O$_3$, the mixture was poured into water and the layers were separated. The aqueous layer was adjusted to pH 3.5 by addition of 1M KHSO$_4$ and extracted with EtOAc (×3). Combined organics portions were washed with brine, dried over Na$_2$SO$_4$, filtered and concentrated in vacuo. The residue was purified by flash chromatography (EtOAc/hexanes), affording 0.242 g of the title compound as a colorless solid: MS (APCI) m/z 114 (M+H).

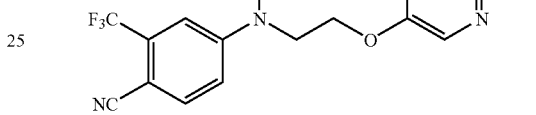

B. 4-[{2-[(6-Fluoro-3-pyridinyl)oxy]ethyl}(2,2,2-trifluoroethyl)amino]-2-(trifluoromethyl)benzonitrile Synthesized as described in Example 27B from 4-[(2-hydroxyethyl)(2,2,2-trifluoroethyl)amino]-2-(trifluoromethyl)benzonitrile (Example 15B) and 6-fluoro-3-pyridinol (step A above): MS (ESI) m/z 408 (M+1).

Example 52

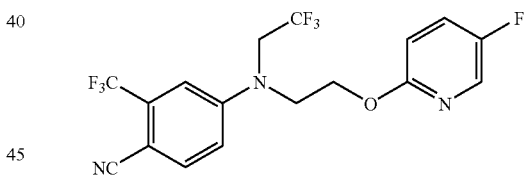

4-[{2-[(5-Fluoro-2-pyridinyl)oxy]ethyl}(2,2,2-trifluoroethyl)amino]-2-(trifluoromethyl)benzonitrile Synthesized as described in Example 27B from 4-[(2-hydroxyethyl)(2,2,2-trifluoroethyl)amino]-2-(trifluoromethyl)benzonitrile (Example 15B) and 5-fluoro-2(1H)-pyridinone, using dry DME as the reaction solvent: MS (APCI) m/z 408 (M+1).

Example 53

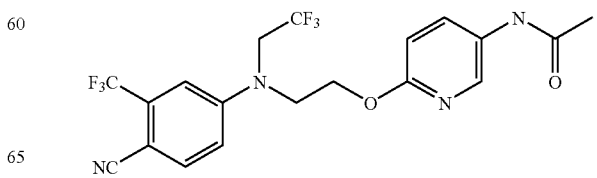

N-[6-({2-[[4-Cyano-3-(trifluoromethyl)phenyl](2,2,2-trifluoroethyl)amino]ethyloxy}-3-pyridinyl]acetamide

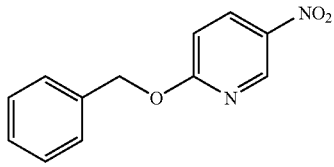

A. 5-Nitro-2-[(phenylmethyl)oxy]pyridine

To a mixture of 2-chloro-5-nitropyridine (3.28 g, 20.0 mmol), benzyl alcohol (3.09 mL, 30.0 mmol), KOH (4.49 g, 80.0 mmol), and $K_2CO_3$ (2.76 g, 20.0 mmol) in toluene (100 mL) at rt was added tris[2-(2-methoxyethoxy)ethyl]amine (0.646 g, 2.00 mmol). The mixture was stirred for 20 min, poured into water, and the layers were separated. The aqueous layer was adjusted to pH 7 by addition of solid $KHSO_4$, and extracted with EtOAc (×3). Combined organics were washed ($H_2O$, brine), dried over $Na_2SO_4$, filtered and concentrated in vacuo. The residue was recrystallized from EtOH/$H_2O$, affording 3.18 g of the title compound as tan needles: $^1$H NMR (400 MHz, $CDCl_3$) δ 9.10 (dd, J=2.9, 0.6 Hz, 1H), 8.37 (dd, J=9.1, 2.9 Hz, 1H), 7.48-7.44 (m, 2H), 7.42-7.33 (m, 3H), 6.88 (dd, J=9.1, 0.6 Hz, 1H), 5.49 (s, 2H).

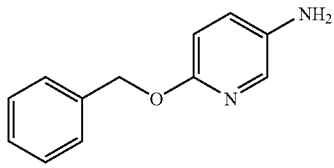

B. 6-[(Phenylmethyl)oxy]-3-pyridinamine

To a slurry of iron powder (5.32 g, 95 mmol) in MeOH/$H_2O$/HOAc (7.5 mL/7.5 mL/0.30 mL) at 75° C. was added 5-nitro-2-[(phenylmethyl)oxy]pyridine (3.10 g, 13.4 mmol; step A above), portionwise over 20 min. After 2 h, the mixture was cooled, 1M NaOH (10 mL) was added. The mixture was filtered through Celite (MeOH wash×2) and concentrated in vacuo. The residue was purified by flash chromatography (EtOAc/hexanes), affording 2.21 g of the title compound as an orange syrup: MS (ESI) m/z 201 (M+1).

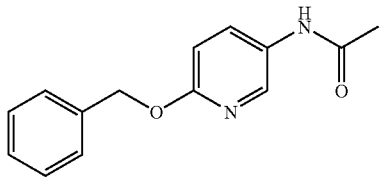

C. N-{6-[(Phenylmethyl)oxy]-3-pyridinyl}acetamide

To a solution of 6-[(phenylmethyl)oxy]-3-pyridinamine (0.213 g, 1.07 mmol; step B above) in $CH_2Cl_2$ (5 mL) at rt was added pyridine (0.17 mL, 2.14 mmol), DMAP (0.0065 g, 0.050 mmol) and $Ac_2O$ (0.12 mL, 1.28 mmol). After 5 min the mixture was poured into water and extracted with $CH_2Cl_2$ (×3). The combined organics were washed with brine, dried over $Na_2SO_4$, filtered, and concentrated in vacuo. The residue was purified by flash chromatography (EtOAc/hexanes), affording 0.245 g of the title compound as a colorless solid: MS (ESI) m/z 243 (M+1).

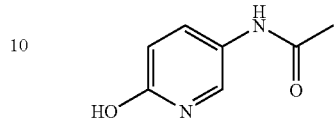

D. N-(6-Hydroxy-3-pyridinyl)acetamide

To a solution of N-{6-[(phenylmethyl)oxy]-3-pyridinyl}acetamide (0.210 g, 0.87 mmol) in EtOH (10 mL) at rt was added Pd—C (0.046 g of 10 wt % on activated carbon (dry basis), ca. 50 wt % $H_2O$; ca. 0.022 mmol Pd). The mixture was placed under an atmosphere of $H_2$ and stirred for 4.5 h. The mixture was filtered through Celite (EtOAc wash) and concentrated in vacuo, affording 0.132 g of the title compound as a colorless solid: MS (ESI) m/z 152 (M$^+$).

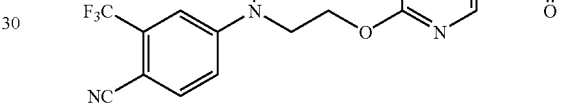

E. N-[6-({2-[[4-Cyano-3-(trifluoromethyl)phenyl](2,2,2-trifluoroethyl)amino]ethyl}oxy)-3-pyridinyl]acetamide Synthesized as described in Example 27B from 4-[(2-hydroxyethyl)(2,2,2-trifluoroethyl)amino]-2-(trifluoromethyl)benzonitrile (Example 15B) and N-(6-hydroxy-3-pyridinyl)acetamide, using dry DME as the reaction solvent: MS (ESI) m/z 447 (M+1).

Example 54

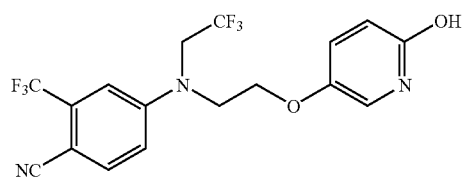

4-[{2-[(6-Oxo-1,6-dihydro-3-pyridinyl)oxy]ethyl}(2,2,2-trifluoroethyl)amino]-2-(trifluoromethyl)benzonitrile

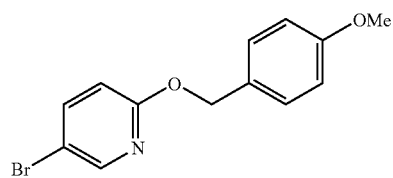

A. 5-Bromo-2-({[4-(methyloxy)phenyl]methyl}oxy) pyridine

Synthesized as described in Example 53A from 2,5-dibromopyridine and p-methoxybenzyl alcohol with the following exceptions: the reaction was heated at reflux for 90 min, and the title compound was purified by flash chromatography (EtOAc/hexanes): $^1$H NMR (400 MHz, CDCl$_3$) δ 8.21 (dd, J=2.6, 0.6 Hz, 1H), 7.64 (dd, J=8.8, 2.6 Hz, 1H), 7.38 (m, 2H, AA'XX'), 6.91 (m, 2H, AA'XX'), 6.69 (dd, J=8.9, 0.6 Hz, 1H), 5.26 (s, 2H), 3.81 (s, 3H).

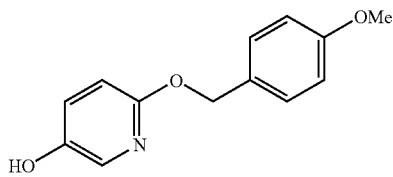

B. 6-({[4-(Methyloxy)phenyl]methyl}oxy)-3-pyridinol

Synthesized as described in Example 51A from 5-bromo-2-({[4-(methyloxy)phenyl]methyl}oxy)pyridine (step A above): MS (APCI) m/z 230 (M−1).

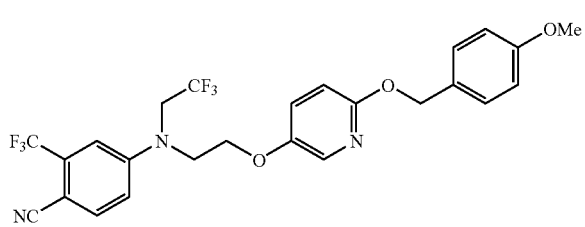

C. 4-[(2-{[6-({[4-(Methyloxy)phenyl]methyl}oxy)-3-pyridinyl]oxy}ethyl)(2,2,2-trifluoroethyl)amino]-2-(trifluoromethyl)benzonitrile Synthesized as described in Example 27B from 4-[(2-hydroxyethyl)(2,2,2-trifluoroethyl)amino]-2-(trifluoromethyl)benzonitrile (Example 15B) and 6-({[4-(methyloxy)phenyl]methyl}oxy)-3-pyridinol (step B above) with the following exceptions: PPh$_3$ was used instead of PBu$_3$, and the reaction was started at 0° C., then allowed to proceed at rt: $^1$H NMR (400 MHz, CDCl$_3$) δ 7.76 (d, J=3.3 Hz, 1H), 7.68 (d, J=8.9 Hz, 1H), 7.37 (m, 2H; AA'XX'), 7.18 (d, J=2.7 Hz, 1H), 7.15 (dd, J=8.9, 3.1 Hz, 1H), 7.00 (dd, J=8.9, 2.7 Hz, 1H), 6.90 (m, 2H; AA'XX'), 6.72 (d, J=8.9 Hz, 1H), 5.23 (s, 2H), 4.20 (t, J=5.1 Hz, 2H; overlapping 4.19), 4.19 (q, J=8.6 Hz, 2H; overlapping 4.20), 3.99 (t, J=5.2 Hz, 2H), 3.81 (s, 3H).

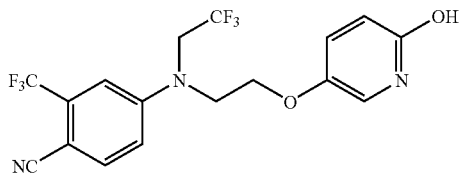

D. 4-[{2-[(6-Oxo-1,6-dihydro-3-pyridinyl)oxy]ethyl}(2,2,2-trifluoroethyl)amino]-2-(trifluoromethyl)benzonitrile A mixture of 4-[(2-{[6-({[4-(methyloxy)phenyl]methyl}oxy)-3-pyridinyl]oxy}ethyl)(2,2,2-trifluoroethyl)amino]-2-(trifluoromethyl)benzonitrile (0.270 g, 0.51 mmol; step C above) and Pd—C (0.027 g of 10 wt % on activated carbon (dry basis), ca. 50 wt % H$_2$O, ca. 0.013 mmol Pd) was stirred under an atmosphere of H$_2$ for 45 min and filtered through Celite. The filtrate was adsorbed onto a small amount of silica gel and purified by flash chromatography (MeOH/CH$_2$Cl$_2$), affording 0.160 g of the title compound as a colorless solid: MS (ESI) 406 (M+1).

Example 55

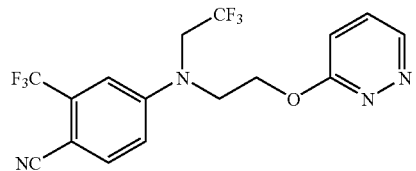

4-[[2-(3-Pyridazinyloxy)ethyl](2,2,2-trifluoroethyl)amino]-2-(trifluoromethyl)benzonitrile Synthesized as described in Example 27B from 4-[(2-hydroxyethyl)(2,2,2-trifluoroethyl)amino]-2-(trifluoromethyl)benzonitrile (Example 15B) and 3-hydroxypyridazine, using dry DME as the reaction solvent: MS (ESI) m/z 391 (M+1).

Example 56

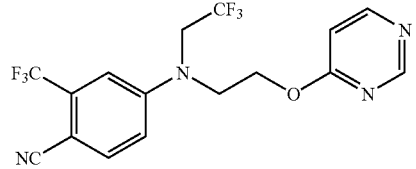

4-[[$^2$-(4-Pyrimidinyloxy)ethyl](2,2,2-trifluoroethyl)amino]-2-(trifluoromethyl)benzonitrile Synthesized as described in Example 27B from 4-[(2-hydroxyethyl)(2,2,2-trifluoroethyl)amino]-2-(trifluoromethyl)benzonitrile (Example 15B) and 4(1H)-pyrimidinone, using dry DME as the reaction solvent: MS (ESI) m/z 391 (M+1).

Example 57

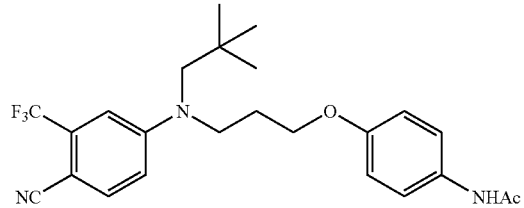

N-[4-({3-[[4-Cyano-3-(trifluoromethyl)phenyl](2,2-dimethylpropyl)amino]propyl}oxy)phenyl]acetamide Example 58

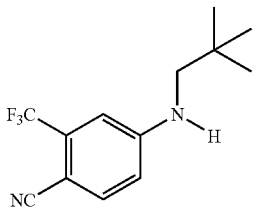

A. 4-[(2,2-Dimethylpropyl)amino]-2-(trifluoromethyl)benzonitrile

Synthesized as described in Example 1A from 4-fluoro-2-(trifluoromethyl)benzonitrile and neopentylamine: MS (El) m/z 256 (M⁺, 9%), 239 ({[M–H]—CH₃}⁺, 32%), 199 ([M-ᵗbutyl]⁺, 78%), 179 ([M-neopentylamine]⁺, 100).

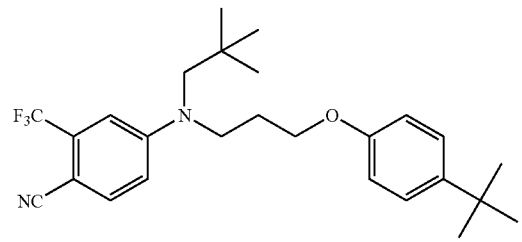

4-[(3-{[4-(1,1-Dimethylethyl)phenyl]oxy}propyl)(2,2-dimethylpropyl)amino]-2-(trifluoromethyl)benzonitrile Synthesized as described in Example 1C from 4-[(2,2-dimethylpropyl)(3-hydroxypropyl)amino]-2-(trifluoromethyl)benzonitrile and 4-tert-butylphenol: MS (ESI) m/z 447 (M+1).

Example 59

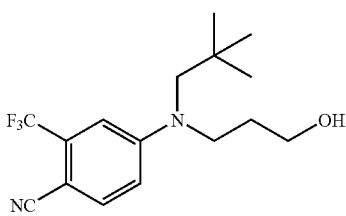

B. 4-[(2,2-Dimethylpropyl)(3-hydroxypropyl)amino]-2-(trifluoromethyl)benzonitrile Synthesized as described in Example 1B from 4-[(2,2-dimethylpropyl)amino]-2-(trifluoromethyl)benzonitrile and [(3-bromopropyl)oxy](1,1-dimethylethyl)dimethylsilane: ¹H NMR (300 MHz, CDCl₃) δ 7.53 (d, J=8.9 Hz, 1H), 7.05 (d, J=2.5 Hz, 1H), 6.87 (dd, J=8.9, 2.5 Hz, 1H), 3.70 (app. bq, J=4.7 Hz, 2H), 3.62 (app. t, J=7.3 Hz, 2H), 3.27 (s, 2H), 1.87-1.75 (m, 2H), 1.47 (bt, J=4.2 Hz, 1H), 0.99 (s, 9H).

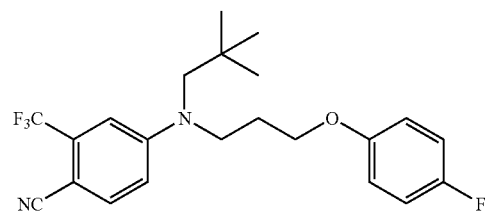

4-((2,2-Dimethylpropyl){3-[(4-fluorophenyl)oxy]propyl}amino)-2-(trifluoromethyl)benzonitrile Synthesized as described in Example 1C from 4-[(2,2-dimethylpropyl)(3-hydroxypropyl)amino]-2-(trifluoromethyl)benzonitrile and 4-fluorophenol: MS (ESI) m/z 409 (M+1).

Example 60

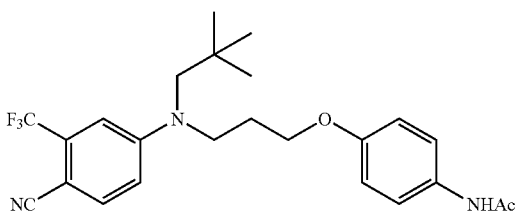

C. N-[4-({3-[[4-Cyano-3-(trifluoromethyl)phenyl](2,2-dimethylpropyl)amino]propyl}oxy)phenyl]acetamide Synthesized as described in Example 1C from 4-[(2,2-dimethylpropyl)(3-hydroxypropyl)amino]-2-(trifluoromethyl)benzonitrile and 4-acetamidophenol: MS (ESI) m/z 448 (M+1).

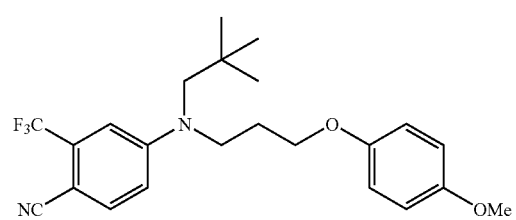

4-[(2,2-Dimethylpropyl)(3-{[4-(methyloxy)phenyl]oxy}propyl)amino]-2-(trifluoromethyl)benzonitrile Synthesized as described in Example 1C from 4-[(2,2-dimethylpropyl)(3-hydroxypropyl)amino]-2-(trifluoromethyl)benzonitrile and 4-methoxyphenol: MS (ESI) m/z 421 (M+1).

Example 61

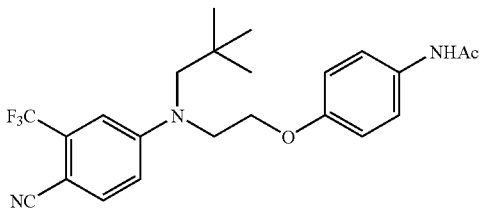

N-[4-({2-[[4-Cyano-3-(trifluoromethyl)phenyl](2,2-dimethylpropyl)amino]ethyl}oxy)phenyl]acetamide

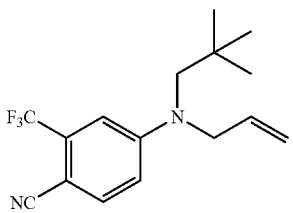

A. 4-[(2,2-Dimethylpropyl)(2-propen-1-yl)amino]-2-(trifluoromethyl)benzonitrile To a slurry of hexanes-washed NaH (0.534 g of a 60% w/w suspension in mineral oil; 13.4 mmol) in dry DMF (10 mL) at 0° C., under $N_2$, was added a solution of 4-[(2,2-dimethylpropyl)amino]-2-(trifluoromethyl)benzonitrile (1.71 g, 6.68 mmol, step A, Example 57) in DMF (4 mL), dropwise over 10 min. The mixture was stirred 15 min and allyl bromide (1.16 mL, 13.4 mmol) was added dropwise over 3 min. The mixture was stirred 1 h at 0° C. and poured into water. The whole was extracted with $Et_2O$ (×3). The combined organic portions were washed (water, brine), dried over $Na_2SO_4$, filtered and concentrated in vacuo. The residue was purified by flash chromatography (EtOAc/hexanes), affording 1.82 g of the title compound as a colorless syrup that slowly solidified: MS (EI) m/z 296 ($M^+$, 9%), 239 ([M-$^t$Bu]$^+$, 100%), 197 (83%), 170 (99%).

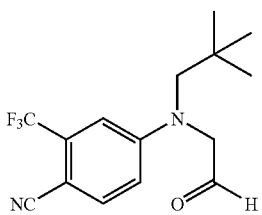

B. 4-[(2,2-Dimethylpropyl)(2-oxoethyl)amino]-2-(trifluoromethyl)benzonitrile To a solution of 4-[(2,2-dimethylpropyl)(2-propen-1-yl)amino]-2-(trifluoromethyl)benzonitrile (1.46 g, 4.95 mmol) in THF/water (20:1, 45 mL) at rt was added a solution of $OsO_4$ (0.025 g, 0.1 mmol) in THF/water (5 mL) followed by NMO (1.22 g; 10.4 mmol) in one portion. The mixture was stirred 22 h, cooled to 0° C. and sodium bisulfite (0.300 g) was added and the cooling bath removed. The mixture was stirred 1 h at rt, filtered through a pad of Celite, partitioned between EtOAc/water, and the layers were separated. The aqueous layer was extracted with EtOAc (×1). Combined organic portions were washed (water, brine), dried over $Na_2SO_4$, filtered, and concentrated in vacuo, affording 1.83 g of a pale orange oil which was used without further purification. The oil was dissolved in acetone (50 mL), and to the solution was added a solution of $NaIO_4$ (2.22 g, 10.4 mmol) in water (20 mL) over 10 min. The mixture was stirred 2 h and partially concentrated in vacuo to an aqueous residue. The residue was partitioned between EtOAc/water and the layers were separated. The aqueous layer was extracted with EtOAc (×1). Combined organic portions were washed (water, brine), dried over $Na_2SO_4$ and concentrated in vacuo. The residue was purified by flash chromatography (EtOAc/hexanes), affording 1.20 g of the title compound as a colorless solid: $^1$H NMR (400 MHz, $CDCl_3$) δ 9.70 (s, 1H), 7.57 (d, J=8.8 Hz, 1H), 6.96 (d, J=2.5 Hz, 1H), 6.74 (dd, J=8.9, 2.7 Hz, 1H), 4.31 (s, 2H), 3.33 (s, 2H), 1.02 (s, 9H).

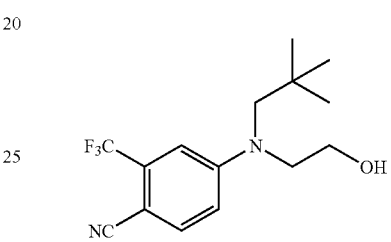

C. 4-[(2,2-Dimethylpropyl)(2-hydroxyethyl)amino]-2-(trifluoromethyl)benzonitrile To a solution of 4-[(2,2-dimethylpropyl)(2-oxoethyl)amino]-2-(trifluoromethyl)benzonitrile (0.882 g, 2.96 mmol) in MeOH (10 mL) at 0° C. was added $NaBH_4$ (0.112 g, 2.96 mmol) in one portion and the mixture was stirred overnight, slowly warming to rt. The mixture was cooled to 0° C., sat'd $NH_4Cl$ (1 mL) was added and the mixture was concentrated in vacuo. The residue was partitioned between EtOAc/water and the layers were separated. The organic layer was washed with brine, dried over $Na_2SO_4$, filtered and concentrated in vacuo. The residue was purified by flash chromatography (EtOAc/hexanes), affording 0.829 g of the title compound as a colorless syrup which solidified on standing: MS (ESI) m/z 301 (M+1).

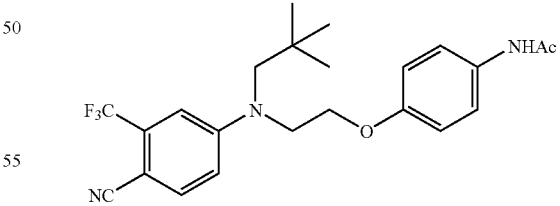

D. N-[4-({2-[[4-Cyano-3-(trifluoromethyl)phenyl](2,2-dimethylpropyl)amino]ethyl}oxy)phenyl]acetamide Synthesized as described in Example 1C from 4-[(2,2-dimethylpropyl)(2-hydroxyethyl)amino]-2-(trifluoromethyl)benzonitrile and 4-acetamidophenol: MS (ESI) m/z 434 (M+1).

Example 62

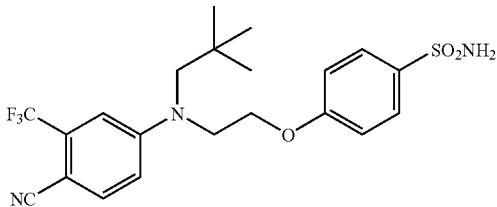

4-({2-[[4-Cyano-3-(trifluoromethyl)phenyl](2,2-dimethylpropyl)amino]ethyl}oxy)benzenesulfonamide Synthesized as described in Example 1C from 4-[(2,2-dimethylpropyl)(2-hydroxyethyl)amino]-2-(trifluoromethyl)benzonitrile and 4-hydroxybenzenesulfonamide: MS (APCI) m/z 454 (M−1).

Example 63

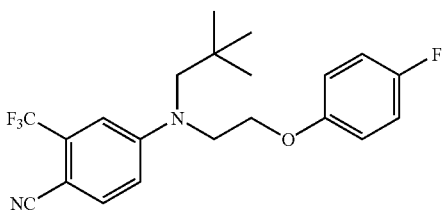

4-((2,2-Dimethylpropyl){2-[(4-fluorophenyl)oxy]ethyl}amino)-2-(trifluoromethyl)benzonitrile Synthesized as described in Example 1C from 4-[(2,2-dimethylpropyl)(2-hydroxyethyl)amino]-2-(trifluoromethyl)benzonitrile and 4-fluorophenol: $^1$H NMR (400 MHz, CDCl$_3$) δ 7.55 (d, J=8.8 Hz, 1H), 7.10 (d, J=2.4 Hz, 1H), 6.99-6.93 (m, 2H, partially overlapping 6.91), 6.91 (dd, J=8.9, 2.3 Hz, 1H), 6.80-6.73 (m, 2H), 4.07 (t, J=5.7 Hz, 2H), 3.92 (t, J=5.7 Hz, 2H), 3.40 (s, 2H), 1.01 (s, 9H).

Example 64

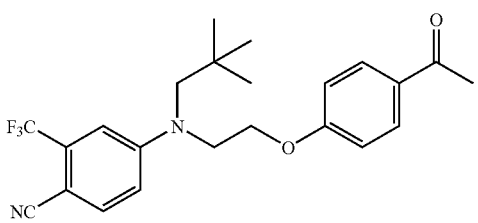

4-[{2-[(4-Acetylphenyl)oxy]ethyl}(2,2-dimethylpropyl)amino]-2-(trifluoromethyl)benzonitrile Synthesized as described in Example 1C from 4-[(2,2-dimethylpropyl)(2-hydroxyethyl)amino]-2-(trifluoromethyl)benzonitrile and 4-hydroxyacetophenone: $^1$H NMR (400 MHz, CDCl$_3$) δ 7.91 (d, J=8.5 Hz, 2H), 7.57 (d, J=8.8 Hz, 1H), 7.11 (app. s, 1H), 6.92 (app. bd, J=8.9 Hz, 1H), 6.86 (d, J=8.5 Hz, 2H), 4.18 (t, J=5.6 Hz, 2H), 3.96 (t, J=5.6 Hz, 2H), 3.41 (s, 2H), 2.55 (s, 3H), 1.02 (s, 9H).

Example 65

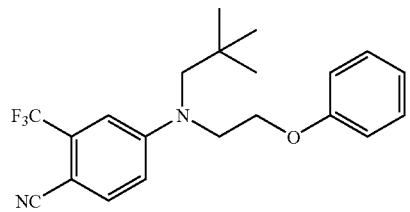

4-{(2,2-Dimethylpropyl)[2-(phenyloxy)ethyl]amino}-2-(trifluoromethyl)benzonitrile Synthesized as described in Example 1C from 4-[(2,2-dimethylpropyl)(2-hydroxyethyl)amino]-2-(trifluoromethyl)benzonitrile and phenol: $^1$H NMR (400 MHz, CDCl$_3$) δ 7.55 (d, J=9.0 Hz, 1H), 7.31-7.23 (m, 2H), 7.11 (d, J=2.2 Hz, 1H), 6.69 (app. t, J=7.3 Hz, 1H), 6.91 (dd, J=8.9, 2.4 Hz, 1H), 6.83 (d, J=8.2 Hz, 2H), 4.11 (t, J=5.7 Hz, 2H), 3.93 (t, J=5.7 Hz, 2H), 3.40 (s, 2H), 1.01 (s, 9H).

Example 66

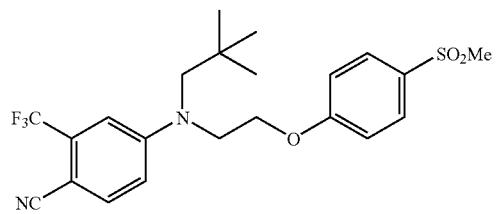

4-[(2,2-Dimethylpropyl)(2-{[4-(methylsulfonyl)phenyl]oxy}ethyl)amino]-2-(trifluoromethyl)benzonitrile Synthesized as described in Example 1C from 4-[(2,2-dimethylpropyl)(2-hydroxyethyl)amino]-2-(trifluoromethyl)benzonitrile and 4-methanesulfonylphenol: MS (ESI) m/z 455 (M+1).

Example 67

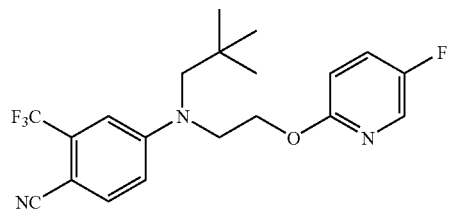

4-((2,2-Dimethylpropyl){2-[(5-fluoro-2-pyridinyl)oxy]ethyl}amino)-2-(trifluoromethyl)benzonitrile Synthesized as described in Example 27B from 4-[(2,2-dimethylpropyl)(2-hydroxyethyl)amino]-2-(trifluoromethyl)benzonitrile (Example 61C) and 5-fluoro-2(1H)-pyridinone: $^1$H NMR (400 MHz, CDCl$_3$) δ 7.97 (d, J=3.0 Hz, 1H), 7.55 (d, J=8.8 Hz, 1H), 7.35 (m, 1H), 7.27 (d, J=2.7 Hz, 1H; partially obscured by solvent), 6.96-(dd, J=9.0, 2.7 Hz, 1H), 6.66 (ddd, J=9.1, 3.6, 0.6 Hz, 1H), 4.41 (t, J=6.7 Hz, 2H), 3.87 (t, J=6.7 Hz, 2H), 3.33 (s, 2H), 1.00 (s, 9H).

Example 68

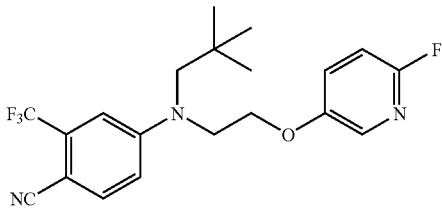

4-((2,2-Dimethylpropyl){2-[(6-fluoro-3-pyridinyl)oxy]ethyl}amino)-2-(trifluoromethyl)benzonitrile Synthesized as described in Example 27B from 4-[(2,2-dimethylpropyl)(2-hydroxyethyl)amino]-2-(trifluoromethyl)benzonitrile (Example 61C) and 6-fluoro-3-pyridinol (Example 51A) with the following exceptions: additional portions of ADDP and PBu$_3$ (0.5 equiv ea) were added to the reaction mixture after 1 h, the reaction was stirred for 60 h, and the title compound was purified by flash chromatography (EtOAc/hexanes) followed by RP-HPLC (MeCN/H$_2$O+0.1% TFA): MS (ESI) m/z 396 (M+1).

Example 69

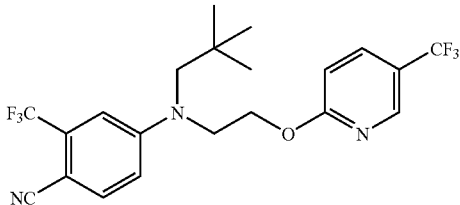

4-[(2,2-Dimethylpropyl)(2-{[5-(trifluoromethyl)-2-pyridinyl]oxy}ethyl)amino]-2-(trifluoromethyl)benzonitrile Synthesized as described in Example 27B from 4-[(2,2-dimethylpropyl)(2-hydroxyethyl)amino]-2-(trifluoromethyl)benzonitrile (Example 61C) and 5-(trifluoromethyl)-2(1H)-pyridinone, using dry DME as the reaction solvent: $^1$H NMR (400 MHz, CDCl$_3$) δ 8.43 (m, 1H), 7.79 (app. dd, J=8.8, 2.6 Hz, 1H), 7.56 (d, J=8.9 Hz, 1H), 7.27 (d, J≈2.6 Hz, 1H; partially obscured by solvent), 6.97 (dd, J=9.0, 2.8 Hz, 1H), 6.78 (partially resolved ddd, J=8.7, ~0.6, ~0.6 Hz, 1H), 4.52 (t, J=6.6 Hz, 2H), 3.90 (t, J=6.7 Hz, 2H), 3.34 (s, 2H), 1.00 (s, 9H).

Example 70

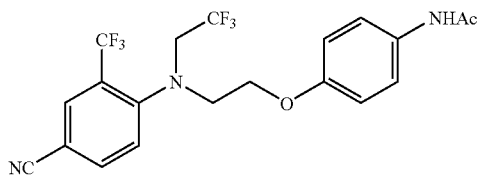

N-[4-({2-[[4-Cyano-2-(trifluoromethyl)phenyl](2,2,2-trifluoroethyl)amino]ethyl}oxy)phenyl]acetamide

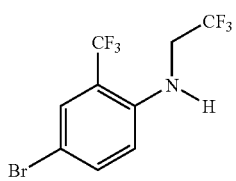

A. 4-Bromo-N-(2,2,2-trifluoroethyl)-2-(trifluoromethyl)aniline

Synthesized as described in Example 11A from 4-bromo-2-(trifluoromethyl)aniline, purified by flash chromatography (EtOAc/hexanes), obtained as an orange oil: MS (ESI) m/z 323 (M$^+$, $^{81}$Br, 59%), 321 (M$^+$, $^{79}$Br, 81%), 254 ([M-CF$_3$]$^+$, $^{81}$Br, 42%), 252 ({[M-H]—HCF$_3$}$^+$, $^{81}$Br and [M-CF$_3$]$^+$, $^{79}$Br, 100%), 250 ({[M-H]—HCF$_3$}$^+$, $^{79}$Br, 67%).

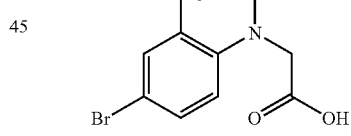

B. N-[4-Bromo-2-(trifluoromethyl)phenyl]-N-(2,2,2-trifluoroethyl)glycine

To a slurry of hexanes-washed NaH (0.492 g of a 60% w/w suspension in mineral oil, 12.3 mmol) in dry DMF (10 mL) at 0° C. was added a solution of 4-bromo-N-(2,2,2-trifluoroethyl)-2-(trifluoromethyl)aniline (1.96 g, 6.13 mmol) in DMF (2 mL), dropwise over 5 min. The mixture was stirred 15 min and tert-butyl bromoacetate (1.82 mL, 12.3 mmol) was added dropwise over 1 min. The mixture was stirred overnight, slowly warming to rt. The mixture was poured into water and the whole was extracted with Et$_2$O (×3). Combined organic portions were washed (water, brine), dried over Na$_2$SO$_4$, filtered and concentrated. The residue was dissolved in CH$_2$Cl$_2$ (20 mL) and to this solution was added Et$_3$SiH (4.9 mL, 31 mmol) and TFA (20 mL). The mixture was stirred 1.5 h at rt and concentrated in vacuo. The residue was partitioned between water/Et₂O and the layers were separated. The organic layer was concentrated in vacuo. The residue was purified by filtration through a pad of silica gel (10% EtOAc/hexanes, then EtOAc to elute carboxylic acid) affording 1.50 g of the title compound as a pale yellow solid: MS (APCI) m/z 380 ([M–H]⁻, ⁸¹Br), 378 ([M–H]⁻, ⁷⁹Br).

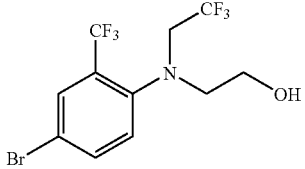

C. 2-[[4-Bromo-2-(trifluoromethyl)phenyl](2,2,2-trifluoroethyl)amino]ethanol To a solution of N-[4-bromo-2-(trifluoromethyl)phenyl]-N-(2,2,2-trifluoroethyl)glycine (1.50 g, 3.95 mmol) in dry THF (10 mL) at 0° C., under N₂, was added a solution of BH₃/THF in THF (6.6 mL, 1.8 M, 12 mmol), dropwise over 3 min. The cooling bath was removed and the mixture was stirred at rt. After 23 h, an additional portion of BH₃/THF (2.2 mL, 4 mmol) was added and stirring was continued another 6 h. The mixture was cooled to 0° C., quenched by dropwise addition of 10% v/v HCl and poured into water and extracted with EtOAc (×3). Combined organic portions were washed (water, brine), dried over Na₂SO₄, filtered, and concentrated in vacuo. The residue was purified by flash chromatography (EtOAc/hexanes), affording 1.17 g of the title compound as a colorless syrup: ¹H NMR (300 MHz, CD₃OD) δ 7.81-7.73 (m, 2H), 7.55 (d, J=8.2 Hz, 1H), 3.89 (q, J=9.3 Hz, 2H), 3.61 (t, J=6.2 Hz, 2H), 3.24 (t, J=6.1 Hz, 2H).

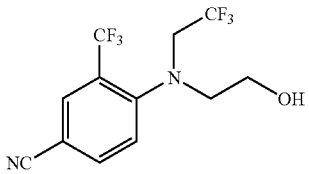

D. 4-[(2-Hydroxyethyl)(2,2,2-trifluoroethyl)amino]-3-(trifluoromethyl)benzonitrile A mixture of 2-[[4-bromo-2-(trifluoromethyl)phenyl](2,2,2-trifluoroethyl)amino]ethanol (0.699 g, 1.92 mmol) and Zn(CN)₂ (0.157 g, 1.34 mmol) in DMF (5 mL) was sparged with N₂ for 15 min at rt and Pd(PPh₃)₄ (0.111 g, 0.096 mmol) was added in one portion, taking care not to allow air into the reaction flask. The mixture was heated to 80° C. under N₂ for 40 min, cooled, poured into dilute NH₄OH, and the whole was extracted with Et₂O (×3). The combined organic portions were washed (water, brine), dried over Na₂SO₄, filtered and concentrated in vacuo. The residue was purified by flash chromatography (EtOAc/hexanes), affording 0.571 g of the title compound as a colorless gum: ¹H NMR (300 MHz, CDCl₃) δ 7.97 (d, J=1.6 Hz, 1H), 7.82 (dd, J=8.4, 1.8 Hz, 1H), 7.56 (d, J=8.6 Hz, 1H), 3.86 (q, J=8.9 Hz, 2H), 3.69 (t, J=2H), 3.50 (t, J=5.2 Hz, 2H), 1.74 (bs, 1H).

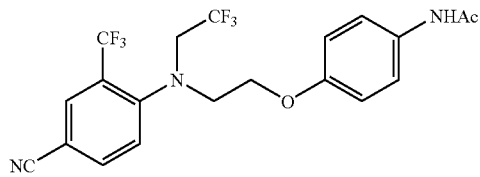

E. N-[4-({2-[[4-Cyano-2-(trifluoromethyl)phenyl](2,2,2-trifluoroethyl)amino]ethyl}oxy)phenyl]acetamide Synthesized as described in Example 1C from 4-[(2-hydroxyethyl)(2,2,2-trifluoroethyl)amino]-3-(trifluoromethyl)benzonitrile and 4-acetamidophenol: MS (APCI) m/z 446 (M+1).

Example 71

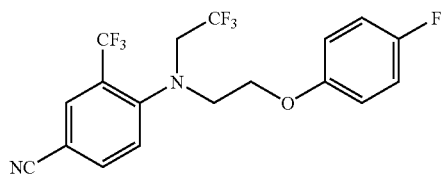

4-[{2-[(4-Fluorophenyl)oxy]ethyl}(2,2,2-trifluoroethyl)amino]-3-(trifluoromethyl)benzonitrile Synthesized as described in Example 1C from 4-[(2-hydroxyethyl)(2,2,2-trifluoroethyl)amino]-3-(trifluoromethyl)benzonitrile and 4-fluorophenol: MS (APCI) m/z 407 (M+1).

Example 72

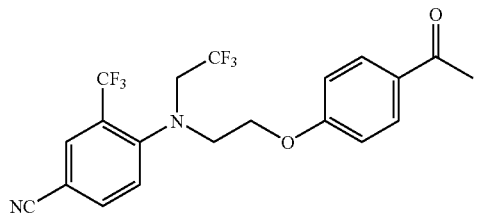

4-[{2-[(4-Acetylphenyl)oxy]ethyl}(2,2,2-trifluoroethyl)amino]-3-(trifluoromethyl)benzonitrile Synthesized as described in Example 1C from 4-[(2-hydroxyethyl)(2,2,2-trifluoroethyl)amino]-3-(trifluoromethyl)benzonitrile and 4-hydroxyacetophenone: MS (APCI) m/z 431 (M+1).

Example 73

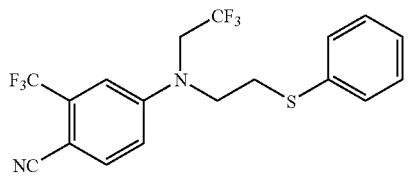

4-[[2-(Phenylthio)ethyl](2,2,2-trifluoroethyl)amino]-2-(trifluoromethyl)benzonitrile A solution of 4-[(2-hydroxyethyl)(2,2,2-trifluoroethyl)amino]-2-(trifluoromethyl)benzonitrile (0.060 g, 0.19 mmol) in THF (2 mL) was treated with phenyidisulfide (0.168 g, 0.77 mmol) and tributylphosphine (0.156 g, 0.77 mmol) and stirred at rt for 3 h. The mixture was partitioned between EtOAc and 0.5N NaOH. The organic phase was washed with 0.5N NaOH and brine, dried (Na$_2$SO$_4$), and concentrated in vacuo. The residue was purified by silica gel chromatography (5-30% EtOAc/hexanes gradient) to give the title compound (0.072 g, 93%): MS (ES) m/z 405 (M+1).

Example 74

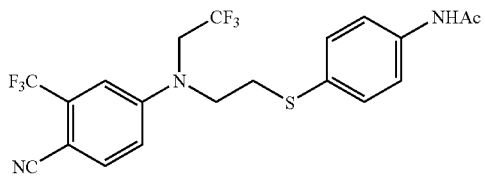

N-[4-({2-[[4-Cyano-3-(trifluoromethyl)phenyl](2,2,2-trifluoroethyl)amino]ethyl}thio)phenyl]acetamide

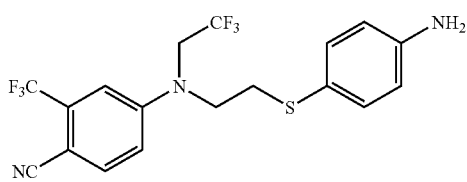

A. 4-[{2-[(4-Aminophenyl)thio]ethyl}(2,2,2-trifluoroethyl)amino]-2-(trifluoromethyl)benzonitrile A solution of 4-[(2-hydroxyethyl)(2,2,2-trifluoroethyl)amino]-2-(trifluoromethyl)benzonitrile (0.100 g, 0.32 mmol) in THF (5 mL) was treated with 4-aminophenyidisulfide (0.318 g, 1.28 mmol) and tributylphosphine (0.259 g, 1.28 mmol) and stirred at rt for 3 hr. The mixture was partitioned between EtOAc and 0.5N NaOH. The organic phase was washed with 0.5N NaOH and brine, dried (Na$_2$SO$_4$), and concentrated in vacuo. The residue was purified by silica gel chromatography (2-60% EtOAc/hexanes gradient) to give the title compound (0.110 g, 75%): $^1$H NMR (400 MHz, CDCl$_3$) δ 7.53 (d, J=8.8 Hz, 1H), 7.26 (d, J=8.1 Hz, 2H), 6.84 (d, J=2.4 Hz, 1H), 6.70-6.60 (m, 3H), 3.94 (q, J=8.4 Hz, 2H), 3.64 (t, J=7.7 Hz, 2H), 2.90 (t, J=7.7 Hz, 2H).

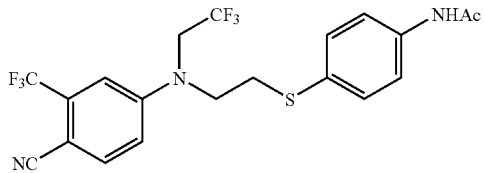

B. N-[4-({2-[[4-Cyano-3-(trifluoromethyl)phenyl](2,2,2-trifluoroethyl)amino]ethyl}thio)phenyl]acetamide A solution of Example 74A (0.110 g, 0.26 mmol) in CH$_2$Cl$_2$ (4 mL) was treated with TEA (0.029 g, 0.29 mmol) and acetic anhydride (0.030 g, 0.29 mmol) under N$_2$, and stirred at rt. After 5 h, additional TEA (0.004 g, 0.039 mmol) and acetic anhydride (0.004 g, 0.039 mmol) were added and stirred at rt for 12 h. The mixture was concentrated in vacuo and partitioned between EtOAc and 0.1N HCl. The organic phase was washed with 0.1N HCl and brine, dried (Na$_2$SO$_4$), and concentrated in vacuo. The residue was purified by silica gel chromatography (5-80% EtOAc/hexanes gradient) and the product crystallized from CH$_2$Cl$_2$/hexanes to give the title compound as a white solid (0.104 g, 86% yield): MS (ES) m/z 462 (M+1).

Example 75

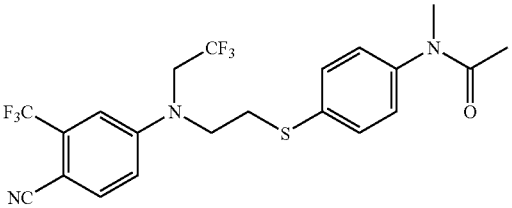

N-[4-({2-[[4-Cyano-3-(trifluoromethyl)phenyl](2,2,2-trifluoroethyl)amino]ethyl}thio)phenyl]-N-methylacetamide NaH (60% in oil, 0.003 g, 0.075 mmol) was added to a solution of N-[4-({2-[[4-cyano-3-(trifluoromethyl)phenyl](2,2,2-trifluoroethyl)amino]ethyl}thio)phenyl]acetamide (0.026 g, 0.056 mmol) in DMF (2 mL) under N$_2$. After 5 min, iodomethane (0.009 g, 0.063 mmol) was added and stirred at rt for 30 min. The mixture was partitioned between Et$_2$O and water. The organic phase was washed with water and brine, dried (Na$_2$SO$_4$), and concentrated in vacuo. The residue was purified by silica gel chromatography (5-80% EtOAc/hexanes gradient) to give the title compound (0.018 mg, 66% yield): MS (ES) m/z 476 (M+1).

Example 76

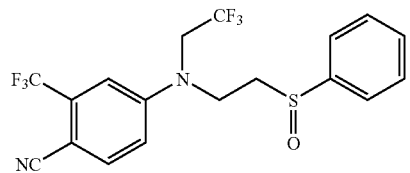

4-[[2-(Phenylsulfinyl)ethyl](2,2,2-trifluoroethyl)amino]-2-(trifluoromethyl)benzonitrile To a solution of 4-[[2-(phenylthio)ethyl](2,2,2-trifluoroethyl)amino]-2-(trifluoromethyl)benzonitrile (0.039 g, 0.096 mmol) in MeOH (3 mL) was added a solution of NaIO$_4$ (0.041 g, 0.193 mmol) in water (1 mL) and stirred at rt. After 1 h, additional NaIO$_4$ (0.041 g, 0.19 mmol) dissolved in water (1 mL) was added and the reaction mixture diluted with MeOH (1 mL). After stirring at rt for 12 h, the mixture was partitioned between EtOAc and brine. The organic phase was washed with water and brine, dried ($Na_2SO_4$) and concentrated in vacuo. The residue was purified by silica gel chromatography (1-10% MeOH/$CH_2Cl_2$ gradient) to give the title compound (0.037 g, 88% yield): MS (ES) m/z 421 (M+1).

Example 77

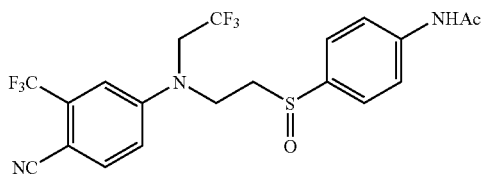

N-[4-({2-[[4-Cyano-3-(trifluoromethyl)phenyl](2,2,2-trifluoroethyl)amino]ethyl}sulfinyl)phenyl]acetamide Similarly prepared using N-[4-({2-[[4-cyano-3-(trifluoromethyl)phenyl](2,2,2-trifluoroethyl)amino]ethyl}thio)phenyl]acetamide: MS (ES) m/z 478 (M+1).

Example 78

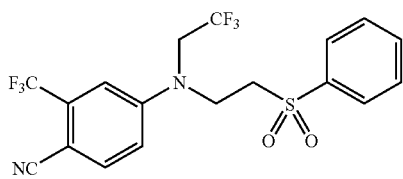

4-[[2-(Phenylsulfonyl)ethyl](2,2,2-trifluoroethyl)amino]-2-(trifluoromethyl)benzonitrile An ice-cold solution of 4-[[2-(phenylthio)ethyl](2,2,2-trifluoroethyl)amino]-2-(trifluoromethyl)benzonitrile (0.056 g, 0.138 mmol) in MeOH (6 mL) was treated with a solution of oxone (0.255 g, 0.415 mmol) in water (3 mL) and stirred at rt. After 1.5 h, the mixture was partitioned between EtOAc and water. The organic phase was washed with water and brine, dried ($Na_2SO_4$) and concentrated in vacuo. The residue was purified by silica gel chromatography (5-50% EtOAc/hexanes gradient) and the product crystallized from $CH_2Cl_2$/hexanes to give the title compound as a white solid (0.057 g, 95% yield): MS (ES) m/z 437 (M+1).

Example 79

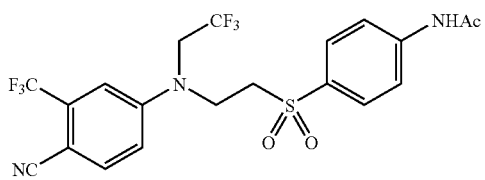

N-[4-({2-[[4-Cyano-3-(trifluoromethyl)phenyl](2,2,2-trifluoroethyl)amino]ethyl}sulfonyl)phenyl]acetamide Similarly prepared using N-[4-({2-[[4-cyano-3-(trifluoromethyl)phenyl](2,2,2-trifluoroethyl)amino]ethyl}thio)phenyl]acetamide: MS (ES) m/z 494 (M+1).

Example 80

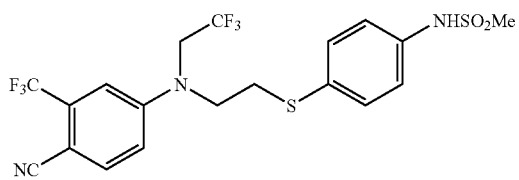

N-[4-({2-[[4-Cyano-3-(trifluoromethyl)phenyl](2,2,2-trifluoroethyl)amino]ethyl}thio)phenyl]methanesulfonamide A solution of 4-[{2-[(4-aminophenyl)thio]ethyl}(2,2,2-trifluoroethyl)amino]-2-(trifluoromethyl)benzonitrile (0.038 g, 0.091 mmol; see Example 74A) in $CH_2Cl_2$ (4 mL) was treated under $N_2$ with TEA (0.010 g, 0.099 mmol) and MsCl (0.011 g, 0.099 mmol) and stirred at rt. After 4 h, additional TEA (0.0046 g, 0.046 mmol) and MsCl (0.0052 g, 0.046 mmol) were added and stirred at rt. After 1 h, the mixture was concentrated in vacuo and the residue taken up in $CHCl_3$ (4 mL) and heated at 70° C. for 2 h. Upon cooling, additional TEA (0.0046 g, 0.046 mmol) and MsCl (0.0052 g, 0.046 mmol) were added and heated at 70° C. for 12 h. Upon cooling, additional TEA (0.0092 g, 0.091 mmol) and MsCl (0.0104 g, 0.091 mmol) were added and heated at 70° C. for 4 h. The mixture was partitioned between EtOAc and 0.1N HCl. The organic phase was washed with 0.1N HCl and brine, dried ($Na_2SO_4$) and concentrated in vacuo. The residue was purified by silica gel chromatography (5-80% EtOAc/hexanes gradient) to give the title compound (0.025 g, 55% yield): MS (ES) m/z 496 (M−1).

Example 81

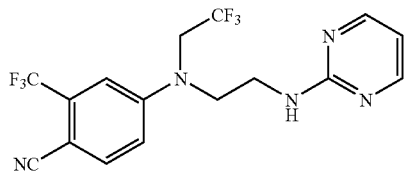

4-[[2-(Pyrimidin-2-ylamino)ethyl](2,2,2-trifluoroethyl)amino]-2-(trifluoromethyl)benzonitrile

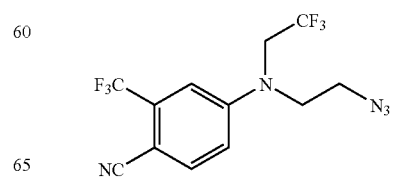

A. 4-[(2-Azidoethyl)(2,2,2-trifluoroethyl)amino]-2-(trifluoromethyl)benzonitrile A mixture of Example 15C (0.195 g, 0.50 mmol) and sodium azide (0.065 g, 1.0 mmol) in DMF (5 mL) was heated at 85° C., under $N_2$, for 45 min. Upon cooling, the mixture was partitioned between $Et_2O$ and water. The organic phase was washed with water and brine, dried ($Na_2SO_4$) and concentrated in vacuo. The residue was purified by silica gel chromatography (5-40% EtOAc/hexanes gradient) to give the title compound (0.154 g, 91% yield): $^1$H NMR (400 MHz, $CDCl_3$) δ 7.66 (d, J=8.8 Hz, 1H), 7.07 (s, 1H), 6.97 (d, J=8.8 Hz, 1H), 4.11 (q, J=8.5 Hz, 2H), 3.72 (t, J=5.8 Hz, 2H), 3.62 (t, J=5.8 Hz, 2H).

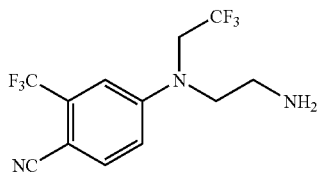

B. 4-[(2-Aminoethyl)(2,2,2-trifluoroethyl)amino]-2-(trifluoromethyl)benzonitrile A mixture of Example 81A (0.150 g, 0.445 mmol) and 10% Pd/C (0.120 g) in MeOH (8 mL) was hydrogenated under balloon pressure for 1 h. The catalyst was filtered off and washed with $CHCl_3$ and MeOH. The filtrate was concentrated in vacuo to give the title compound (0.136 g, 98% crude yield), which was used as such without further purification.

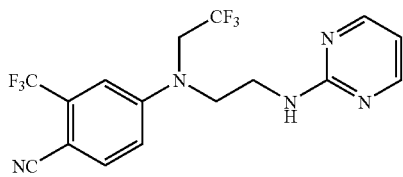

C. 4-[[2-(Pyrimidin-2-ylamino)ethyl](2,2,2-trifluoroethyl)amino]-2-(trifluoromethyl)benzonitrile A mixture of the above intermediate (0.050 g, 0.16 mmol), 2-chloropyrimidine (0.028 g, 0.24 mmol) and DIEA (0.031 g, 0.24 mmol) in THF (3 mL) was heated under $N_2$, in a pressure tube at 180° C. for 6 h. Upon cooling, the mixture was partitioned between EtOAc and 0.1N HCl. The organic phase was washed with 0.1N HCl and brine, dried ($Na_2SO_4$) and concentrated in vacuo. The residue was purified by silica gel chromatography (5-60% EtOAc/hexanes gradient) to give the title compound as a white solid (0.020 g, 32% yield): MS (ES) m/z 390 (M+1).

Example 82

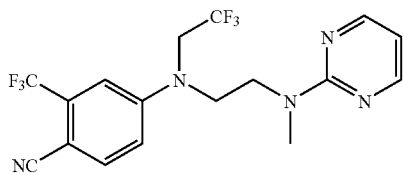

4-[{2-[Methyl(pyrimidin-2-yl)amino]ethyl}(2,2,2-trifluoroethyl)amino]-2-(trifluoromethyl)benzonitrile NaH (60% in oil, 0.003 g, 0.075 mmol) was added to an ice-cold solution of 4-[[2-(pyrimidin-2-ylamino)ethyl](2,2,2-trifluoroethyl)amino]-2-(trifluoromethyl)benzonitrile (0.020 g, 0.051 mmol) in DMF (3 mL), under $N_2$. After stirring for 5 min, iodomethane (0.011 g, 0.078 mmol) was added and stirred for 30 min. The mixture was partitioned between $Et_2O$ and water. The organic phase was washed with water and brine, dried ($Na_2SO_4$) and concentrated in vacuo. The residue was purified by silica gel chromatography (5-50% EtOAc/hexanes gradient) and the product crystallized from $CH_2Cl_2$/hexanes to give the title compound as a white solid (0.014 g, 68% yield): MS (ES) m/z 404 (M+1).

Example 83

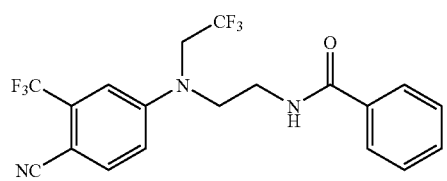

N-{2-[[4-Cyano-3-(trifluoromethyl)phenyl](2,2,2-trifluoroethyl)amino]ethyl}benzamide A solution of crude 4-[(2-aminoethyl)(2,2,2-trifluoroethyl)amino]-2-(trifluoromethyl)benzonitrile (0.018 mg, 0.058 mmol) in $CH_2Cl_2$ (3 mL) was treated with TEA (0.0064 g, 0.063 mmol) and benzoyl chloride (0.0089 mg, 0.063 mmol) and stirred at rt for 1 h. The mixture was partitioned between EtOAc and 0.1N HCl. The organic phase was washed with 0.1N HCl and brine, dried ($Na_2SO_4$) and concentrated in vacuo. The residue was purified by silica gel chromatography (5-70% EtOAc/hexanes gradient) and the product crystallized from $CH_2Cl_2$/hexanes to give the title compound as a white solid (0.016 g, 66% yield): MS (ES) mlz 416 (M+1).

Example 84

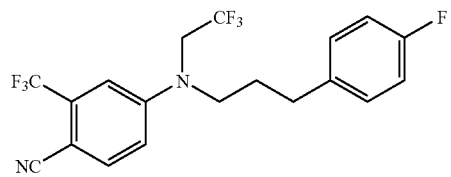

4-[[3-(4-Fluorophenyl)propyl](2,2,2-trifluoroethyl)amino]-2-(trifluoromethyl)benzonitrile

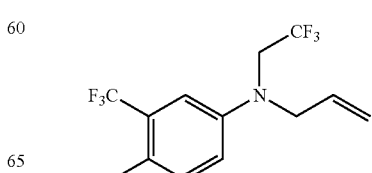

A. 4-[2-Propen-1-yl(2,2,2-trifluoroethyl)amino]-2-(trifluoromethyl)benzonitrile Synthesized according to Example 61A using 4-(2,2,2-trifluoro-ethylamino)-2-trifluoromethyl-benzonitrile and allyl bromide: $^1$H NMR (300 MHz, CDCl$_3$) δ 7.65 (d, J=8.8 Hz, 1H), 7.07 (d, J=2.4 Hz, 1H), 6.93 (dd, J=8.8, 2.6 Hz, 1H), 5.80 (ddt, J=17.2, 10.4, 5.0 Hz, 1H), 5.31 (app. d, J=10.6 Hz, 1H), 5.14 (app. d, J=17.2 Hz, 1H), 4.19-4.11 (m, 2H), 3.98 (q, J=8.6 Hz, 2H); MS (APCI) m/z 309 (M+1).

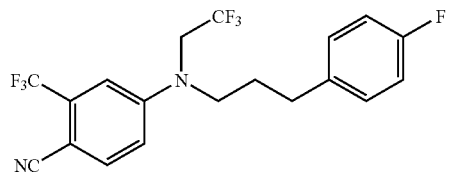

B. 4-[[3-(4-Fluorophenyl)propyl](2,2,2-trifluoroethyl)amino]-2-(trifluoromethyl)benzonitrile A mixture of Example 84A, and 9-BBN dimer (0.147 g, 0.600 mmol) in toluene (1.3 mL) was heated to 60° C. under N$_2$. In the meantime, a second flask was charged with 4-fluorobromobenzene (0.06 mL, 0.55 mmol), an aqueous solution of K$_3$PO4 (0.42 mL, 3.0 M solution, 1.25 mmol), and Pd(PPh$_3$)$_4$ (0.029 g, 0.025 mmol) and the mixture was sparged with N$_2$ for 5 min. After 45 min of heating, the toluene solution of the B-alkyl-9-BBN derivative prepared above was transferred to the second flask via syringe, and the mixture was heated to 80° C. under N$_2$, with vigorous stirring. After 90 min, the mixture was cooled and the layers separated. The aqueous layer was extracted with EtOAc (×3). The combined organic portions were washed (water, brine), dried over Na$_2$SO$_4$, filtered and concentrated in vacuo. The residue was dissolved in Et$_2$O (5 mL) and stirred with 1 N NaOH (5 mL) and 30% w/v H$_2$O$_2$ for 90 min at rt. The layers were separated, the organic layer was washed (water, brine), dried over Na$_2$SO$_4$, filtered and concentrated in vacuo. The residue was purified by flash chromatography (EtOAc/hexanes), affording 0.115 g of the title compound as a colorless film: $^1$H NMR (300 MHz, CD$_3$OD) δ 7.69 (d, J=9.3 Hz, 1H), 7.27-7.17 (m, 2H), 7.09-6.64 (m, 4H), 4.24 (q, J=9.0 Hz, 2H), 3.54 (t, J=7.9 Hz, 2H), 2.67 (t, J=7.5 Hz, 2H), 1.92 (app. pent, J=7.6 Hz, 2H); MS (EI) m/z 404 (M+, 7%), 282 (100%).

Example 85

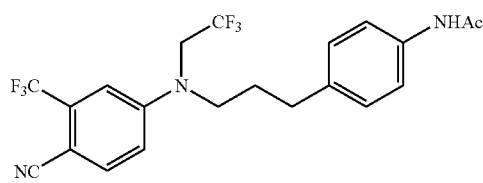

N-(4-{3-[[4-Cyano-3-(trifluoromethyl)phenyl](2,2,2-trifluoroethyl)amino]propyl}phenyl)acetamide Synthesized according to Example 84B from 4-[2-propen-1-yl(2,2,2-trifluoroethyl)amino]-2-(trifluoromethyl)benzonitrile and 4-bromoacetanilide: MS (APCI) m/z 444 (M+1).

Example 86

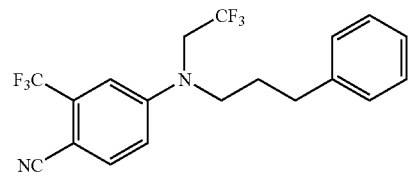

4-[(3-Phenylpropyl)(2,2,2-trifluoroethyl)amino]-2-(trifluoromethyl)benzonitrile

Synthesized according to Example 84B from 4-[2-propen-1-yl(2,2,2-trifluoroethyl)amino]-2-(trifluoromethyl)benzonitrile and bromobenzene: MS (EI) m/z 386 (M+, 6%), 281 (84%), 197 (100%), 170 (76%).

Example 87

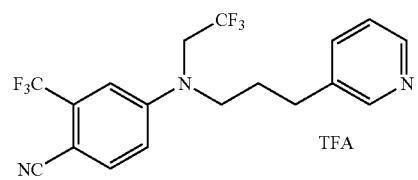

4-[[3-(3-Pyridinyl)propyl](2,2,2-trifluoroethyl)amino]-2-(trifluoromethyl)benzonitrile trifluoroacetate Synthesized according to Example 84B from 4-[2-propen-1-yl(2,2,2-trifluoroethyl)amino]-2-(trifluoromethyl)benzonitrile and 3-bromopyridine. Purified by preparative RP-HPLC (C18 column, MeCN/water containing 0.1% TFA): MS (APCI) m/z 388 (M+1).

Example 88

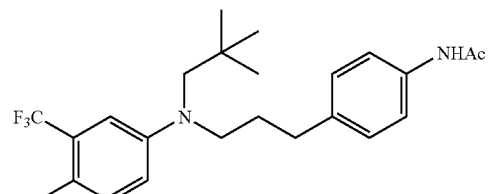

N-(4-{3-[[4-Cyano-3-(trifluoromethyl)phenyl](2,2-dimethylpropyl)amino]propyl}phenyl)acetamide Synthesized according to Example 84B from 4-[(2,2-dimethylpropyl)(2-propen-1-yl)amino]-2-(trifluoromethyl)benzonitrile (Example 49A) and 4-bromoacetanilide: MS (APCI) m/z 432 (M+1).

Example 89

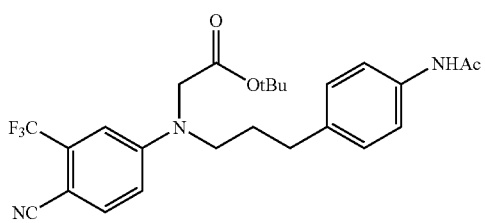

1,1-Dimethylethyl N-{3-[4-(acetylamino)phenyl]propyl}-N-[4-cyano-3-(trifluoromethyl)phenyl]glycinate

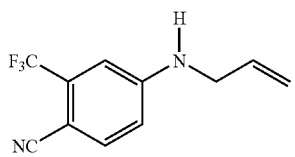

A. 4-(2-Propen-1-ylamino)-2-(trifluoromethyl)benzonitrile

Synthesized as described in Example 1A from 4-fluoro-2-(trifluoromethyl)benzonitrile and allylamine: MS (APCI) m/z 249 ([M+Na]$^+$).

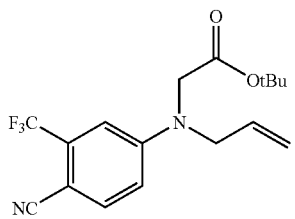

B. 1,1-Dimethylethyl N-[4-cyano-3-(trifluoromethyl)phenyl]-N-2-propen-1-ylglycinate Synthesized as described in Example 70B, excluding TFA deprotection of the tert-butyl ester. Purified by flash chromatography (EtOAc/hexanes), obtained as a pale yellow gum: MS (APCI) m/z 341 (M+1).

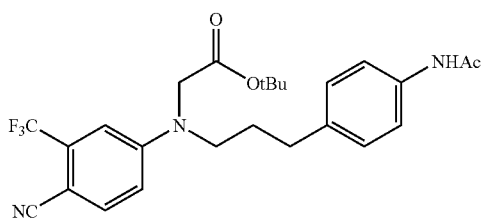

C. 1,1-Dimethylethyl N-{3-[4-(acetylamino)phenyl]propyl}-N-[4-cyano-3-(trifluoromethyl)phenyl]glycinate Synthesized according to Example 84B from 1,1-dimethylethyl N-[4-cyano-3-(trifluoromethyl)phenyl]-N-2-propen-1-ylglycinate and 4-bromoacetanilide: MS (APCI) m/z 498 ([M+Na]$^+$), 420 ({[M+H]—C$_4$H$_8$}$^+$).

Example 90

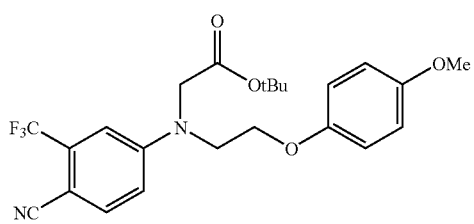

1,1-Dimethylethyl N-[4-cyano-3-(trifluoromethyl)phenyl]-N-(2-{[4-(methyloxy)phenyl]oxy}ethyl)glycinate

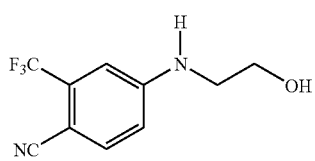

A. 4-[(2-Hydroxyethyl)amino]-2-(trifluoromethyl)benzonitrile

Synthesized as described in Example 1A from 4-fluoro-2-(trifluoromethyl)benzonitrile and aminoethanol (3 equivalents): MS (APCI) m/z 231 (M+1).

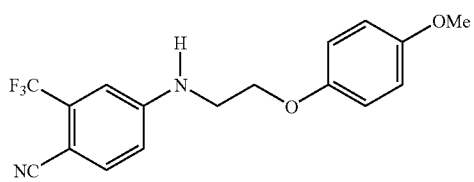

B. 4-[(2-{[4-(Methyloxy)phenyl]oxy}ethyl)amino]-2-(trifluoromethyl)benzonitrile Prepared as described in Example 1C from 4-[(2-hydroxyethyl)amino]-2-(trifluoromethyl)benzonitrile and 4-methoxyphenol: $^1$H NMR (300 MHz, CDCl$_3$) δ 7.58 (d, J=8.6 Hz, 1H), 6.93 (d, J=1.6 Hz, 1H), 6.85 (s, 4H), 6.76 (dd, J=8.7, 1.7 Hz, 1H), 5.66 (bs, 1H), 4.15 (t, J=4.7, 2H), 3.78 (s, 3H), 3.59 (t, J=4.9 Hz, 2H).

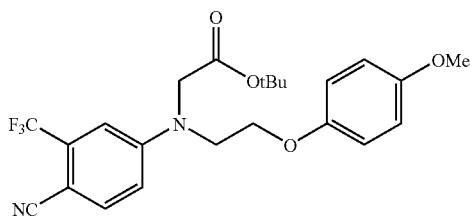

C. 1,1-Dimethylethyl N-[4-cyano-3-(trifluoromethyl)phenyl]-N-(2-{[4-(methyloxy)phenyl]oxy}ethyl) glycinate Synthesized as described in Example 70B from 4-[(2-{[4-(methyloxy)phenyl]oxy}ethyl)amino]-2-(trifluoromethyl) benzonitrile, excluding TFA deprotection of tert-butyl ester. Purified by flash chromatography (EtOAc/hexanes), obtained as a colorless gum: MS (APCI) m/z 451 (M+1).

Example 91

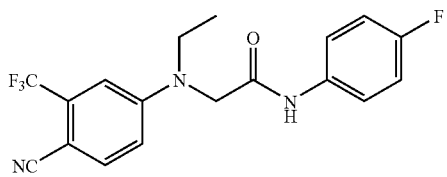

N²-[4-Cyano-3-(trifluoromethyl)phenyl]-N²-ethyl-N¹-(4-fluorophenyl)glycinamide

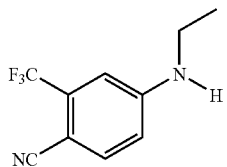

A. 4-(Ethylamino)-2-(trifluoromethyl)benzonitrile

Synthesized as described in Example 1A using ethylamine: ¹H NMR (400 MHz, CDCl₃) δ 7.53 (d, J=8.4 Hz, 1H), 6.82 (d, J=2.2 Hz, 1H), 6.65 (dd, J=8.6, 2.4 Hz, 1H), 4.42 (bs, 1H), 3.23 (q, J=7.2 Hz, 2H), 1.29 (t, J=7.2 Hz, 3H).

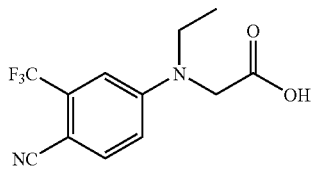

B. N-[4-Cyano-3-(trifluoromethyl)phenyl]-N-ethylglycine

Synthesized as described in Example 70B using 4-(ethylamino)-2-(trifluoromethyl)benzonitrile and 1,1-dimethylethyl bromoacetate: ¹H NMR (400 MHz, CDCl₃) δ 7.60 (d, J=8.7 Hz, 1H), 6.89 (d, J=2.6 Hz, 1H), 6.72 (dd, J=8.7, 2.7 Hz, 1H), 4.16 (s, 2H), 3.53 (q, J=7.1 Hz, 2H), 1.24 (t, J=7.0 Hz, 3H).

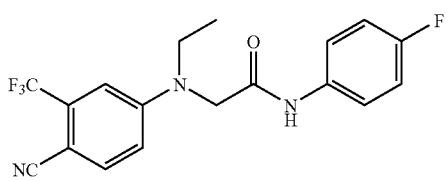

C. N²-[4-Cyano-3-(trifluoromethyl)phenyl]-N²-ethyl-N¹-(4-fluorophenyl)glycinamide A mixture of N-[4-cyano-3-(trifluoromethyl)phenyl]-N-ethyl glycine, Example 91B (0.074 g, 0.25 mmol), and resin bounded carbodiimide (0.50 g, 1.26 mmol/g) was shaken in CH₂Cl₂ (15 mL) for 30 min, then 4-fluoroaniline (0.044 g, 0.4 mmol) was added, and the mixture was shaken for another 12 h. The resin was filtered and washed with CH₂Cl₂ (2×10 mL). The resulting filtrate was concentrated under vacuum. The residue was triturated with Et₂O to obtain 0.018 g (11%) of the title compound as a white solid: ¹H NMR (400 MHz, CDCl₃) δ 7.42-7.39 (m, 2H), 7.06-6.99 (m, 4H), 6.85 (dd, J=9.0, 2.7 Hz, 1H), 4.10 (s, 2H), 3.64 (q, J=7.1 Hz, 2H), 1.31 (t, J=7.1 Hz, 3H); MS (APCI) m/z 366 (M+1).

Example 92

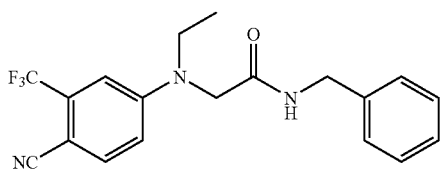

N²-[4-Cyano-3-(trifluoromethyl)phenyl]-N²-ethyl-N¹-(phenylmethyl)glycinamide

Synthesized as described for Example 91C using benzyl amine: MS (APCI) m/z 362 (M+1).

Example 93

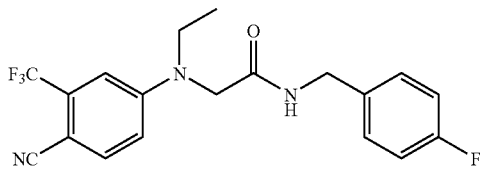

N²-[4-Cyano-3-(trifluoromethyl)phenyl]-N²-ethyl-N¹-[(4-fluorophenyl)methyl]glycinamide Synthesized as described for Example 91C using 4-fluorobenzyl amine: MS (APCI) m/z 380 (M+1).

Example 94

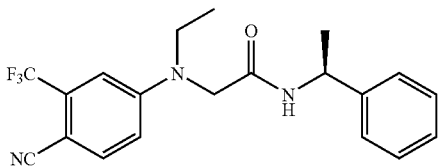

N²-[4-Cyano-3-(trifluoromethyl)phenyl]-N²-ethyl-N¹-[(1S)-1-phenylethyl]glycinamide Synthesized as described for Example 91C using (1S)-1-phenylethanamine: MS (APCI) m/z 376 (M+1).

Example 95

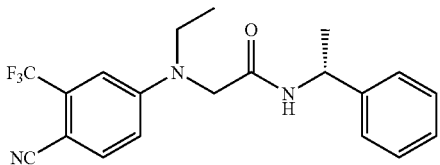

N²-[4-Cyano-3-(trifluoromethyl)phenyl]-N²-ethyl-N¹-[(1R)-1-phenylethyl]glycinamide Synthesized as described for Example 91C using (1R)-1-phenylethanamine: MS (APCI) m/z 376 (M+1).

Example 96

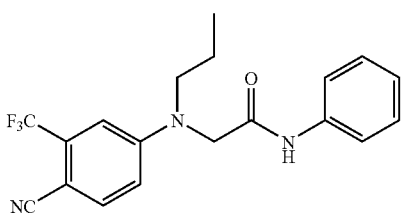

N²-[4-Cyano-3-(trifluoromethyl)phenyl]-N¹-phenyl-N²-propylglycinamide

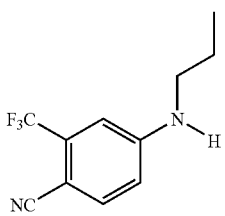

A. 4-(Propylamino)-2-(trifluoromethyl)benzonitrile

Synthesized as described in Example 1A using n-propylamine: ¹H NMR (400 MHz, CDCl₃) δ 7.53 (d, J=8.6 Hz, 1H), 6.82 (d, J=2.4 Hz, 1H), 6.65 (dd, J=8.6, 2.4 Hz, 1H), 4.44 (bs, 1H), 3.15 (t, J=7.1 Hz, 2H), 1.67 (m, 2H), 1.01 (t, J=7.5 Hz, 3H).

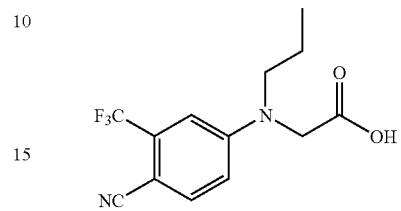

B. N-[4-Cyano-3-(trifluoromethyl)phenyl]-N-propylglycine

Synthesized as described in Example 70B using 4-(propylamino)-2-(trifluoromethyl)benzonitrile and 1,1-dimethylethyl bromoacetate: ¹H NMR (400 MHz, CDCl₃) δ 7.61 (d, J=8.7 Hz, 1H), 6.87 (d, J=2.6 Hz, 1H), 6.71 (dd, J=8.8, 2.6 Hz, 1H), 4.18 (s, 2H), 3.41 (t, J=7.7 Hz, 2H), 1.68 (m, 2H), 0.98 (t, J=7.5 Hz, 3H).

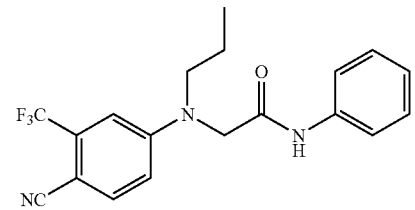

C. N²-[4-Cyano-3-(trifluoromethyl)phenyl]-N¹-phenyl-N²-propylglycinamide

Synthesized as described in Example 91C using N-[4-cyano-3-(trifluoromethyl)phenyl]-N-propylglycine and aniline: MS (APCI) m/z 360 ([M]⁻).

Example 97

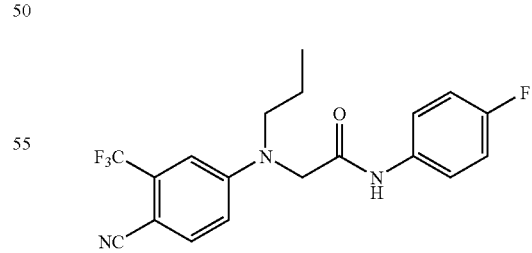

N²-[4-Cyano-3-(trifluoromethyl)phenyl]-N¹-(4-fluorophenyl)-N²-propylglycinamide

Synthesized as described for Example 91C using N-[4-cyano-3-(trifluoromethyl)phenyl]-N-propylglycine and 4-fluoroaniline: MS (APCI) m/z 380 (M+1).

Example 98

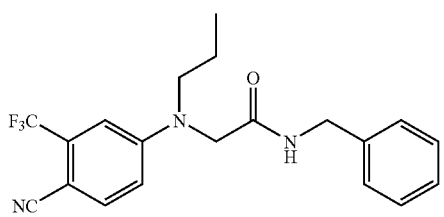

N²-[4-Cyano-3-(trifluoromethyl)phenyl]-N¹-(phenylmethyl)-N²-propylglycinamide

Synthesized as described for Example 91C using N-[4-cyano-3-(trifluoromethyl)phenyl]-N-propylglycine and benzyl amine: MS (APCI) m/z 376 (M+1).

Example 99

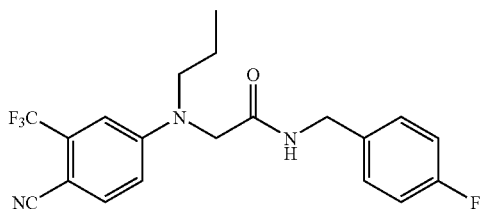

N²-[4-Cyano-3-(trifluoromethyl)phenyl]-N¹-[(4-fluorophenyl)methyl]-N²-propylglycinamide Synthesized as described in Example 91C using N-[4-cyano-3-(trifluoromethyl)phenyl]-N-propylglycine and 4-fluorobenzyl amine: MS (APCI) m/z 394 (M+1).

Example 100

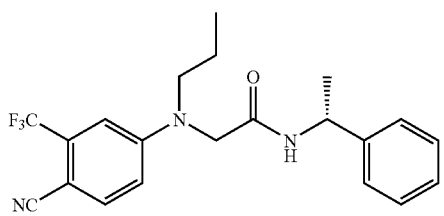

N²-[4-Cyano-3-(trifluoromethyl)phenyl]-N¹-[(1R)-1-phenylethyl]-N²-propylglycinamide Synthesized as described in Example 91C using N-[4-cyano-3-(trifluoromethyl)phenyl]-N-propylglycine and (1R)-1-phenylethanamine: MS (APCI) m/z 390 (M+1).

Example 101

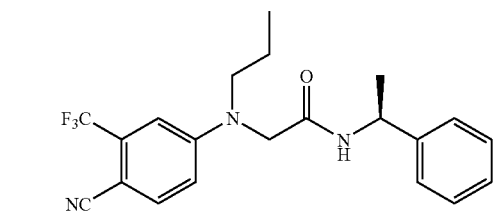

N²-[4-Cyano-3-(trifluoromethyl)phenyl]-N¹-[(1S)-1-phenylethyl]-N²-propylglycinamide Synthesized as described for Example 91C using N-[4-cyano-3-(trifluoromethyl)phenyl]-N-propylglycine and (1S)-1-phenylethanamine: MS (APCI) m/z 390 (M+1).

Example 102

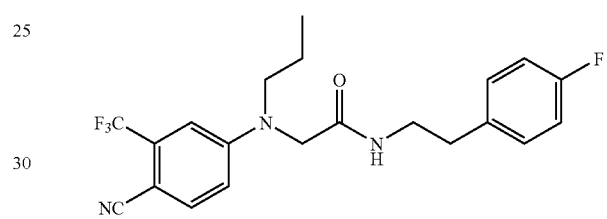

N²-[4-Cyano-3-(trifluoromethyl)phenyl]-N¹-[2-(4-fluorophenyl)ethyl]-N²-propylglycinamide Synthesized as described for Example 91C using N-[4-cyano-3-(trifluoromethyl)phenyl]-N-propylglycine and 2-[(4-fluorophenyl)ethyl]amine: MS (APCI) m/z 408 (M+1).

Example 103

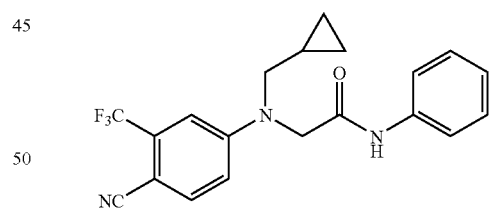

N²-[4-Cyano-3-(trifluoromethyl)phenyl]-N²-(cyclopropylmethyl)-N¹-phenylglycinamide

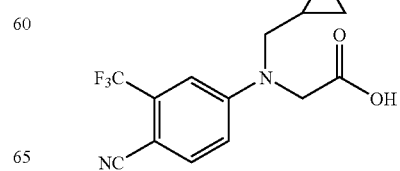

A. N-[4-Cyano-3-(trifluoromethyl)phenyl]-N-(cyclopropylmethyl)glycine

Synthesized in a manner similar to Example 70B using example 1A and 1,1-dimethylethyl bromoacetate: $^1$H NMR (400 MHz, CDCl$_3$) δ 7.61 (d, J=8.8 Hz, 1H), 6.97 (d, J=2.8 Hz, 1H), 6.78 (dd, J=8.8, 2.8 Hz, 1H), 4.29 (s, 2H), 3.34 (d, J=6.4 Hz, 2H), 1.37 (m, 1H), 0.64 (m, 2H), 0.27 (m, 2H).

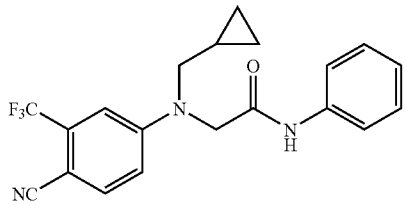

B. N$^2$-[4-Cyano-3-(trifluoromethyl)phenyl]-N$^2$-(cyclopropylmethyl)-N$^1$-phenylglycinamide Synthesized as described for Example 91C using N-[4-cyano-3-(trifluoromethyl)phenyl]-N-(cyclopropylmethyl)glycine and aniline: MS (APCI) m/z 374 (M+1).

Example 104

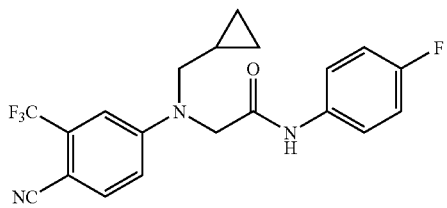

N$^2$-[4-Cyano-3-(trifluoromethyl)phenyl]-N$^2$-(cyclopropylmethyl)-N$^1$-(4-fluorophenyl)glycinamide Synthesized as described for Example 91C using N-[4-cyano-3-(trifluoromethyl)phenyl]-N-(cyclopropylmethyl)glycine and 4-fluoroaniline: MS (APCI) m/z 392 (M+1).

Example 105

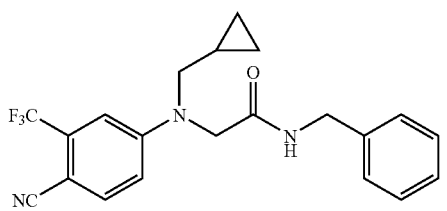

N$^2$-[4-Cyano-3-(trifluoromethyl)phenyl]-N$^2$-(cyclopropylmethyl)-N$^1$-(phenylmethyl)glycinamide Synthesized as described for Example 91C using N-[4-cyano-3-(trifluoromethyl)phenyl]-N-(cyclopropylmethyl)glycine and benzyl amine: MS (APCI) m/z 388 (M+1).

Example 106

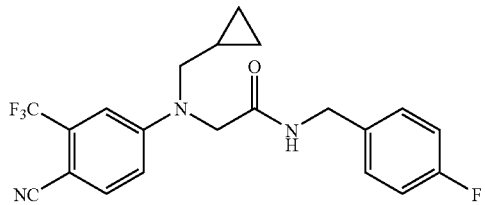

N$^2$-[4-Cyano-3-(trifluoromethyl)phenyl]-N$^2$-(cyclopropylmethyl)-N$^1$-[(4-fluorophenyl)methyl]glycinamide Synthesized as described for Example 91C using N-[4-cyano-3-(trifluoromethyl)phenyl]-N-(cyclopropylmethyl)glycine and 4-fluorobenzyl amine: MS (APCI) m/z 406 (M+1).

Example 107

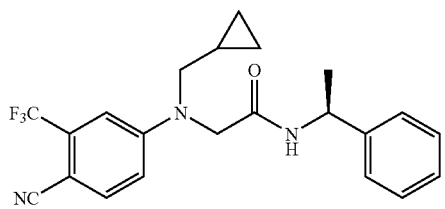

N$^2$-[4-Cyano-3-(trifluoromethyl)phenyl]-N$^2$-(cyclopropylmethyl)-N$^1$-[(1S)-1-phenylethyl]glycinamide Synthesized as described for Example 91C using N-[4-cyano-3-(trifluoromethyl)phenyl]-N-(cyclopropylmethyl)glycine and (1S)-1-phenylethanamine: MS (APCI) m/z 402 (M+1).

Example 108

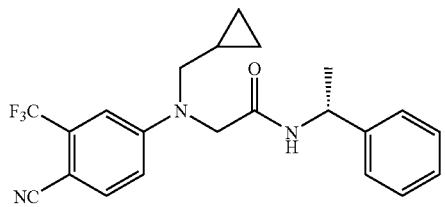

N$^2$-[4-Cyano-3-(trifluoromethyl)phenyl]-N$^2$-(cyclopropylmethyl)-N$^1$-[(1R)-1-phenylethyl]glycinamide Synthesized as described for Example 91C using N-[4-cyano-3-(trifluoromethyl)phenyl]-N-(cyclopropylmethyl)glycine and (1R)-1-phenylethanamine: MS (APCI) m/z 402 (M+1).

Example 109

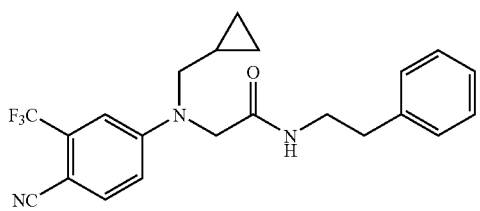

N²-[4-Cyano-3-(trifluoromethyl)phenyl]-N²-(cyclopropylmethyl)-N¹-(2-phenylethyl)glycinamide Synthesized as described for Example 91C using N-[4-cyano-3-(trifluoromethyl)phenyl]-N-(cyclopropylmethyl)glycine and 2-(phenethyl)amine: MS (APCI) m/z 402 (M+1).

Example 110

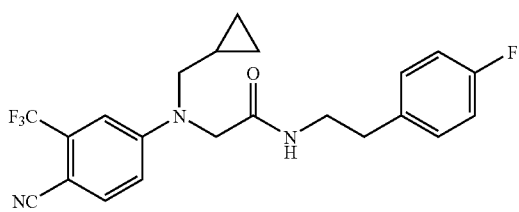

N²-[4-Cyano-3-(trifluoromethyl)phenyl]-N²-(cyclopropylmethyl)-N¹-[2-(4-fluorophenyl)ethyl]glycinamide Synthesized as described for Example 91C using N-[4-cyano-3-(trifluoromethyl)phenyl]-N-(cyclopropylmethyl)glycine and 2-[(4-fluorophenyl)ethyl]amine: MS (APCI) m/z 420 (M+1).

Example 111

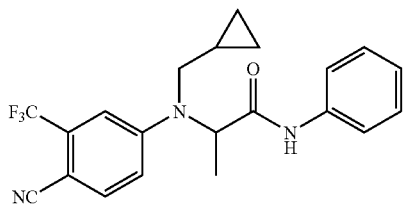

N²-[4-Cyano-3-(trifluoromethyl)phenyl]-N²-(cyclopropylmethyl)-N¹-phenylalaninamide

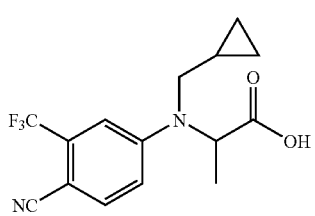

A. N-[4-Cyano-3-(trifluoromethyl)phenyl]-N-(cyclopropylmethyl)alanine

Synthesized as described in Example 70B using Example 1A and 1,1-dimethylethyl 2-bromopropanoate: ¹H NMR (400 MHz, CDCl₃) δ 7.61 (d, J=8.9 Hz, 1H), 7.09 (d, J=2.6 Hz, 1H), 6.88 (dd, J=8.8, 2.6 Hz, 1H), 4.56 (q, J=7.1 Hz, 1H), 3.30 (d, J=5.8 Hz, 2H), 1.62 (d, J=7.1 Hz, 3H), 1.00 (m, 1H), 0.65 (m, 2H), 0.29 (m, 2H).

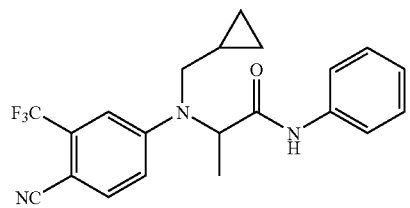

B. N²-[4-Cyano-3-(trifluoromethyl)phenyl]-N²-(cyclopropylmethyl)-N¹-phenylalaninamide Synthesized as described for Example 91C using N-[4-cyano-3-(trifluoromethyl)phenyl]-N-(cyclopropylmethyl)alanine and aniline: ¹H NMR (400 MHz, CDCl₃) δ 8.20 (s, 1H), 7.51 (d, J=8.9 Hz, 1H), 7.45 (d, J=7.9 Hz, 2H), 7.30 (t, J=7.7 Hz, 2H), 7.16 (d, J=2.4 Hz, 1H), 7.11 (t, J=7.5 Hz, 1H), 6.93 (dd, J=8.9, 2.7 Hz, 1H), 4.47 (q, J=7.0 Hz, 1H), 3.37 (m, 2H), 1.56 (d, J=6.9 Hz, 3H), 1.12 (m, 1H), 0.69 (m, 2H), 0.37 (m, 2H).

Example 112

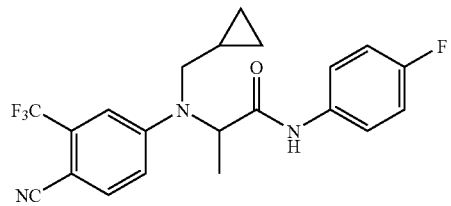

N²-[4-Cyano-3-(trifluoromethyl)phenyl]-N²-(cyclopropylmethyl)-N¹-(4-fluorophenyl)alaninamide Synthesized as described for Example 91C using N-[4-cyano-3-(trifluoromethyl)phenyl]-N-(cyclopropylmethyl)alanine and 4-fluoroaniline: ¹H NMR (400 MHz, CDCl₃) δ 8.21 (s, 1H), 7.50 (d, J=8.7 Hz, 1H), 7.42 (m, 2H), 7.14 (d, J=2.5 Hz, 1H), 7.00-6.91 (m, 3H), 4.47 (q, J=7.0 Hz, 1H), 3.36 (m, 2H), 1.56 (d, J=7.1 Hz, 3H), 1.10 (m, 1H), 0.69 (m, 2H), 0.35 (m, 2H).

Example 113

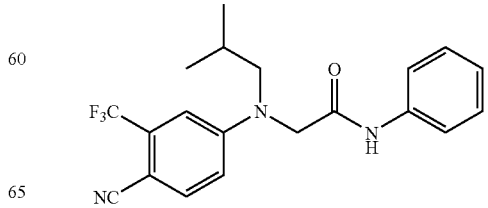

N²-[4-Cyano-3-(trifluoromethyl)phenyl]-N²-(2-methylpropyl)-N¹-phenylglycinamide

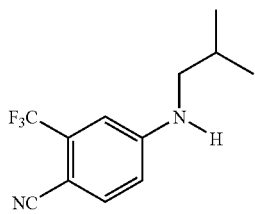

A. 4-(Isobutylamino)-2-(trifluoromethyl)benzonitrile

Synthesized as described in Example 1A using isobutylamine: ¹H NMR (400 MHz, CDCl₃) δ 7.53 (d, J=8.6 Hz, 1H), 6.82 (d, J=2.4 Hz, 1H), 6.65 (dd, J=8.6, 2.5 Hz, 1H), 4.45 (bs, 1H), 3.00 (d, J=7.0 Hz, 2H), 1.90 (m, 1H), 1.00 (d, J=6.8 Hz, 6H).

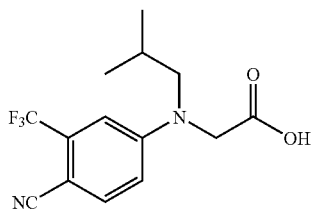

B. N-[4-Cyano-3-(trifluoromethyl)phenyl]-N-isobutylglycine

Synthesized as described in Example 70B using 4-(isobutylamino)-2-(trifluoromethyl)benzonitrile and 1,1-dimethylethyl bromoacetate: ¹H NMR (400 MHz, CDCl₃) δ 7.59 (d, J=9.0 Hz, 1H), 6.90 (d, J=2.6 Hz, 1H), 6.72 (dd, J=9.0, 2.7 Hz, 1H), 4.19 (s, 2H), 3.26 (d, J=7.5 Hz, 2H), 2.04 (m, 1H), 0.97 (d, J=6.6 Hz,

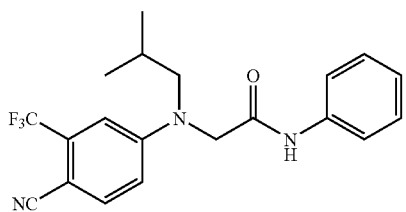

C. N²-[4-Cyano-3-(trifluoromethyl)phenyl]-N²-(2-methylpropyl)-N¹-phenylglycinamide Synthesized as described for Example 91C using N-[4-cyano-3-(trifluoromethyl)phenyl]-N-isobutylglycine and aniline: MS (APCI) m/z 376 (M+1).

Example 114

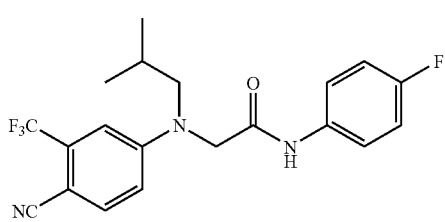

N²-[4-Cyano-3-(trifluoromethyl)phenyl]-N¹-(4-fluorophenyl)-N²-(2-methylpropyl)glycinamide Synthesized as described for Example 91C using N-[4-cyano-3-(trifluoromethyl)phenyl]-N-isobutylglycine and 4-fluoroaniline: MS (APCI) m/z 394 (M+1).

Example 115

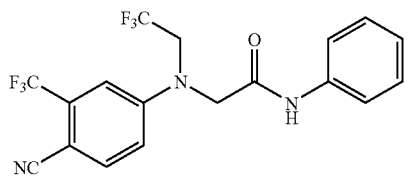

N²-[4-Cyano-3-(trifluoromethyl)phenyl]-N¹-phenyl-N²-(2,2,2-trifluoroethyl)glycinamide

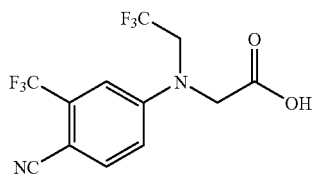

A. N-[4-Cyano-3-(trifluoromethyl)phenyl]-N-(2,2,2-trifluoroethyl)glycine

Synthesized in a manner similar to Example 70B using Example 11A and 1,1-dimethylethyl bromoacetate: ¹H NMR (300 MHz, CD₃OD) δ 7.67 (d, J=8.6 Hz, 1H), 7.07 (d, J=2.8 Hz, 1H), 7.03 (dd, J=8.6, 2.8 Hz, 1H), 4.28 (s, overlapped with 4.24, 2H), 4.24 (q, J=8.8 Hz, 2H).

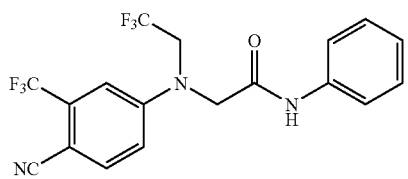

B. N²-[4-Cyano-3-(trifluoromethyl)phenyl]-N¹-phenyl-N²-(2,2,2-trifluoroethyl)glycinamide Synthesized as described for Example 91C using N-[4-cyano-3-(trifluoromethyl)phenyl]-N-(2,2,2-trifluoroethyl)glycine and aniline: MS (APCI) m/z 402 (M+1).

Example 116

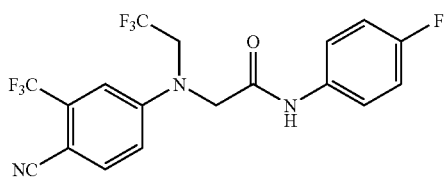

N²-[4-Cyano-3-(trifluoromethyl)phenyl]-N¹-(4-fluorophenyl)-N²-(2,2,2-trifluoroethyl)glycinamide Synthesized as described for Example 91C using N-[4-cyano-3-(trifluoromethyl)phenyl]-N-(2,2,2-trifluoroethyl) glycine and 4-fluoroaniline: MS (APCI) m/z 420 (M+1).

Example 117

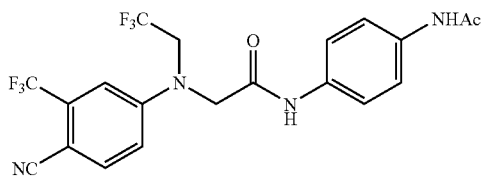

N¹-[4-(Acetylamino)phenyl]-N²-[4-cyano-3-(trifluoromethyl)phenyl]-N²-(2,2,2-trifluoroethyl)glycinamide Synthesized as described for Example 91C using N-[4-cyano-3-(trifluoromethyl)phenyl]-N-(2,2,2-trifluoroethyl) glycine and N-(4-aminophenyl)acetamide: MS (APCI) m/z 459 (M+1).

Example 118

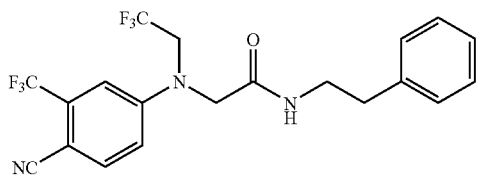

N²-[4-Cyano-3-(trifluoromethyl)phenyl]-N¹-(2-phenylethyl)-N²-(2,2,2-trifluoroethyl)glycinamide Synthesized as described for Example 91C using N-[4-cyano-3-(trifluoromethyl)phenyl]-N-(2,2,2-trifluoroethyl) glycine and (2-phenethyl)amine: MS (APCI) m/z 430 (M+1).

Example 119

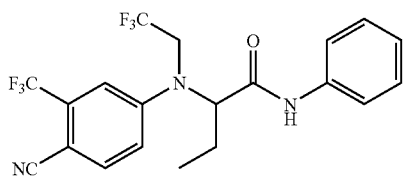

2-[[4-Cyano-3-(trifluoromethyl)phenyl](2,2,2-trifluoroethyl)amino]-N-phenylbutanamide

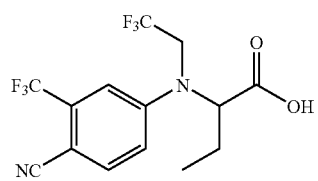

A. 2-[[4-Cyano-3-(trifluoromethyl)phenyl](2,2,2-trifluoroethyl)amino]butanoic acid Synthesized as described in Example 70B using example 11A and tert-butyl 2-bromobutanoate: ¹H NMR (400 MHz, CDCl₃) δ 7.68 (d, J=8.8 Hz, 1H), 7.17 (d, J=2.8 Hz, 1H), 7.02 (dd, J=8.8, 2.8 Hz, 1H), 4.22 (dd, J=8.8, 6.3 Hz, 1H), 4.05 (m, 2H), 2.20 (m, 1H), 1.98 (m, 1H), 1.56 (t, J=7.3 Hz, 3H).

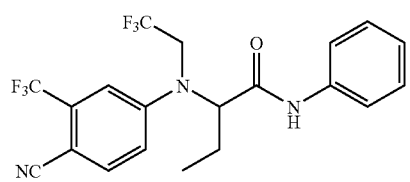

B. 2-[[4-Cyano-3-(trifluoromethyl)phenyl](2,2,2-trifluoroethyl)amino]-N-phenylbutanamide Synthesized as described in Example 91C using 2-[[4-cyano-3-(trifluoromethyl)phenyl](2,2,2-trifluoroethyl) amino]butanoic acid and aniline: ¹H NMR (400 MHz, CDCl₃) δ 7.85 (s, 1H), 7.64 (d, J=8.8 Hz, 1H), 7.42 (d, J=7.8 Hz, 2H), 7.31 (t, J=7.7 Hz, 2H), 7.25 (d, J=3.5 Hz, 1H), 7.14 (t, J=7.3 Hz, 1H), 7.08 (dd, J=9.0, 2.7 Hz, 1H), 4.30 (m, 1H), 4.20-4.08 (m, 2H), 2.33 (m, 1H), 1.98 (m, 1H), 1.06 (t, J=7.3 Hz, 3H).

Example 120

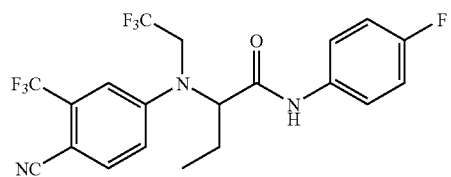

2-[[4-Cyano-3-(trifluoromethyl)phenyl](2,2,2-trifluoroethyl)amino]-N-(4-fluorophenyl)butanamide Synthesized as described in Example 91C using 2-[[4-cyano-3-(trifluoromethyl)phenyl](2,2,2-trifluoroethyl) amino]butanoic acid and 4-fluoroaniline:
¹H NMR (400 MHz, CDCl₃) δ 7.98 (s, 1H), 7.61 (d, J=8.8 Hz, 1H), 7.40 (m, 2H), 7.24 (d, J=1.7 Hz, 1H), 7.09 (dd, J=8.8, 2.6 Hz, 1H), 6.98 (m, 2H), 4.35-4.10 (m, 3H), 2.30 (m, 1H), 1.94 (m, 1H), 1.05 (t, J=7.4 Hz, 3H).

Example 121

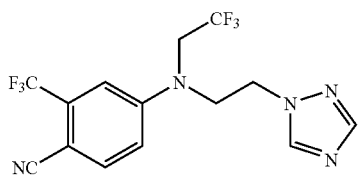

4-[[2-(1H-1,2,4-Triazol-1-yl)ethyl](2,2,2-trifluoroethyl)amino]-2-(trifluoromethyl)benzonitrile A mixture of 2-[[4-cyano-3-(trifluoromethyl)phenyl](2,2,2-trifluoroethyl)amino]ethyl methanesulfonate, Example 15C (0.050 g, 0.128 mmol) and 1,2,4-triazole sodium salt (0.023 g, 0.256 mmol) in DMF (2 mL) was heated at 60° C. under $N_2$ for 45 min. Upon cooling, the mixture was partitioned between $Et_2O$ and water. The organic phase was washed with water and the combined aqueous phases were extracted twice with $Et_2O$. The combined organic phases were washed with brine, dried ($Na_2SO_4$), and concentrated in vacuo. The residue was purified by silica gel chromatography (5-80% EtOAc/hexanes gradient followed by 1-10% MeOH/EtOAc gradient) and the product was crystallized from $CH_2Cl_2$/hexanes to give the title compound as a white solid (0.038 mg, 83% yield): MS (ES) m/z 364 (M+1).

Example 122

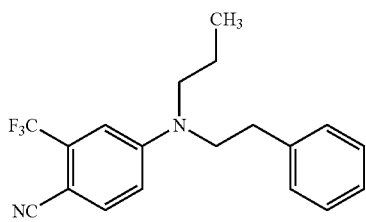

4-[(2-Phenylethyl)(propyl)amino]-2-(trifluoromethyl)benzonitrile

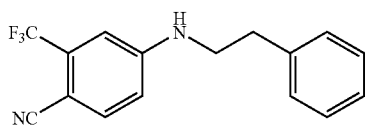

A. 4-[(2-Phenylethyl)amino]-2-(trifluoromethyl)benzonitrile

Synthesized in a manner similar to Example 1A using (2-phenylethyl)amine: MS (ES) m/z 291 (M+1).

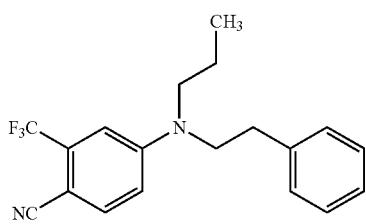

B. 4-[(2-Phenylethyl)(propyl)amino]-2-(trifluoromethyl)benzonitrile

Synthesized in a manner similar to step B of Example 1 using 4-[(2-phenylethyl)amino]-2-(trifluoromethyl)benzonitrile, Example 122A and iodopropane: MS (ES) m/z 333 (M+1).

Example 123

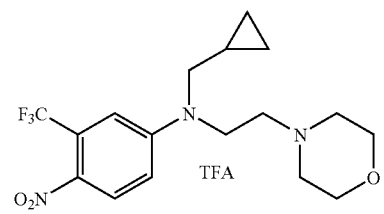

N-(Cyclopropylmethyl)-N-[2-(4-morpholinyl)ethyl]-4-nitro-3-(trifluoromethyl)aniline trifluoroacetate

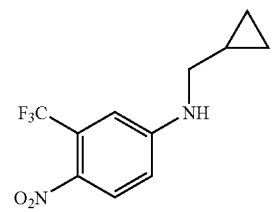

A. N-(Cyclopropylmethyl)-4-nitro-3-(trifluoromethyl)aniline

Synthesized as described in Example 1A from 4-fluoro-1-nitro-2-(trifluoromethyl)benzene and (cyclopropylmethyl)amine: MS (APCI) m/z 261 (M+1).

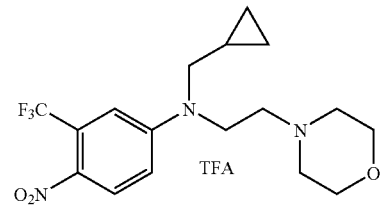

B. N-(Cyclopropylmethyl)-N-[2-(4-morpholinyl)ethyl]-4-nitro-3-(trifluoromethyl)aniline trifluoroacetate A mixture of Example 123A (0.052 g; 0.20 mmol), tetrabutylammonium iodide (0.0075 g, 0.02 mmol), 4-(2-chloroethyl)morpholine (0.039 g, 0.26 mmol), 50% w/v NaOH (0.026 mL, 0.50 mmol) and toluene (0.25 mL) was heated at 100° C. in a sealed vial for 15 h. The mixture was then cooled, diluted with $Et_2O$, poured into water and the layers were separated. The organic layer was concentrated in vacuo, and the residue was purified by preparative RP-HPLC (C18 column, MeCN/water with 0.1% v/v TFA), affording 0.055 g of the title compound as a yellow gum: MS (APCI) m/z 374 (M+1).

Example 124

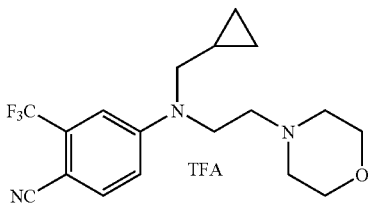

4-{(Cyclopropylmethyl)[2-(4-morpholinyl)ethyl]amino}-2-(trifluoromethyl)benzonitrile trifluoroacetate Synthesized as described in Example 123 from Example 1A and 4-(2-chloroethyl)morpholine: MS (APCI) m/z 354 (M+1).

Example 125

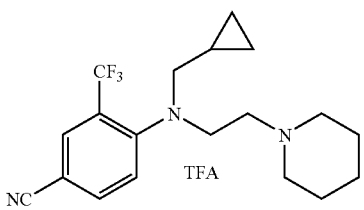

4-{(Cyclopropylmethyl)[2-(1-piperidinyl)ethyl]amino}-3-(trifluoromethyl)benzonitrile trifluoroacetate

A. 4-[(Cyclopropylmethyl)amino]-3-(trifluoromethyl)benzonitrile

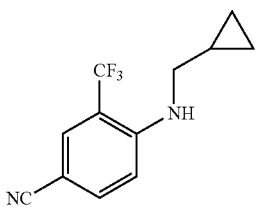

Synthesized as described in Example 1A from 4-fluoro-3-(trifluoromethyl)benzonitrile and (cyclopropylmethyl)amine: MS (APCI) m/z 241 (M+1).

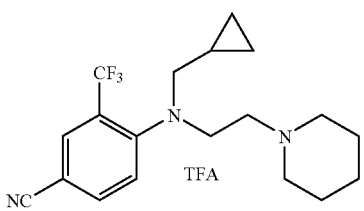

B. 4-{(Cyclopropylmethyl)[2-(1-piperidinyl)ethyl]amino}-3-(trifluoromethyl)benzonitrile trifluoroacetate Synthesized as described in Example 123B from Example 125A and 1-(2-chloroethyl)piperidine: $^1$H NMR (300 MHz, CDCl$_3$) δ 8.09 (d, J=1.5 Hz, 1H), 7.48 (dd, J=8.4, 1.7 Hz, 1H), 7.75 (d, J=8.4 Hz, 1H), 3.61 (t, J=7.4 Hz, 2H), 3.58-3.48 (m, 2H, partially overlapping 3.61), 3.21 (t, J=7.3 Hz, 2H), 2.97 (d, J=6.8 Hz, 2H), 2.97-2.87 (m, 2H, partially overlapping 2.97), 1.98-1.61 (m, 5H), 1.57-1.34 (m, 1H), 1.00-0.85 (m, 1H), 0.47 (overlapping td, 2H), 0.05 (overlapping td, 2H).

Example 126

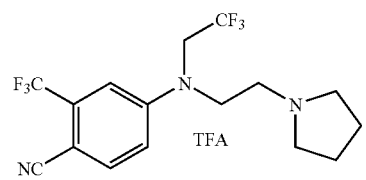

4-[[2-(1-Pyrrolidinyl)ethyl](2,2,2-trifluoroethyl)amino]-2-(trifluoromethyl)benzonitrile trifluoroacetate Synthesized as described in Example 123B from Example 11A and 1-(2-chloroethyl)pyrrolidine: MS (APCI) m/z 366 (M+1).

Biological Section

Compounds of the current invention are modulators of the androgen receptor. Additionally, the compounds of the present invention may also prove useful as modulators of the glucocorticoid receptor, the mineralocorticoid receptor, and/or the progesterone receptor. Activity mediated through oxosteroid nuclear receptors was determined using the following in vitro and in vivo assays.

In Vitro Assays:

The following abbreviations and sources of materials are used
- Fluormone PL Red—a commercially available PR fluoroprobe (PanVera Corp, Product No P2965)
- Fluormone GS Red—a commercially available GR fluoroprobe (PanVera Corp, Product No P2894)
- Fluormone AL Green—a commercially available AR fluoroprobe (PanVera Corp, Product No P3010)
- PR-LBD—Purified human progesterone ligand binding domain tagged with Glutathione Transferase (PanVera Corp, Product No P2900)
- GR—purified human glucocorticoid receptor (PanVera Corp, Product No P2812)
- AR-LBD—Purified rat androgen ligand binding domain tagged with Glutathione Transferase (PanVera Corp, Product No P3009)
- PR Screening Buffer—100 mM potassium phosphate (pH 7.4), 100 μG/ml bovine gamma globulin, 15% ethylene glycol, 0.02% NaN$_3$, 10% glycerol (PanVera Corp Product No P2967) with 0.1% w/v CHAPS
- AR Screening Buffer—pH 7.5 containing protein stabilizing agents and glycerol (PanVera Corp Product No P3011)
- GR Screening Buffer—100 mM potassium phosphate (pH 7.4), 200 mM Na$_2$MoO$_2$, 1 mM EDTA, 20% DMSO (PanVera Corp Product No P2814) with GR stabilizing peptide (100 μM) (PanVera Corp Product No P2815)
- DTT—dithiothreitol (PanVera Corp Product No P2325)
- Discovery Analyst—is an FP reader
- DMSO—dimethylsulphoxide Progesterone Receptor Fluorescence Polarization Assay:

The progesterone receptor fluorescence polarization assay is used to investigate the interaction of the compounds with the progesterone receptor.

Compounds are added to the 384 well black plates to a final volume of 0.5 µL. Sufficient Fluormone PL Red and PR-LBD are defrosted on ice to give a final concentration of 2 nM and 40 nM, respectively. PR screening buffer is chilled to 4° C. prior to addition of DTT to give a final concentration of 1 mM. The Fluormone PL Red and PR-LBD in PR Screening Buffer are added to compound plates to give a final volume of 10 µL. The assay is allowed to incubate at 20-22° C. for 2 hours. The plates are counted in a Discovery Analyst with suitable 535 nM excitation and 590 nM emission interference filters. Compounds that interact with the PR result in a lower fluorescence polarization reading. Test compounds are dissolved and diluted in DMSO. Compounds are assayed in singlicate, a four parameter curve fit of the following form being applied $$y = \frac{a-d}{1+(x/c)^b} + d$$

where a is the minimum, b is the Hill slope, c is the $IC_{50}$ and d is the maximum. Maximum and minimum values are compared to adhesion in the absence of compound and in the presence of $10^{-5}$M progesterone. Data is presented as the mean $pIC_{50}$ with the standard error of the mean of n experiments. Compounds with $pIC_{50}$ greater than 5.0 and a % max greater than 50 are considered desirable.

Androgen Receptor Fluorescence Polarization Assay:

The androgen receptor fluorescence polarization assay is used to investigate the interaction of the compounds with the androgen receptor.

Compounds are added to the 384 well black plates to a final volume of 0.5 µL. Sufficient Fluormone AL Green and AR-LBD are defrosted on ice to give a final concentration of 1 nM and 25 nM, respectively. AR screening buffer is chilled to 4° C. prior to addition of DTT to give a final concentration of 1 mM. The Fluormone AL Green and AR-LBD in AR Screening Buffer are added to compound plates to give a final volume of 10 µL. The assay is allowed to incubate at 20° C. for 5 hours. The plates are counted in a Discovery Analyst with suitable 485 nM excitation and 535 nM emission interference filters. Compounds that interact with the AR result in a lower fluorescence polarization reading. Test compounds are dissolved and diluted in DMSO. Compounds are assayed in singlicate, a four parameter curve fit of the following form being applied $$y = \frac{a-d}{1+(x/c)^b} + d$$

where a is the minimum, b is the Hill slope, c is the $IC_{50}$ and d is the maximum. Maximum and minimum values are compared to adhesion in the absence of compound and in the presence of $10^{-5}$M dihydrotestosterone. Data is presented as the mean $pIC_{50}$ with the standard error of the mean of n experiments. Compounds with $pIC_{50}$ greater than 5.0 and a % max greater than 50 are considered desirable.

Glucocorticoid Receptor Fluorescence Polarization Assay

The glucocorticoid receptor fluorescence polarization assay is used to investigate the interaction of the compounds with the glucocorticoid receptor.

Compounds are added to the 384 well black plates to a final volume of 0.5 µL. Sufficient Fluormone GS Red and GR are defrosted on ice to give a final concentration of 1 nM and 4 nM, respectively. GR screening buffer is chilled to 4° C. prior to addition of DTT to give a final concentration of 1 mM. The Fluormone GS Red, and GR in GR Screening Buffer are added to compound plates to give a final volume of 10 µL. The assay is allowed to incubate at 4° C. for 12 hours. The plates are counted in a Discovery Analyst with suitable 535 nM excitation and 590 nM emission interference filters. Compounds that interact with the GR result in a lower fluorescence polarization reading. Test compounds are dissolved and diluted in DMSO. Compounds are assayed in singlicate, a four parameter curve fit of the following form being applied $$y = \frac{a-d}{1+(x/c)^b} + d$$

where a is the minimum, b is the Hill slope, c is the $EC_{50}$ and d is the maximum. Maximum and minimum values are compared to adhesion in the absence of compound and in the presence of $10^{-5}$M dexamethasone. Data is presented as the mean $pIC_{50}$ with the standard error of the mean of n experiments. Compounds with $pIC_{50}$ greater than 5.0 and a % max greater than 50 are considered desirable.

Transient Transfection Assay:

Cotransfection assays using full-length human AR were performed in CV-1 cells (monkey kidney fibroblasts). The cells were seeded in charcoal-stripped medium in 96-well plates (24,000 cells/well) and incubated overnight. Transient transfections were carried out using the following plasmids: pSG5-AR, MMTV LUC reporter, β-actin SPAP, and pBluescript (filler DNA). The cell plates were then incubated for 6-20 hours. The transfection mixture was washed away and then the cells were drugged with doses ranging from $10^{-10}$ to $10^{-5}$. Two replicates were used for each sample. Incubation with drug was continued for 14 hours. A spectrophotometer was used for SPAP measurements, while a topcounter was used to read the results from the luciferase assay. The ratio of luciferase activity to SPAP activity was calculated to normalize the variance in cell number and transfection efficiency.

Data Analysis:

Data were reduced using RoboFit99. The results were expressed as percent of maximum as calculated by the following formulas:

$$\text{fold activation} = \frac{(((Luc)/(SPAP\text{-}SPAP\text{ substrate blank avg.})) - \text{basal activation})}{\text{basal activation}^*}$$

*basal activation per plate=(Luc vehicle)/(SPAP vehicle–substrate blank average)

% max.=(fold activation of unknown/positive control fold activation avg.)×100

Curves were fit from these data using RoboFit to determine $EC_{50}$'s for agonists and $IC_{50}$'s for antagonists using the following equation:

$Y=((V\text{max}^*x)/(K+x))+Y2$

These values were converted to pEC$_{50}$'s and pIC$_{50}$'s for posting by using the following equations:

$$pEC_{50} = -\log(EC_{50})$$

$$pIC_{50} = -\log(IC_{50})$$

For antagonist assays, the percent maximum response antagonist was calculated by the following formula in which $Y_{min}$ and $Y_{max}$ are curve asymptotes at the maximum or minimum concentration tested:

$$\% \text{ max. resp. ant.} = 100 * (1 - Y_{min}/Y_{max})$$

For antagonist assays, pKb's were calculated using the following formula:

$$pKb = IC_{50} \text{ of unknown}/((1 + *\text{conc}.*)/\text{DHT } EC_{50} \text{ average})$$

where *conc.*=concentration of DHT used as the agonist in the medium for the antagonist experiment, expressed in nM. This concentration was set at twice pEC$_{50}$. This would be 0.2 for AR.

Compounds with a pXC$_{50}$ greater than 5.0 are considered desirable.

Castrated Male Rat Model (ORX Rat)

The activity of the compounds of the present invention as modulators of the androgen receptor was investigated using a castrated male rat model (ORX) as described in C. D. Kockakian, *Pharmac. Therap.* B 1(2), 149-177 (1975); C. Tobin and Y. Joubert, *Developmental Biology* 146, 131-138 (1991); J. Antonio, J. D. Wilson and F. W. George, *J Appl. Physiol.* 87(6) 2016-2019 (1999)) the disclosures of which herein are included by reference.

It has been well defined that androgens play important roles in the maintenance and growth of many tissues in both animals and humans. Muscles, like the levator ani and bulbocavernosus, and sexual accessory organs, such as the prostate glands and seminal vesicles have high expression levels of the androgen receptor and are known to respond quickly to exogenous androgen addition or androgen deprivation through testicular ablation. Castration produces dramatic atrophy of muscle and sexual accessory organs; whereas the administration of exogenous androgens to the castrated animal results in effective hypertrophy of these muscles and sexual accessory organs. Although the levator ani muscle, also known as the dorsal bulbocavernosus, is not 'true skeletal muscle' and definitely sex-linked, it is reasonable to use this muscle to screen muscle anabolic activities of test compounds because of its androgen responsiveness and simplicity of removal.

Male Sprague-Dawley rats weighing 160-180 grams were used in the assay. The rats were singly caged upon receiving and throughout the study. Bilateral orchidectomies were performed in sterilized surgical conditions under isoflurane anesthesia. An anteroposterior incision was made in the scrotum. The testicles were exteriorized and the spermatic artery and vas deferens were ligated with 4.0 silk 0.5 cm proximal to the ligation site. The testicles then were removed by a surgical scissors distal to the ligation sites. The tissue stumps were returned to the scrotum, the scrotum and overlying skin were closed by a surgical stapler. The Sham-ORX rats underwent all procedures except ligation and scissors cutting. The rats were assigned randomly into study groups 7-10 days post surgery based on the body weight.

Dihydrotestosterone (DHT) was used as a positive control (1-10 mg/kg s.c.). Compounds of the current invention were administered subcutaneously or orally for 4-28 days. The rats were weighed daily and doses were adjusted accordingly. The general well being of the animal was monitored throughout the course of the study.

At the end of the study, the rats were euthanized in a CO$_2$ chamber. The ventral prostate glands (VP), seminal vesicles (SV), levator ani muscle (LA) and bulbocavernosus (BC) were carefully dissected. The tissues were blotted dry, the weights were recorded, and then saved for histological and molecular analysis. The VP and SV weights serve as androgenic indicators and LA and BC as anabolic indicators. The ratio of anabolic to androgenic activities was used to evaluate the test compounds. Serum luteinizing hormone (LH), follicle stimulating hormone (FSH) and other potential serum markers of anabolic activities were also analyzed.

In general, desirable compounds show levator ani hypertrophy and very little prostate stimulation.

Test compounds were employed in free or salt form.

All research complied with the principles of laboratory animal care (NIH publication No. 85-23, revised 1985) and GlaxoSmithKline policy on animal use.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included within the scope of the appended claims.

What is claimed is:

1. A compound of formula (I):

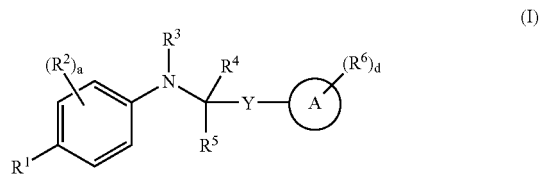

or a salt thereof, wherein
$R^1$ is CN or NO$_2$;
a is 1;
$R^2$ is haloalkyl;
$R^3$ is —(R$^x$)$_f$R$^7$;
f is 1;
$R^x$ is a C$_1$-C$_2$ alkylene chain;
$R^7$ is t-butyl, C$_3$-C$_6$ cycloalkyl, —CF$_3$ or alkoxycarbonyl;
each $R^4$ and $R^5$ independently is H, methyl, ethyl, cyclopropyl, or —CF$_3$;
Y is —(R$^y$)$_g$—, —(R$^y$)$_g$O—, —(R$^y$)$_g$S(O)$_h$—, —(R$^y$)$_g$NR$^9$—, —(R$^y$)$_g$NR$^9$C(O)—, —C(O)NR$^9$—, —C(O)NR$^9$(R$^y$)$_g$—, —(R$^y$))$_g$C(O)—, and —(R$^y$)$_g$CR$^9$=CR$^9$—;
each R$^y$ is —C(R$^{13}$)(R$^{14}$)—;
each g is 1 or 2;
h is 0;
each $R^{13}$ and each $R^{14}$ independently is H, alkyl, cycloalkyl, halogen, haloalkyl, or hydroxyl; or
$R^{13}$ and $R^{14}$ may combine with the carbon atom through which they are substituted to form a 3- to 7-membered ring, which ring may optionally contain one or more heteroatoms selected from O, S, or N;
A is an aryl or heteroaryl;
d is 0, 1, 2, 3, 4, or 5;

each R⁶ independently is C₁-C₆ alkyl, C₃-C₆ cycloalkyl, halogen, C₁-C₆ haloalkyl, hydroxy, C₁-C₆ hydroxyalkyl, C₁-C₆ hydroxyhaloalkyl, cyano, aryl, a 3-10 membered heterocyclyl, heteroaryl, —S(O)ⱼR⁸, —SO₂NR⁹R¹⁰, —O(Rᶻ)ₖR¹¹, —(Rᶻ)ₖC(O)R⁸, —(Rᶻ)ₖC(O)OR¹², —(Rᶻ)ₖC(O)NR⁹R¹⁰, —(Rᶻ)ₖNR⁹C(O)OR¹², —(Rᶻ)ₖNR⁹C(O)R¹², —(Rᶻ)ₖNR⁹SO₂R¹², —NR⁹C(O)NR⁹R¹⁰, or —NR⁹C(NR⁹)NR⁹R¹⁰;

each R⁸ is C₁-C₆ alkyl, C₃-C₆ cycloalkyl, hydroxy, or C₁-C₆ haloalkyl;

each R⁹ and each R¹⁰ independently is H, C₁-C₆ alkyl, C₃-C₆ cycloalkyl, or C₁-C₆ haloalkyl;

each R¹¹ is H, C₁-C₆ alkyl, C₃-C₆ cycloalkyl, C₁-C₆ haloalkyl, a 3-10 membered heterocyclyl, aryl, or heteroaryl;

each R¹² is H, C₁-C₆ alkyl, C₃-C₆ cycloalkyl, or C₁-C₆ haloalkyl;

each Rᶻ is a C₁-C₄ alkylene chain;

each k is 0 or 1; and j is 0, 1, or 2.

2. The compound of claim 1 wherein R¹ is —CN.

3. The compound of claim 1 wherein R² is —CF₃ and is located ortho to R¹.

4. The compound of claim 1 wherein Rˣ is methylene.

5. The compound of claim 1 wherein R⁷ is t-butyl, cyclopropyl, or trifluoromethyl.

6. The compound of claim 1 wherein each of R⁴ and R⁵ are H.

7. The compound of claim 1 wherein Y is —(Rʸ)ɡO—.

8. The compound of claim 7 wherein Rʸ is —CH₂— and g is 1.

9. The compound of claim 1 wherein A is aryl.

10. The compound of claim 9 wherein aryl is phenyl.

11. The compound of claim 1 wherein A is heteroaryl.

12. The compound of claim 11 wherein heteroaryl is indolyl, pyridyl, pyridazinyl, or pyrimidinyl.

13. The compound of claim 1 wherein d is 1 and R⁶ is C₁-C₆ alkyl, halogen, C₁-C₆ haloalkyl, —SO₂R⁸, —SO₂NR⁹R¹⁰, —NR⁹C(O)R¹², or —NR⁹C(O)NR⁹R¹⁰.

14. The compound of claim 13 wherein each R⁸ is C₁-C₆ alkyl and each occurrence of R⁹ and R¹⁰ are H.

15. A compound of claim 1 selected from the group consisting of:

4-[(Cyclopropylmethyl)(2-{[4-(1,1-dimethylethyl)phenyl]oxy}ethyl)amino]-2-(trifluoromethyl)benzonitrile;

N-[4-({2-[[4-Cyano-3-(trifluoromethyl)phenyl](cyclopropylmethyl)amino]ethyl}oxy)phenyl]acetamide;

4-[(Cyclopropylmethyl)(2-{[4-(methyloxy)phenyl]oxy}ethyl)amino]-2-(trifluoromethyl)benzonitrile;

4-((Cyclopropylmethyl){2-[(4-fluorophenyl)oxy]ethyl}amino)-2-(trifluoromethyl)benzonitrile;

4-[(Cyclopropylmethyl)(2-{[4-(hydroxymethyl)phenyl]oxy}ethyl)amino]-2-(trifluoromethyl)benzonitrile;

N-[4-({3-[[4-Cyano-3-(trifluoromethyl)phenyl](cyclopropylmethyl)amino]propyl}oxy)phenyl]acetamide;

4-[(Cyclopropylmethyl)(3-{[4-(1,1-dimethylethyl)phenyl]oxy}propyl)amino]-2-(trifluoromethyl)benzonitrile;

4-[(Cyclopropylmethyl)(3-{[4-(methyloxy)phenyl]oxy}propyl)amino]-2-(trifluoromethyl)benzonitrile;

4-((Cyclopropylmethyl){3-[(4-fluorophenyl)oxy]propyl}amino)-2-(trifluoromethyl)benzonitrile;

4-[(Cyclopropylmethyl)(3-{[4-(hydroxymethyl)phenyl]oxy}propyl)amino]-2-(trifluoromethyl)benzonitrile;

N-[4-({3-[[4-Cyano-3-(trifluoromethyl)phenyl](2,2,2-trifluoroethyl)amino]propyl}oxy)phenyl]acetamide;

4-[(3-{[4-(1,1-Dimethylethyl)phenyl]oxy}propyl)(2,2,2-trifluoroethyl)amino]-2-(trifluoromethyl)benzonitrile;

4-[{3-[(4-Fluorophenyl)oxy]propyl}(2,2,2-trifluoroethyl)amino]-2-(trifluoromethyl)benzonitrile;

4-[(3-{[4-(Methyloxy)phenyl]oxy}propyl)(2,2,2-trifluoroethyl)amino]-2-(trifluoromethyl)benzonitrile;

4-[{2-[(4-{[2-(1-Piperidinyl)ethyl]oxy}phenyl)oxy]ethyl}(2,2,2-trifluoroethyl)amino]-2-(trifluoromethyl)benzonitrile;

4-[(2-{[4-(Methyloxy)phenyl]oxy}ethyl)(2,2,2-trifluoroethyl)amino]-2-(trifluoromethyl)benzonitrile;

N-[4-({2-[[4-Cyano-3-(trifluoromethyl)phenyl](2,2,2-trifluoroethyl)amino]ethyl}oxy)phenyl]acetamide;

4-({2-[[4-Cyano-3-(trifluoromethyl)phenyl](2,2,2-trifluoroethyl)amino]ethyl}oxy)benzenesulfonamide;

4-[{2-[(4-Cyanophenyl)oxy]ethyl}(2,2,2-trifluoroethyl)amino]-2-(trifluoromethyl)benzonitrile;

4-[{2-[(4-Fluorophenyl)oxy]ethyl}(2,2,2-trifluoroethyl)amino]-2-(trifluoromethyl)benzonitrile;

4-[(2-{[4-(Oxobutyl)phenyl]oxy}ethyl)(2,2,2-trifluoroethyl)amino]-2-(trifluoromethyl)benzonitrile;

4-[[2-(1H-Indol-5-yloxy)ethyl](2,2,2-trifluoroethyl)amino]-2-(trifluoromethyl)benzonitrile;

4-[{2-[(3-Fluorophenyl)oxy]ethyl}(2,2,2-trifluoroethyl)amino]-2-(trifluoromethyl)benzonitrile;

4-[{2-[(4-Acetylphenyl)oxy]ethyl}(2,2,2-trifluoroethyl)amino]-2-(trifluoromethyl)benzonitrile;

4-[(2-{[4-(2-Oxopropyl)phenyl]oxy}ethyl)(2,2,2-trifluoroethyl)amino]-2-(trifluoromethyl)benzonitrile;

N-[3-({2-[[4-Cyano-3-(trifluoromethyl)phenyl](2,2,2-trifluoroethyl)amino]ethyl}oxy)phenyl]acetamide;

1,1-Dimethylethyl [4-({2-[[4-cyano-3-(trifluoromethyl)phenyl](2,2,2-trifluoroethyl)amino]ethyl}oxy)phenyl]carbamate;

N-[4-({2-[[4-Cyano-3-(trifluoromethyl)phenyl](2,2,2-trifluoroethyl)amino]ethyl}oxy)phenyl]methanesulfonamide;

N-[4-({2-[[4-Cyano-3-(trifluoromethyl)phenyl](2,2,2-trifluoroethyl)amino]ethyl}oxy)phenyl]urea;

4-[(2-{[4-(Methylsulfonyl)phenyl]oxy}ethyl)(2,2,2-trifluoroethyl)amino]-2-(trifluoromethyl)benzonitrile;

4-[(2,2,2-Trifluoroethyl)(2-{[4-(trifluoromethyl)phenyl]oxy}ethyl)amino]-2-(trifluoromethyl)benzonitrile;

Methyl 4-({2-[[4-cyano-3-(trifluoromethyl)phenyl](2,2,2-trifluoroethyl)amino]ethyl}oxy)benzoate;

4-({2-[[4-Cyano-3-(trifluoromethyl)phenyl](2,2,2-trifluoroethyl)amino]ethyl} oxy)benzoic acid;

4-({2-[[4-Cyano-3-(trifluoromethyl)phenyl](2,2,2-trifluoroethyl)amino]ethyl} oxy)benzamide;

1,1-Dimethylethyl {[4-({2-[[4-cyano-3-(trifluoromethyl)phenyl](2,2,2-trifluoroethyl)amino]ethyl}oxy)phenyl]methyl}carbamate;

N-[4-({2-[[4-Cyano-3-(trifluoromethyl)phenyl](2,2,2-trifluoroethyl)amino]ethyl}oxy)phenyl]guanidine trifluoroacetate;

4-[(2-{[4-(Trifluoroacetyl)phenyl]oxy}ethyl)(2,2,2-trifluoroethyl)amino]-2-(trifluoromethyl)benzonitrile;

4-{(2,2,2-Trifluoroethyl)[2-({4-[2,2,2-trifluoro-1-hydroxy-1-(trifluoromethyl)ethyl]phenyl}oxy)ethyl]amino}-2-(trifluoromethyl)benzonitrile;

4-[(2-{[4-(2-Oxo-1-pyrrolidinyl)phenyl]oxy}ethyl)(2,2,2-trifluoroethyl)amino]-2-(trifluoromethyl)benzonitrile;

4-[(2-{[4-(1,3-Thiazol-2-yl)phenyl]oxy}ethyl)(2,2,2-trifluoroethyl)amino]-2-(trifluoromethyl)benzonitrile;

4-[(2-{[4-(1,3-Oxazol-2-yl)phenyl]oxy}ethyl)(2,2,2-trifluoroethyl)amino]-2-(trifluoromethyl)benzonitrile;

4-[{2-[(2-Oxo-1,2,3,4-tetrahydro-6-quinolinyl)oxy]ethyl}(2,2,2-trifluoroethyl)amino]-2-(trifluoromethyl)benzonitrile;
4-[[2-(2-Pyridinyloxy)ethyl](2,2,2-trifluoroethyl)amino]-2-(trifluoromethyl)benzonitrile;
4-[[2-(3-Pyridinyloxy)ethyl](2,2,2-trifluoroethyl)amino]-2-(trifluoromethyl)benzonitrile;
4-[[2-(4-Pyridinyloxy)ethyl](2,2,2-trifluoroethyl)amino]-2-(trifluoromethyl)benzonitrile;
4-[(2,2,2-Trifluoroethyl)(2-{[5-(trifluoromethyl)-2-pyridinyl]oxy}ethyl)amino]-2-(trifluoromethyl)benzonitrile;
4-[{2-[(5-Methyl-2-pyridinyl)oxy]ethyl}(2,2,2-trifluoroethyl)amino]-2-(trifluoromethyl)benzonitrile;
4-[{2-[(6-Chloro-3-pyridinyl)oxy]ethyl}(2,2,2-trifluoroethyl)amino]-2-(trifluoromethyl)benzonitrile;
4-[{2-[(6-Methyl-3-pyridinyl)oxy]ethyl}(2,2,2-trifluoroethyl)amino]-2-(trifluoromethyl)benzonitrile;
4-[{2-[(5-Bromo-2-pyridinyl)oxy]ethyl}(2,2,2-trifluoroethyl)amino]-2-(trifluoromethyl)benzonitrile;
4-[{2-[(6-Fluoro-3-pyridinyl)oxy]ethyl}(2,2,2-trifluoroethyl)amino]-2-(trifluoromethyl)benzonitrile;
4-[{2-[(5-Fluoro-2-pyridinyl)oxy]ethyl}(2,2,2-trifluoroethyl)amino]-2-(trifluoromethyl)benzonitrile;
N-[6-({2-[[4-Cyano-3-(trifluoromethyl)phenyl](2,2,2-trifluoroethyl)amino]ethyl}oxy)-3-pyridinyl]acetamide;
4-[{2-[(6-Oxo-1,6-dihydro-3-pyridinyl)oxy]ethyl}(2,2,2-trifluoroethyl)amino]-2-(trifluoromethyl)benzonitrile;
4-[[2-(3-Pyridazinyloxy)ethyl](2,2,2-trifluoroethyl)amino]-2-(trifluoromethyl)benzonitrile;
4-[[2-(4-Pyrimidinyloxy)ethyl](2,2,2-trifluoroethyl)amino]-2-(trifluoromethyl)benzonitrile;
N-[4-({3-[[4-Cyano-3-(trifluoromethyl)phenyl](2,2-dimethylpropyl)amino]propyl}oxy)phenyl]acetamide;
4-[(3-{[4-(1,1-Dimethylethyl)phenyl]oxy}propyl)(2,2-dimethylpropyl)amino]-2-(trifluoromethyl)benzonitrile;
4-((2,2-Dimethylpropyl){3-[(4-fluorophenyl)oxy]propyl}amino)-2-(trifluoromethyl)benzonitrile;
4-[(2,2-Dimethylpropyl)(3-{[4-(methyloxy)phenyl]oxy}propyl)amino]-2-(trifluoromethyl)benzonitrile;
N-[4-({2-[[4-Cyano-3-(trifluoromethyl)phenyl](2,2-dimethylpropyl)amino]ethyl}oxy)phenyl]acetamide;
4-({2-[[4-Cyano-3-(trifluoromethyl)phenyl](2,2-dimethylpropyl)amino]ethyl}oxy)benzenesulfonamide;
4-((2,2-Dimethylpropyl){2-[(4-fluorophenyl)oxy]ethyl}amino)-2-(trifluoromethyl)benzonitrile;
4-[{2-[(4-Acetylphenyl)oxy]ethyl}(2,2-dimethylpropyl)amino]-2-(trifluoromethyl)benzonitrile;
4-{(2,2-Dimethylpropyl)[2-(phenyloxy)ethyl]amino}-2-(trifluoromethyl)benzonitrile;
4-[(2,2-Dimethylpropyl)(2-{[4-(methylsulfonyl)phenyl]oxy}ethyl)amino]-2-(trifluoromethyl)benzonitrile;
4-((2,2-Dimethylpropyl){2-[(5-fluoro-2-pyridinyl)oxy]ethyl}amino)-2-(trifluoromethyl)benzonitrile;
4-((2,2-Dimethylpropyl){2-[(6-fluoro-3-pyridinyl)oxy]ethyl}amino)-2-(trifluoromethyl)benzonitrile;
4-[(2,2-Dimethylpropyl)(2-{[5-(trifluoromethyl)-2-pyridinyl]oxy}ethyl)amino]-2-(trifluoromethyl)benzonitrile;
N-[4-({2-[[4-Cyano-2-(trifluoromethyl)phenyl](2,2,2-trifluoroethyl)amino]ethyl} oxy)phenyl]acetamide;
4-[{2-[(4-Fluorophenyl)oxy]ethyl}(2,2,2-trifluoroethyl)amino]-3-(trifluoromethyl)benzonitrile;
4-[{2-[(4-Acetylphenyl)oxy]ethyl}(2,2,2-trifluoroethyl)amino]-3-(trifluoromethyl)benzonitrile;
4-[[2-(Phenylthio)ethyl](2,2,2-trifluoroethyl)amino]-2-(trifluoromethyl)benzonitrile;
N-[4-({2-[[4-Cyano-3-(trifluoromethyl)phenyl](2,2,2-trifluoroethyl)amino]ethyl}thio)phenyl]acetamide;
N-[4-({2-[[4-Cyano-3-(trifluoromethyl)phenyl](2,2,2-trifluoroethyl)amino]ethyl}thio)phenyl]-N-methylacetamide;
N-[4-({2-[[4-Cyano-3-(trifluoromethyl)phenyl](2,2,2-trifluoroethyl)amino]ethyl}thio)phenyl]methanesulfonamide;
4-[[2-(Pyrimidin-2-ylamino)ethyl](2,2,2-trifluoroethyl)amino]-2-(trifluoromethyl)benzonitrile;
4-[{2-[Methyl(pyrimidin-2-yl)amino]ethyl}(2,2,2-trifluoroethyl)amino]-2-(trifluoromethyl)benzonitrile;
N-{2-[[4-Cyano-3-(trifluoromethyl)phenyl](2,2,2-trifluoroethyl)amino]ethyl}benzamide;
4-[[3-(4-Fluorophenyl)propyl](2,2,2-trifluoroethyl)amino]-2-(trifluoromethyl)benzonitrile;
N-(4-{3-[[4-Cyano-3-(trifluoromethyl)phenyl](2,2,2-trifluoroethyl)amino]propyl}phenyl)acetamide;
4-[(3-Phenylpropyl)(2,2,2-trifluoroethyl)amino]-2-(trifluoromethyl)benzonitrile;
4-[[3-(3-Pyridinyl)propyl](2,2,2-trifluoroethyl)amino]-2-(trifluoromethyl)benzonitrile trifluoroacetate;
N-(4-{3-[[4-Cyano-3-(trifluoromethyl)phenyl](2,2-dimethylpropyl)amino]propyl}phenyl)acetamide;
1,1-Dimethylethyl N-{3-[4-(acetylamino)phenyl]propyl}-N-[4-cyano-3-(trifluoromethyl)phenyl]glycinate;
1,1-Dimethylethyl N-[4-cyano-3-(trifluoromethyl)phenyl]-N-(2-{[4-(methyloxy)phenyl]oxy}ethyl)glycinate;
$N^2$-[4-Cyano-3-(trifluoromethyl)phenyl]-$N^2$-(cyclopropylmethyl)-$N^1$-(4-fluorophenyl)glycinamide;
$N^2$-[4-Cyano-3-(trifluoromethyl)phenyl]-$N^2$-(cyclopropylmethyl)-$N^1$-(1S)-1-(phenylmethyl)glycinamide;
$N^2$-[4-Cyano-3-(trifluoromethyl)phenyl]-$N^2$-(cyclopropylmethyl)-$N^1$-[(4-fluorophenyl)methyl]glycinamide;
$N^2$-[4-Cyano-3-(trifluoromethyl)phenyl]-$N^2$-(cyclopropylmethyl)-$N^1$-[(1S)-1-phenylethyl]glycinamide;
$N^2$-[4-Cyano-3-(trifluoromethyl)phenyl]-$N^2$-(cyclopropylmethyl)-$N^1$-[(1R)-1-phenylethyl]glycinamide;
$N^2$-[4-Cyano-3-(trifluoromethyl)phenyl]-$N^2$-(cyclopropylmethyl)-$N^1$-(2-phenylethyl)glycinamide;
$N^2$-[4-Cyano-3-(trifluoromethyl)phenyl]-$N^2$-(cyclopropylmethyl)-$N^1$-[2-(4-fluorophenyl)ethyl]glycinamide;
$N^2$-[4-Cyano-3-(trifluoromethyl)phenyl]-$N^2$-(cyclopropylmethyl)-$N^1$-phenylalaninamide;
$N^2$-[4-Cyano-3-(trifluoromethyl)phenyl]-$N^2$-(cyclopropylmethyl)-$N^1$-(4-fluorophenyl)alaninamide;
$N^2$-[4-Cyano-3-(trifluoromethyl)phenyl]-$N^2$-(2-methylpropyl)-$N^1$-phenylglycinamide;
$N^2$-[4-Cyano-3-(trifluoromethyl)phenyl]-$N^1$-(4-fluorophenyl)-$N^2$-(2-methylpropyl)glycinamide;
$N^2$-[4-Cyano-3-(trifluoromethyl)phenyl]-$N^1$-phenyl-$N^2$-(2,2,2-trifluoroethyl)glycinamide;
$N^2$-[4-Cyano-3-(trifluoromethyl)phenyl]-$N^1$-(4-fluorophenyl)-$N^2$-(2,2,2-trifluoroethyl)glycinamide;
$N^1$-[4-(Acetylamino)phenyl]-$N^2$-[4-cyano-3-(trifluoromethyl)phenyl]-$N^2$-(2,2,2-trifluoroethyl)glycinamide;
$N^2$-[4-Cyano-3-(trifluoromethyl)phenyl]-$N^1$-(2-phenylethyl)-$N^2$-(2,2,2-trifluoroethyl)glycinamide;
2-[[4-Cyano-3-(trifluoromethyl)phenyl](2,2,2-trifluoroethyl)amino]-N-phenylbutanamide;

2-[[4-Cyano-3-(trifluoromethyl)phenyl](2,2,2-trifluoroethyl)amino]-N-(4-fluorophenyl)butanamide;

4-[[2-(1H-1,2,4-Triazol-1-yl)ethyl](2,2,2-trifluoroethyl)amino]-2-(trifluoromethyl)benzonitrile;

and salts thereof.

16. A compound of formula IB:

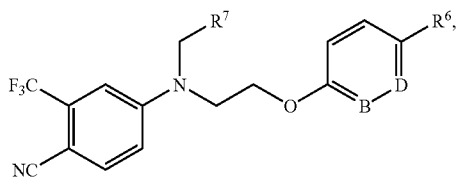

(IB)

where

| $R^7$ | B | D | $R^6$ |
|---|---|---|---|
| -Cyclopropyl | CH | CH | —NHC(O)CH$_3$ |
| —CF$_3$ | CH | CH | —NHC(O)CH$_3$ |
| —CF$_3$ | CH | CH | —SO$_2$NH$_2$ |
| —CF$_3$ | CH | CH | F |
| —CF$_3$ | CH | CH | —NHC(O)NH$_2$ |
| —CF$_3$ | CH | CH | —SO$_2$CH$_3$ |

-continued

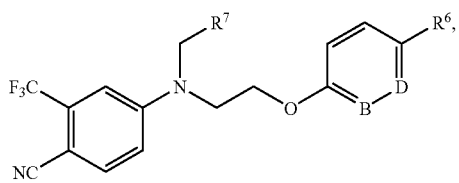

(IB)

where

| $R^7$ | B | D | $R^6$ |
|---|---|---|---|
| —CF$_3$ | CH | CH | —CF$_3$ |
| t-butyl | CH | CH | —NHC(O)CH$_3$ |
| t-butyl | CH | CH | F |
| —CF$_3$ | N | CH | —CF$_3$ |
| —CF$_3$ | N | CH | —CH$_3$ |
| t-butyl | N | CH | —CF$_3$ |
| t-butyl | CH | N | F. |

17. A pharmaceutical composition comprising a compound according to claim 1, and a pharmaceutically acceptable carrier.

* * * * *